United States Patent
Wetterich et al.

[11] Patent Number: 6,124,345
[45] Date of Patent: Sep. 26, 2000

[54] CARBAMOYL CARBOXYLIC ACID AMIDE OXIMES

[75] Inventors: Frank Wetterich, Mutterstadt; Karl Eicken, Wachenheim; Reinhard Kirstgen, Neustadt; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 09/147,305

[22] PCT Filed: May 26, 1997

[86] PCT No.: PCT/EP97/02687

§ 371 Date: Nov. 24, 1998

§ 102(e) Date: Nov. 24, 1998

[87] PCT Pub. No.: WO97/46518

PCT Pub. Date: Dec. 11, 1997

[30] Foreign Application Priority Data

May 31, 1996 [DE] Germany .................. 196 21 841

[51] Int. Cl.$^7$ .................. A01N 43/06; A01N 53/00; A01N 37/18; A01N 37/12; A01N 37/44
[52] U.S. Cl. .................. 514/438; 514/531; 514/542; 514/551; 549/76; 560/27; 560/29; 560/159
[58] Field of Search .................. 560/27, 29, 159; 549/76; 514/438, 542, 531, 551

[56] References Cited

FOREIGN PATENT DOCUMENTS

WO 95/23784  9/1995  WIPO .................. C07C 271/22
WO 95/23786  9/1995  WIPO .................. C07C 271/22

*Primary Examiner*—Johann Richter
*Assistant Examiner*—Brian J. Davis
*Attorney, Agent, or Firm*—Oblon, Spivak, McClelland, Maier & Neustadt, P.C.

[57] ABSTRACT

The present invention relates to carbomoylcarboxamide oximes of the formula (I):

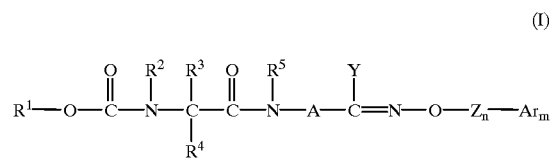

or salts thereof, processes for preparing the carbomoylcarboxamide oximes, compositions containing the carbomoylcarboxamide oximes and processes for controlling harmful fungi with an effective amount of the carbomoylcarboxamide oximes.

22 Claims, No Drawings

CARBAMOYL CARBOXYLIC ACID AMIDE OXIMES

The present invention relates to carbamoylcarboxamide oximes of the formula I

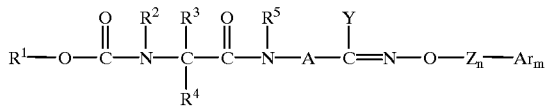

(I)

or salts thereof, where the variables have the following meanings:

$R^1$ is $C_1$–$C_8$-alkyl, $C_2$–$C_8$-alkenyl or $C_2$–$C_8$-alkynyl, it being possible for these radicals to be partially or fully halogenated and/or to carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, $C_3$–$C_7$-cycloalkyl, $C_3$–$C_7$-cycloalkenyl, aryl, aryloxy and hetaryl, it being in turn possible for the cyclic radicals to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, $C_3$–$C_7$-cycloalkyl or $C_3$–$C_7$-cycloalkenyl, it being possible for these radicals to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, a non-aromatic 4- to 8-membered ring which, as ring members, in addition to carbon may contain one or two of the hetero atoms oxygen, sulfur and nitrogen, it being possible for the carbons in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, the second and any further nitrogen as ring heteroatom carrying hydrogen or a $C_1$–$C_4$-alkyl group, aryl or hetaryl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, it being in turn possible for the cyclic substituents to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, $W^1W^2C=N-$, where $W^1$ is $C_1$–$C_8$-alkyl which may be partially or fully halogenated and/or carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, aryl, aryloxy and hetaryl, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy, $C_2$–$C_8$-alkenyl or $C_2$–$C_8$-alkynyl, it being possible for these radicals to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, $C_3$–$C_7$-cycloalkyl or $C_3$–$C_7$-cycloalkenyl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryl-($C_1$–$C_4$)-alkyl, it being possible for the aryl-containing groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, aryl or hetaryl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, and $W^2$ is hydrogen or independently one of the groups $W^1$;

$R^2$ is hydrogen or is $C_1$–$C_8$-alkyl or $C_3$–$C_7$-cycloalkyl, both of which may be partially or fully halogenated;

$R^3$ is $C_1$–$C_8$-alkyl or $C_3$–$C_7$-cycloalkyl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl or phenyl-($C_1$–$C_4$)-alkyl, it being possible for the phenyl radical to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

$R^4$ is hydrogen or one of the groups listed under $R^3$ or $R^3$ and $R^4$, together with the carbon that they are attached to, form a 4- to 8-membered ring which, as ring members, in addition to carbon may contain one or two of the hetero atoms oxygen, sulfur and nitrogen, it being possible for the carbons in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, nitrogen as hetero atom carrying hydrogen or a $C_1$–$C_4$-alkyl group;

$R^5$ is a radical $R^2$;

A is $C_1$–$C_8$-alkylene, it being possible for these radicals to be partially or fully halogenated and/or to carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, aryl and aryloxy, or $C_3$–$C_7$-cycloalkylene, it being possible for these radicals to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$- haloalkyl, $C_1-C_4$-alkoxy, $C_1-C_4$-haloalkoxy, $C_1-C_4$-alkylthio, $C_1-C_4$-alkoxycarbonyl, aryl and aryloxy;

Y is hydrogen, $C_1-C_8$-alkyl, it being possible for this radical to be partially or fully halogenated and/or to carry one or independently two or three of the following groups: cyano, $C_1-C_4$-alkoxyalkyl, $C_1-C_4$-haloalkyl, $C_1-C_4$-alkoxy, $C_1-C_4$-haloalkoxy, $C_1-C_4$-alkylthio and $C_1-C_4$-alkoxycarbonyl, aryl and aryloxy, $C_3-C_7$-cycloalkyl, it being possible for this radical to be partially or fully halogenated and/or to carry one or independently two or three of the following groups: cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio, $C_1-C_4$-alkoxycarbonyl, aryl, aryloxy and aryl-($C_1-C_4$)-alkyl, it being in turn possible for the cyclic groups to carry one or independently two or three of the following substituents: halogen, cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio, $C_1-C_4$-alkoxycarbonyl, aryl and aryloxy or aryl, it being possible for these radicals to carry one or independently two or three of the following groups: halogen, cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio, $C_1-C_4$-alkoxycarbonyl, aryl and aryloxy;

Z is $C_1-C_8$-alkylene, it being possible for this radical to be partially or fully halogenated and/or to carry one or independently two or three of the following groups: cyano, $C_1-C_4$-alkoxyalkyl, $C_1-C_4$-haloalkyl, $C_1-C_4$-alkoxy, $C_1-C_4$-haloalkoxy, $C_1-C_4$-alkylthio and $C_1-C_4$-alkoxycarbonyl, aryl and aryloxy, $C_1-C_8$-alkyleneoxy, it being possible for this radical to be partially or fully halogenated and/or to carry one or independently two or three of the following groups: cyano, $C_1-C_4$-alkylthio and $C_1-C_4$-alkoxycarbonyl, aryl and aryloxy, $C_3-C_7$-cycloalkylene, it being possible for this radical to be partially or fully halogenated and/or to carry one or independently two or three of the following groups: cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio, $C_1-C_4$-alkoxycarbonyl, aryl, aryloxy and aryl-($C_1-C_4$)-alkyl, it being in turn possible for the cyclic groups to carry one or independently two or three of the following substituents: halogen, cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio, $C_1-C_4$-alkoxycarbonyl, aryl and aryloxy;

n is 0, 1 or 2;

Ar is aryl or hetaryl, it being possible for these radicals to carry one or independently two or three of the following groups: halogen, cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio, $C_1-C_4$-alkoxycarbonyl, aryl, aryloxy and hetaryl, it being in turn possible for the cyclic substituents to carry one or independently two or three of the following substituents: halogen, cyano, $C_1-C_4$-alkyl, $C_1-C_4$-alkoxyalkyl, $C_1-C_4$-haloalkyl, $C_1-C_4$-alkoxy, $C_1-C_4$-haloalkoxy, $C_1-C_4$-alkylthio and $C_1-C_4$-alkoxycarbonyl;

m is 0, 1 or 2.

The invention further relates to processes for preparing the compounds I, compositions comprising the compounds I and to the use of the compounds I and the compositions for controlling harmful fungi.

Carbamoylcarboxamides and carbamoylacyl hydrazides having fungicidal action are known to the person skilled in the art (cf. WO-A 95/23 784, WO-A 95/23 785, WO-A 95/23 786, WO-A 95/33 710, EP-A 672 654, WO-A 96/07 638 and the prior German application having the reference number 195 31 814.5).

However, the action against harmful fungi of the compounds described in the abovementioned documents is still not satisfactory.

It is an object of the present invention to provide novel carbamoylcarboxylic acid derivatives having improved properties for controlling harmful fungi.

We have found that this object is achieved by the compounds I defined at the outset, by processes for preparing them, compositions comprising them and by their use and the use of the compositions for controlling harmful fungi.

The compounds I can be prepared in a customary manner from the appropriate carbamoylcarboxylic acids II. The compounds I are preferably obtained by the processes A or B described below (the literature reference "Houben-Weyl" refers to: Houben-Weyl, Methoden der Organischen Chemie, 4th edition, Thieme Verlag, Stuttgart).

Process A

The carbamoylcarboxamide oximes I are obtained (cf. Scheme 1 below) by reacting the carbamoylcarboxylic acids II with the amines III to give the compounds IV, oxidizing the compounds IV to the carbonyl compounds V and reacting these in turn with oxyamines VI.

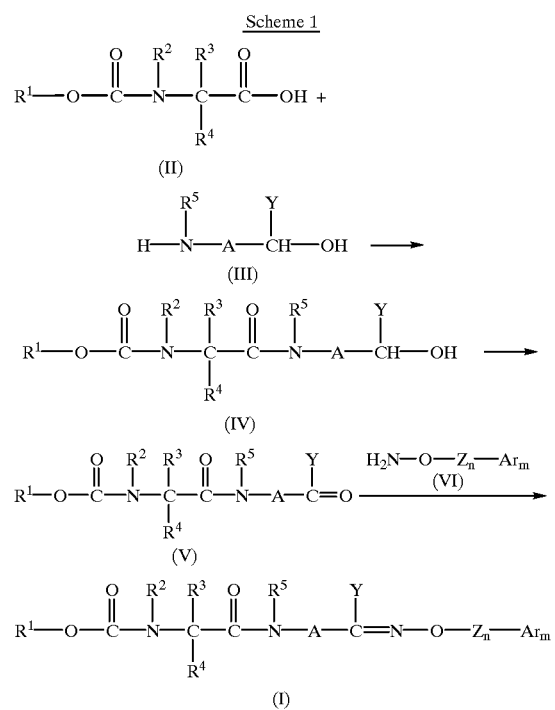

Scheme 1

The carbamoylcarboxylic acids II are known or can be prepared by known methods, in particular starting from the amino acids they are based on (cf. "Houben-Weyl", Volume 15/1, page 46 to page 305, in particular page 117 to page 125).

The amines III are also known or are easily obtainable (cf. J. Amer. Chem. Soc. 110 (1988), 5195 ff.; Tetrahedron 28 (1972), 3475 ff.).

When preparing the amides IV, the carbamoylcarboxylic acids II are preferably initially converted into carboxyl-activated derivatives, in particular into acyl cyanides or anhydrides (cf. Tetrahedron Letters, 18 (1973), 1595–1598 or "Houben-Weyl", Volume 15/1, page 28 to page 32). These derivatives are then reacted with the amines III in the presence of bases.

Suitable for preparing the carboxyl-activated acyl cyanides is for example the reaction of the carbamoylcarboxylic acids II with diethyl cyanophosphonate, especially in an inert solvent such as tetrahydrofuran or toluene.

The carboxyl-activated anhydrides are preferably prepared by reacting the carbamoylcarboxylic acid II with chloroformates such as isobutyl chloroformate in the presence of bases and, if appropriate, in an inert solvent such as toluene or tetrahydrofuran.

The reaction of the amines III with the carboxyl-activated carbamoylcarboxylic acids II is preferably carried out in a solvent such as dichloromethane, tetrahydrofuran or toluene.

Bases which can be used are in particular the amines III themselves, the latter customarily being recovered from the crude product.

In a preferred embodiment of this process step, the carbamoylcarboxylic acid II, the amine III, the reagent suitable for generating the carboxyl-activated derivative of the carbamoylcarboxylic acid II and the base are reacted in a one-pot process, if appropriate in an inert solvent, and the crude product is then worked up in a customary manner to give the carbamoylcarboxamide I.

The oxidation of the amines IV to the compounds V can be carried out in a customary manner, in particular using sodium hypochlorite in a buffered solution and in the presence of catalytic amounts of 2,2,6,6-tetramethyl-1-piperidinyloxy (TEMPO) (cf. J. Org. Chem. 52 (1987), 2559 ff.; Org. Synth. 96 (1990) 212 ff.).

The oxyamines VI are obtainable by generally known methods (cf. DE-A 36 15 473). EP-A 588 146 describes the reaction with the compounds V.

A variant of this process step leading from the compounds V to the compounds I consists in first reacting (cf. Scheme 2) the compounds V with a salt of the hydroxylamine in the presence of a base to give the oximes VIII and reacting the latter, after deprotonation, with compounds IX in which X' is a conventional nucleofugal leaving group such as bromine.

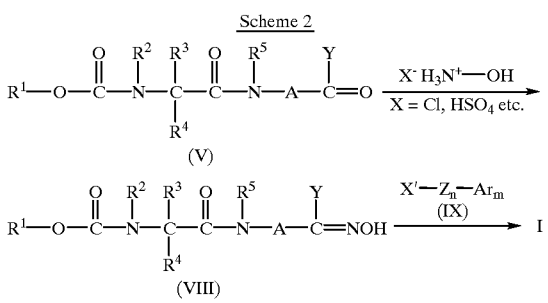

Process B

The carbamoylcarboxamides I are obtained by converting the carbamoylcarboxamides I where the group $R^1$—O—(CO) is a protecting group which can be removed in a conventional manner into amino acid amides IV and reacting these with chloroformyl oximes V in the presence of bases.

Step Ba: Preparation of the amino acid amides VII

The group $R^1$—O—(CO) can be removed from the carbamoylcarboxamide oximes I (cf. Scheme 3) in a conventional manner (cf. "Houben-Weyl", Volume 15/1, page 46 to page 305, in particular page 126 to page 129).

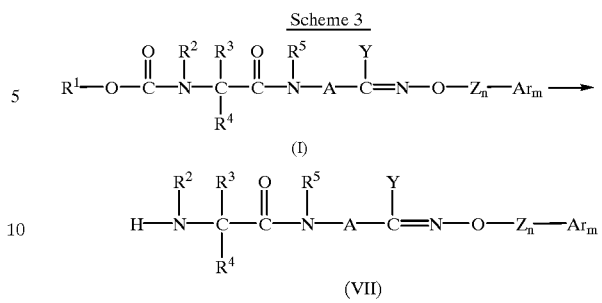

Suitable removable groups contain a tert-butyl or the benzyl group as radical $R^1$.

If $R^1$=tert-butyl, the removal is carried out for example by reaction with an acid, in particular a protic acid such as hydrochloric acid or trifluoroacetic acid (ibid., page 126 to page 129).

The carbamoylcarboxamides I suitable as starting materials can be obtained by known processes (cf. "Houben-Weyl", Volume 15/1, page 28 to page 32) or, in particular, according to the process A according to the invention.

Step Bb: Preparation of the carbamoylcarboxamides I

The amino acid amides VII resulting from the synthesis step (Ba) are reacted with the chloroformyl oximes VIII in the presence of bases (Scheme 4).

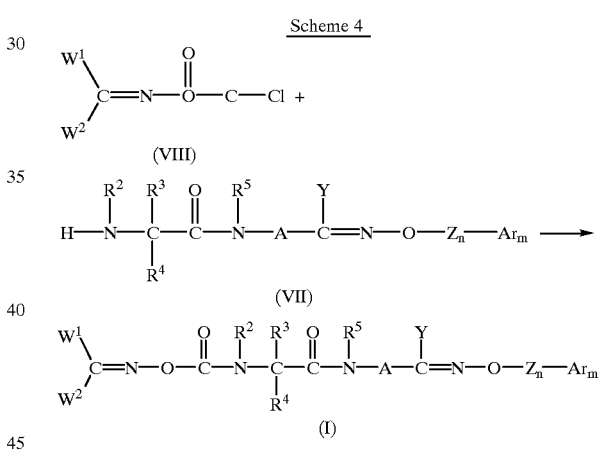

The chloroformyl oximes VIII are known or can be prepared by known processes, for example by phosgenation of oximes (cf. for example Zeitschrift für Chemie 9 (1967), 344–345).

The reaction is preferably carried out in an organic solvent, especially toluene, methylene chloride or tetrahydrofuran, or in mixtures of these.

Suitable bases are both inorganic and organic bases, among which organic bases are preferred and tertiary amines such as triethylamine, pyridine and N-methylpiperidine are particularly preferred.

As a rule, the reaction is carried out at from (−40) to 50, preferably at from (−10) to 20° C.

The practice of this reaction is otherwise familiar to the person skilled in the art, so further explanation to this end can be dispensed with (cf. "Houben-Weyl", Volume 15/1, page 117 to page 125, or Dev. Endocrinol., 13 (Neurohypophyseal Pept. Horm. Other Biol. Act. Pept.) (1981), 37–47).

The reaction mixtures obtained by processes A and B are worked up in a customary manner, eg. by mixing with water, separation of the phases and if appropriate chromatographic purification of the crude products. The intermediates and final products are in some cases obtained in the form of colorless or slightly brownish, viscous oils, which can be freed from volatile components under reduced pressure and at moderately elevated temperature. If the intermediates and final products are obtained as solids, purification can also be carried out, for example, by recrystallizing or digesting.

Depending on the nature of the substituents, the compounds of the formula I can in some cases be present as geometric and/or optical isomers or isomer mixtures. Both the pure isomers and the mixtures of isomers exhibit the fungicidal action.

The salts of the acid-stable compounds I which contain basic centers, especially basic nitrogen atoms, in particular with mineral acids such as sulfuric acid and phosphoric acid or Lewis acids such as zinc chloride, are also part of the invention, Customarily, in this case the nature of the salt does not matter. According to the invention, those salts are preferred which do not damage the plants, areas, materials or spaces to be kept free from harmful fungi or animal pests and do not adversely affect the action of the compounds I. Of particular importance are salts which are suitable for agricultural purposes.

The salts of the compounds I are accessible in a manner known per se, especially by reacting the corresponding compounds I with the acids mentioned in water or an inert organic solvent at from (−80) to 120° C., preferably from 0 to 60° C.

In the definitions of the compounds I given at the beginning, collective terms were used which are representative of the following substituents:

halogen: fluorine, chlorine, bromine and iodine;

alkyl: straight-chain or branched alkyl groups having 1 to 8 carbon atoms, eg. $C_1$–$C_6$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl or partially or fully halogenated alkyl: straight-chain or branched alkyl groups having 1 to 4 or 8 carbon atoms (as mentioned above), where in these groups the hydrogen atoms can be replaced partially or completely by halogen atoms (as mentioned above), eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkoxy groups having 1 to 4 carbon atoms, eg. $C_1$–$C_3$-alkoxy such as methyloxy, ethyloxy, propyloxy and 1-methylethyloxy;

alkoxyalkyl: straight-chain or branched alkyl groups having 1 to 8 carbon atoms (as mentioned above), which in any desired position carry a straight-chain or branched alkoxy group (as mentioned above) having, in the case of $C_1$–$C_4$-alkoxyalkyl, 1 to 4 carbon atoms, such as methoxymethyl, ethoxymethyl, n-propoxymethyl, n-butoxymethyl, 1-methoxyethyl, 2-methoxyethyl, 1-ethoxyethyl, 2-ethoxyethyl, 2-n-propoxyethyl and 2-butoxyethyl;

haloalkoxy: straight-chain or branched alkoxy groups having 1 to 4 carbon atoms (as mentioned above), where in these groups the hydrogen atoms can be replaced partially or completely by halogen atoms (as mentioned above), eg. $C_1$–$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy;

alkylthio: straight-chain or branched alkyl groups having 1 to 4 carbon atoms (as mentioned above) which are bonded to the structure via a sulfur atom (—S—), eg. $C_1$–$C_4$-alkylthio such as methylthio, ethylthio, propylthio, 1-methylethylthio, n-butylthio and tert-butylthio;

alkoxycarbonyl: straight-chain or branched alkoxy groups having 1 to 4 C atoms (as mentioned above), which are bonded to the structure via a carbonyl group (—CO—);

alkenyl: straight-chain or branched alkenyl groups having 2 to 8 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 2-methyl-1-propenyl, 1-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched alkynyl groups having 2 to 8 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl; cycloalkyl: monocyclic alkyl groups having 3 to 7 carbon ring members, eg. $C_3$–$C_7$-cycloalkyl such as cyclopropyl, cyclobutyl, cyclopentyl, cyclohexyl and cycloheptyl;

cycloalkenyl: monocyclic alkyl groups having 5 to 7 carbon ring members which contain one or more double bonds, eg. $C_5$–$C_7$-cycloalkenyl such as cyclopentenyl, cyclohexenyl and cycloheptenyl;

non-aromatic 4- to 8-membered rings which as ring members in addition to carbon also contain one or two oxygen, sulfur or nitrogen atoms, such as saturated 5- or 6-membered rings having 1 or 2 nitrogen and/or oxygen atoms such as 3-tetrahydrofuranyl, 1-piperidinyl, 2-piperidinyl, 3-piperidinyl, 4-piperidinyl, 2-tetrahydropyranyl, 3-tetrahydropyranyl, 4-tetrahydropyranyl, 2-morpholinyl and 3-morpholinyl;

aryl: monocyclic or polycyclic aromatic groups having 6 to 10 C atoms, such as phenyl and naphthyl;

arylalkyl: aryl groups (as mentioned above), which in the case of aryl-($C_1$–$C_4$)-alkyl are bonded to the structure via alkyl groups having 1 to 4 carbon atoms (as mentioned above), eg. phenyl-($C_1$–$C_4$)-alkyl such as benzyl, 2-phenylethyl, 3-phenylpropyl, 4-phenylbutyl, 1-phenylethyl, 1-phenylpropyl and 1-phenylbutyl;

aryloxy: aryl groups (as mentioned above), which are bonded to the structure via an oxygen atom (—O—), such as phenoxy, 1-naphthoxy and 2-naphthoxy;

hetaryl: aromatic mono- or polycyclic radicals which in addition to carbon ring members can additionally contain 1 to 4 nitrogen atoms or 1 to 3 nitrogen atoms and an oxygen or a sulfur atom or an oxygen or a sulfur atom, eg.:

5-membered hetaryl, containing 1 to 3 nitrogen atoms: 5-membered ring hetaryl groups which in addition to carbon atoms can contain 1 to 3 nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl, containing 1 to 4 nitrogen atoms or 1 to 3 nitrogen atoms and 1 sulfur atom or oxygen atom or 1 oxygen or 1 sulfur atom: 5-membered ring hetaryl groups which in addition to carbon atoms can contain 1 to 4 nitrogen atoms or 1 to 3 nitrogen atoms and 1 sulfur or oxygen atom or 1 oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl, containing 1 to 3 nitrogen atoms or 1 nitrogen atom and/or an oxygen or sulfur atom: 5-membered ring hetaryl groups which in addition to carbon atoms can contain 1 to 4 nitrogen atoms or 1 to 3 nitrogen atoms and 1 sulfur or oxygen atom or 1 oxygen or a sulfur atom as ring members, and in which 2 adjacent carbon ring members or 1 nitrogen and 1 adjacent carbon ring member can be bridged by a buta-1,3-diene-1,4-diyl group;

5-membered hetaryl bonded via nitrogen, containing 1 to 4 nitrogen atoms, or benzo-fused 5-membered hetaryl bonded via nitrogen, containing 1 to 3 nitrogen atoms: 5-membered ring hetaryl groups which in addition to carbon atoms can contain 1 to 4 nitrogen atoms or 1 to 3 nitrogen atoms as ring members, and in which 2 adjacent carbon ring members or a nitrogen and an adjacent carbon ring member can be bridged by a buta-1,3-diene-1,4-diyl group, where these rings are bonded to the structure via one of the nitrogen ring members;

6-membered hetaryl, containing 1 to 3 or 1 to 4 nitrogen atoms: 6-membered ring hetaryl groups which in addition to carbon atoms can contain 1 to 3 or 1 to 4 nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing 1 to 4 nitrogen atoms: 6-membered ring hetaryl groups in which 2 adjacent carbon ring members can be bridged by a buta-1,3-diene-1,4-diyl group, eg. quinoline, isoquinoline, quinazoline and quinoxaline.

The statement "partially or fully halogenated" is intended to express that in the groups characterized in this way the hydrogen atoms can be partially or fully replaced by identical or different halogen atoms as mentioned above.

With respect to their biological action against harmful fungi and animal pests, compounds I are preferred where the radicals have the following preferred meanings, namely on their own or in combination:

$R^1$ is isopropyl, sec-butyl, tert-butyl or phenyl;

$R^2$ is hydrogen;

$R^3$ and $R^4$: one of these radicals is hydrogen and the other is isopropyl, the carbon carrying the radicals $R^3$ and $R^4$ preferably being in the S configuration, in particular if the two radicals $R^3$ and $R^4$ have the abovementioned meanings and additionally in the case of any other meaning;

$R^5$ is hydrogen;

A is $CH_2CH_2$, preferably $CH_2$ and $C(CH_3)_2$, in particular $CH(CH_3)CH_2$ and especially $CH(CH_3)$, the radical $CH(CH_3)$ preferably being racemic or in the R configuration;

Y is phenyl and in particular hydrogen or methyl;

Z is $CH_2O$, preferably $CH_2CH_2$, in particular $CH(CH_3)$ and especially $CH_2$;

n is 1 or 2;

Ar is phenyl which is unsubstituted or substituted, especially by chlorine, methyl, methoxy or cyano;

m is 1.

With respect to their biological activity, the compounds I' compiled in the following Table A are very particularly preferred:

Table A

TABLE A $$R^1-O-\overset{O}{\underset{}{C}}-NH-\overset{\underset{S}{CH(CH_3)_2}}{\underset{}{CH}}-\overset{O}{\underset{}{C}}-NH-A-\overset{Y}{\underset{}{C}}=N-O-Z-Ar \quad (I')$$

| No. | R¹ | A | Y | Z | Ar |
|---|---|---|---|---|---|
| 1.1 | CH(CH₃)₂ | CH(CH₃) | CH₃ | CH₂ | 4-Cl—C₆H₄ |
| 1.2 | CH(CH₃)₂ | CH(CH₃) | CH₃ | CH₂ | 4-CH₃—C₆H₄ |
| 1.3 | CH(CH₃)₂ | CH(CH₃) | CH₃ | CH₂ | 4-CH₃O—C₆H₄ |
| 1.4 | CH(CH₃)₂ | CH(CH₃) | CH₃ | CH₂ | 4-CN—C₆H₄ |
| 1.5 | CH(CH₃)₂ | CH(CH₃) | CH₃ | CH₂ | 3-Cl—C₆H₄ |
| 1.6 | CH(CH₃)₂ | CH(CH₃) | CH₃ | CH₂ | 3-CH₃—C₆H₄ |
| 1.7 | CH(CH₃)₂ | CH(CH₃) | CH₃ | CH₂ | 3-CH₃O—C₆H₄ |
| 1.8 | CH(CH₃)₂ | CH(CH₃) | CH₃ | CH₂ | 3-CN—C₆H₄ |
| 1.9 | CH(CH₃)₂ | CH(CH₃) | CH₃ | CH₂ | 2-Cl—C₆H₄ |
| 1.10 | CH(CH₃)₂ | CH(CH₃) | CH₃ | CH₂ | 2-CH₃—C₆H₄ |
| 1.11 | CH(CH₃)₂ | CH(CH₃) | CH₃ | CH₂ | 2-CH₃O—C₆H₄ |
| 1.12 | CH(CH₃)₂ | CH(CH₃) | CH₃ | CH₂ | 2-CN—C₆H₄ |
| 1.13 | CH(CH₃)₂ | CH(CH₃) | CH₃ | CH₂ | 3,4-(CH₃O)₂C₆H₃ |
| 1.14 | CH(CH₃)₂ | CH(CH₃) | CH₃ | CH₂ | 2,4-Cl₂—C₆H₃ |
| 1.15 | CH(CH₃)₂ | CH(CH₃) | CH₃ | CH₂ | 2,4-(CH₃)₂—C₆H₃ |
| 1.16 | CH(CH₃)₂ | CH(CH₃) | CH₃ | CH₂ | 3,4-(CH₃)₂C₆H₃ |
| 1.17 | CH(CH₃)₂ | CH(CH₃) | CH₃ | CH₂ | 4-NO₂—C₆H₄ |
| 1.18 | CH(CH₃)C₂H₅ | CH(CH₃) | CH₃ | CH₂ | 4-Cl—C₆H₄ |
| 1.19 | CH(CH₃)C₂H₅ | CH(CH₃) | CH₃ | CH₂ | 4-CH₃—C₆H₄ |
| 1.20 | CH(CH₃)C₂H₅ | CH(CH₃) | CH₃ | CH₂ | 4-CH₃O—C₆H₄ |
| 1.21 | CH(CH₃)C₂H₅ | CH(CH₃) | CH₃ | CH₂ | 4-CN—C₆H₄ |
| 1.22 | CH(CH₃)C₂H₅ | CH(CH₃) | CH₃ | CH₂ | 3-Cl—C₆H₄ |
| 1.23 | CH(CH₃)C₂H₅ | CH(CH₃) | CH₃ | CH₂ | 3-CH₃—C₆H₄ |
| 1.24 | CH(CH₃)C₂H₅ | CH(CH₃) | CH₃ | CH₂ | 3-CH₃O—C₆H₄ |
| 1.25 | CH(CH₃)C₂H₅ | CH(CH₃) | CH₃ | CH₂ | 3-CN—C₆H₄ |
| 1.26 | CH(CH₃)C₂H₅ | CH(CH₃) | CH₃ | CH₂ | 2-Cl—C₆H₄ |
| 1.27 | CH(CH₃)C₂H₅ | CH(CH₃) | CH₃ | CH₂ | 2-CH₃—C₆H₄ |
| 1.28 | CH(CH₃)C₂H₅ | CH(CH₃) | CH₃ | CH₂ | 2-CH₃O—C₆H₄ |
| 1.29 | CH(CH₃)C₂H₅ | CH(CH₃) | CH₃ | CH₂ | 2-CN—C₆H₄ |
| 1.30 | CH(CH₃)C₂H₅ | CH(CH₃) | CH₃ | CH₂ | 3,4-(CH₃O)₂C₆H₃ |
| 1.31 | CH(CH₃)C₂H₅ | CH(CH₃) | CH₃ | CH₂ | 2,4-Cl₂—C₆H₃ |
| 1.32 | CH(CH₃)C₂H₅ | CH(CH₃) | CH₃ | CH₂ | 2,4-(CH₃)₂—C₆H₃ |
| 1.33 | CH(CH₃)C₂H₅ | CH(CH₃) | CH₃ | CH₂ | 3,4-(CH₃)₂C₆H₃ |
| 1.34 | CH(CH₃)C₂H₅ | CH(CH₃) | CH₃ | CH₂ | 4-NO₂—C₆H₄ |
| 1.35 | C(CH₃)₃ | CH(CH₃) | CH₃ | CH₂ | 4-Cl—C₆H₄ |
| 1.36 | C(CH₃)₃ | CH(CH₃) | CH₃ | CH₂ | 4-CH₃—C₆H₄ |
| 1.37 | C(CH₃)₃ | CH(CH₃) | CH₃ | CH₂ | 4-CH₃O—C₆H₄ |
| 1.38 | C(CH₃)₃ | CH(CH₃) | CH₃ | CH₂ | 4-CN—C₆H₄ |
| 1.39 | C(CH₃)₃ | CH(CH₃) | CH₃ | CH₂ | 3-Cl—C₆H₄ |
| 1.40 | C(CH₃)₃ | CH(CH₃) | CH₃ | CH₂ | 3-CH₃—C₆H₄ |
| 1.41 | C(CH₃)₃ | CH(CH₃) | CH₃ | CH₂ | 3-CH₃O—C₆H₄ |
| 1.42 | C(CH₃)₃ | CH(CH₃) | CH₃ | CH₂ | 3-CN—C₆H₄ |
| 1.43 | C(CH₃)₃ | CH(CH₃) | CH₃ | CH₂ | 2-Cl—C₆H₄ |
| 1.44 | C(CH₃)₃ | CH(CH₃) | CH₃ | CH₂ | 2-CH₃—C₆H₄ |
| 1.45 | C(CH₃)₃ | CH(CH₃) | CH₃ | CH₂ | 2-CH₃O—C₆H₄ |
| 1.46 | C(CH₃)₃ | CH(CH₃) | CH₃ | CH₂ | 2-CN—C₆H₄ |
| 1.47 | C(CH₃)₃ | CH(CH₃) | CH₃ | CH₂ | 3,4-(CH₃O)₂C₆H₃ |
| 1.48 | C(CH₃)₃ | CH(CH₃) | CH₃ | CH₂ | 2,4-Cl₂—C₆H₃ |
| 1.49 | C(CH₃)₃ | CH(CH₃) | CH₃ | CH₂ | 2,4-(CH₃)₂—C₆H₃ |
| 1.50 | C(CH₃)₃ | CH(CH₃) | CH₃ | CH₂ | 3,4-(CH₃)₂C₆H₃ |
| 1.51 | C(CH₃)₃ | CH(CH₃) | CH₃ | CH₂ | 4-NO₂—C₆H₄ |
| 1.52 | CH(CH₃)₂ | C(CH₃)₂—CH₂ | CH₃ | CH₂ | 4-Cl—C₆H₄ |
| 1.53 | CH(CH₃)₂ | C(CH₃)₂—CH₂ | CH₃ | CH₂ | 4-CH₃—C₆H₄ |
| 1.54 | CH(CH₃)₂ | C(CH₃)₂—CH₂ | CH₃ | CH₂ | 4-CH₃O—C₆H₄ |
| 1.55 | CH(CH₃)₂ | C(CH₃)₂—CH₂ | CH₃ | CH₂ | 4-CN—C₆H₄ |
| 1.56 | CH(CH₃)₂ | C(CH₃)₂—CH₂ | CH₃ | CH₂ | 3-Cl—C₆H₄ |
| 1.57 | CH(CH₃)₂ | C(CH₃)₂—CH₂ | CH₃ | CH₂ | 3-CH₃—C₆H₄ |
| 1.58 | CH(CH₃)₂ | C(CH₃)₂—CH₂ | CH₃ | CH₂ | 3-CH₃O—C₆H₄ |
| 1.59 | CH(CH₃)₂ | C(CH₃)₂—CH₂ | CH₃ | CH₂ | 3-CN—C₆H₄ |
| 1.60 | CH(CH₃)₂ | C(CH₃)₂—CH₂ | CH₃ | CH₂ | 2-Cl—C₆H₄ |
| 1.61 | CH(CH₃)₂ | C(CH₃)₂—CH₂ | CH₃ | CH₂ | 2-CH₃—C₆H₄ |
| 1.62 | CH(CH₃)₂ | C(CH₃)₂—CH₂ | CH₃ | CH₂ | 2-CH₃O—C₆H₄ |
| 1.63 | CH(CH₃)₂ | C(CH₃)₂—CH₂ | CH₃ | CH₂ | 2-CN—C₆H₄ |
| 1.64 | CH(CH₃)₂ | C(CH₃)₂—CH₂ | CH₃ | CH₂ | 3,4-(CH₃O)₂C₆H₃ |
| 1.65 | CH(CH₃)₂ | C(CH₃)₂—CH₂ | CH₃ | CH₂ | 2,4-Cl₂—C₆H₃ |
| 1.66 | CH(CH₃)₂ | C(CH₃)₂—CH₂ | CH₃ | CH₂ | 2,4-(CH₃)₂—C₆H₃ |
| 1.67 | CH(CH₃)₂ | C(CH₃)₂—CH₂ | CH₃ | CH₂ | 3,4-(CH₃)₂C₆H₃ |
| 1.68 | CH(CH₃)₂ | C(CH₃)₂—CH₂ | CH₃ | CH₂ | 4-NO₂—C₆H₄ |

TABLE A-continued $$R^1-O-\overset{O}{\underset{}{C}}-NH-\underset{\underline{S}}{\overset{CH(CH_3)_2}{\underset{|}{CH}}}-\overset{O}{\underset{}{C}}-NH-A-\overset{Y}{\underset{|}{C}}=N-O-Z-Ar \quad (I')$$

| No. | R¹ | A | Y | Z | Ar |
|---|---|---|---|---|---|
| 1.69 | CH(CH₃)C₂H₅ | C(CH₃)₂—CH₂ | CH₃ | CH₂ | 4-Cl—C₆H₄ |
| 1.70 | CH(CH₃)C₂H₅ | C(CH₃)₂—CH₂ | CH₃ | CH₂ | 4-CH₃—C₆H₄ |
| 1.71 | CH(CH₃)C₂H₅ | C(CH₃)₂—CH₂ | CH₃ | CH₂ | 4-CH₃O—C₆H₄ |
| 1.72 | CH(CH₃)C₂H₅ | C(CH₃)₂—CH₂ | CH₃ | CH₂ | 4-CN—C₆H₄ |
| 1.73 | CH(CH₃)C₂H₅ | C(CH₃)₂—CH₂ | CH₃ | CH₂ | 3-Cl—C₆H₄ |
| 1.74 | CH(CH₃)C₂H₅ | C(CH₃)₂—CH₂ | CH₃ | CH₂ | 3-CH₃—C₆H₄ |
| 1.75 | CH(CH₃)C₂H₅ | C(CH₃)₂—CH₂ | CH₃ | CH₂ | 3-CH₃O—C₆H₄ |
| 1.76 | CH(CH₃)C₂H₅ | C(CH₃)₂—CH₂ | CH₃ | CH₂ | 3-CN—C₆H₄ |
| 1.77 | CH(CH₃)C₂H₅ | C(CH₃)₂—CH₂ | CH₃ | CH₂ | 2-Cl—C₆H₄ |
| 1.78 | CH(CH₃)C₂H₅ | C(CH₃)₂—CH₂ | CH₃ | CH₂ | 2-CH₃—C₆H₄ |
| 1.79 | CH(CH₃)C₂H₅ | C(CH₃)₂—CH₂ | CH₃ | CH₂ | 2-CH₃O—C₆H₄ |
| 1.80 | CH(CH₃)C₂H₅ | C(CH₃)₂—CH₂ | CH₃ | CH₂ | 2-CN—C₆H₄ |
| 1.81 | CH(CH₃)C₂H₅ | C(CH₃)₂—CH₂ | CH₃ | CH₂ | 3,4-(CH₃O)₂C₆H₃ |
| 1.82 | CH(CH₃)C₂H₅ | C(CH₃)₂—CH₂ | CH₃ | CH₂ | 2,4-Cl₂—C₆H₃ |
| 1.83 | CH(CH₃)C₂H₅ | C(CH₃)₂—CH₂ | CH₃ | CH₂ | 2,4-(CH₃)₂—C₆H₃ |
| 1.84 | CH(CH₃)C₂H₅ | C(CH₃)₂—CH₂ | CH₃ | CH₂ | 3,4-(CH₃)₂C₆H₃ |
| 1.85 | CH(CH₃)C₂H₅ | C(CH₃)₂—CH₂ | CH₃ | CH₂ | 4-NO₂—C₆H₄ |
| 1.86 | C(CH₃)₃ | C(CH₃)₂—CH₂ | CH₃ | CH₂ | 4-Cl—C₆H₄ |
| 1.87 | C(CH₃)₃ | C(CH₃)₂—CH₂ | CH₃ | CH₂ | 4-CH₃—C₆H₄ |
| 1.88 | C(CH₃)₃ | C(CH₃)₂—CH₂ | CH₃ | CH₂ | 4-CH₃O—C₆H₄ |
| 1.89 | C(CH₃)₃ | C(CH₃)₂—CH₂ | CH₃ | CH₂ | 4-CN—C₆H₄ |
| 1.90 | C(CH₃)₃ | C(CH₃)₂—CH₂ | CH₃ | CH₂ | 3-Cl—C₆H₄ |
| 1.91 | C(CH₃)₃ | C(CH₃)₂—CH₂ | CH₃ | CH₂ | 3-CH₃—C₆H₄ |
| 1.92 | C(CH₃)₃ | C(CH₃)₂—CH₂ | CH₃ | CH₂ | 3-CH₃O—C₆H₄ |
| 1.93 | C(CH₃)₃ | C(CH₃)₂—CH₂ | CH₃ | CH₂ | 3-CN—C₆H₄ |
| 1.94 | C(CH₃)₃ | C(CH₃)₂—CH₂ | CH₃ | CH₂ | 2-Cl—C₆H₄ |
| 1.95 | C(CH₃)₃ | C(CH₃)₂—CH₂ | CH₃ | CH₂ | 2-CH₃—C₆H₄ |
| 1.96 | C(CH₃)₃ | C(CH₃)₂—CH₂ | CH₃ | CH₂ | 2-CH₃O—C₆H₄ |
| 1.97 | C(CH₃)₃ | C(CH₃)₂—CH₂ | CH₃ | CH₂ | 2-CN—C₆H₄ |
| 1.98 | C(CH₃)₃ | C(CH₃)₂—CH₂ | CH₃ | CH₂ | 3,4-(CH₃O)₂C₆H₃ |
| 1.99 | C(CH₃)₃ | C(CH₃)₂—CH₂ | CH₃ | CH₂ | 2,4-Cl₂—C₆H₃ |
| 1.100 | C(CH₃)₃ | C(CH₃)₂—CH₂ | CH₃ | CH₂ | 2,4-(CH₃)₂—C₆H₃ |
| 1.101 | C(CH₃)₃ | C(CH₃)₂—CH₂ | CH₃ | CH₂ | 3,4-(CH₃)₂C₆H₃ |
| 1.102 | C(CH₃)₃ | C(CH₃)₂—CH₂ | CH₃ | CH₂ | 4-NO₂—C₆H₄ |
| 1.103 | CH(CH₃)₂ | CH(CH₃) | H | CH₂ | 4-Cl—C₆H₄ |
| 1.104 | CH(CH₃)₂ | CH(CH₃) | H | CH₂ | 4-CH₃—C₆H₄ |
| 1.105 | CH(CH₃)₂ | CH(CH₃) | H | CH₂ | 4-CH₃O—C₆H₄ |
| 1.106 | CH(CH₃)₂ | CH(CH₃) | H | CH₂ | 4-CN—C₆H₄ |
| 1.107 | CH(CH₃)₂ | CH(CH₃) | H | CH₂ | 3-Cl—C₆H₄ |
| 1.108 | CH(CH₃)₂ | CH(CH₃) | H | CH₂ | 3-CH₃—C₆H₄ |
| 1.109 | CH(CH₃)₂ | CH(CH₃) | H | CH₂ | 3-CH₃O—C₆H₄ |
| 1.110 | CH(CH₃)₂ | CH(CH₃) | H | CH₂ | 3-CN—C₆H₄ |
| 1.111 | CH(CH₃)₂ | CH(CH₃) | H | CH₂ | 2-Cl—C₆H₄ |
| 1.112 | CH(CH₃)₂ | CH(CH₃) | H | CH₂ | 2-CH₃—C₆H₄ |
| 1.113 | CH(CH₃)₂ | CH(CH₃) | H | CH₂ | 2-CH₃O—C₆H₄ |
| 1.114 | CH(CH₃)₂ | CH(CH₃) | H | CH₂ | 2-CN—C₆H₄ |
| 1.115 | CH(CH₃)₂ | CH(CH₃) | H | CH₂ | 3,4-(CH₃O)₂C₆H₃ |
| 1.116 | CH(CH₃)₂ | CH(CH₃) | H | CH₂ | 2,4-Cl₂—C₆H₃ |
| 1.117 | CH(CH₃)₂ | CH(CH₃) | H | CH₂ | 2,4-(CH₃)₂—C₆H₃ |
| 1.118 | CH(CH₃)₂ | CH(CH₃) | H | CH₂ | 3,4-(CH₃)₂C₆H₃ |
| 1.119 | CH(CH₃)₂ | CH(CH₃) | H | CH₂ | 4-NO₂—C₆H₄ |
| 1.120 | CH(CH₃)C₂H₅ | CH(CH₃) | H | CH₂ | 4-Cl—C₆H₄ |
| 1.121 | CH(CH₃)C₂H₅ | CH(CH₃) | H | CH₂ | 4-CH₃—C₆H₄ |
| 1.122 | CH(CH₃)C₂H₅ | CH(CH₃) | H | CH₂ | 4-CH₃O—C₆H₄ |
| 1.123 | CH(CH₃)C₂H₅ | CH(CH₃) | H | CH₂ | 4-CN—C₆H₄ |
| 1.124 | CH(CH₃)C₂H₅ | CH(CH₃) | H | CH₂ | 3-Cl—C₆H₄ |
| 1.125 | CH(CH₃)C₂H₅ | CH(CH₃) | H | CH₂ | 3-CH₃—C₆H₄ |
| 1.126 | CH(CH₃)C₂H₅ | CH(CH₃) | H | CH₂ | 3-CH₃O—C₆H₄ |
| 1.127 | CH(CH₃)C₂H₅ | CH(CH₃) | H | CH₂ | 3-CN—C₆H₄ |
| 1.128 | CH(CH₃)C₂H₅ | CH(CH₃) | H | CH₂ | 2-Cl—C₆H₄ |
| 1.129 | CH(CH₃)C₂H₅ | CH(CH₃) | H | CH₂ | 2-CH₃—C₆H₄ |
| 1.130 | CH(CH₃)C₂H₅ | CH(CH₃) | H | CH₂ | 2-CH₃O—C₆H₄ |
| 1.131 | CH(CH₃)C₂H₅ | CH(CH₃) | H | CH₂ | 2-CN—C₆H₄ |
| 1.132 | CH(CH₃)C₂H₅ | CH(CH₃) | H | CH₂ | 3,4-(CH₃O)₂C₆H₃ |
| 1.133 | CH(CH₃)C₂H₅ | CH(CH₃) | H | CH₂ | 2,4-Cl₂—C₆H₃ |
| 1.134 | CH(CH₃)C₂H₅ | CH(CH₃) | H | CH₂ | 2,4-(CH₃)₂—C₆H₃ |
| 1.135 | CH(CH₃)C₂H₅ | CH(CH₃) | H | CH₂ | 3,4-(CH₃)₂C₆H₃ |
| 1.136 | CH(CH₃)C₂H₅ | CH(CH₃) | H | CH₂ | 4-NO₂—C₆H₄ |
| 1.137 | C(CH₃)₃ | CH(CH₃) | H | CH₂ | 4-Cl—C₆H₄ |
| 1.138 | C(CH₃)₃ | CH(CH₃) | H | CH₂ | 4-CH₃—C₆H₄ |

TABLE A-continued $$R^1-O-\overset{O}{\underset{S}{C}}-NH-\overset{CH(CH_3)_2}{\underset{}{CH}}-\overset{O}{C}-NH-A-\overset{Y}{\underset{}{C}}=N-O-Z-Ar \quad (I')$$

| No. | R¹ | A | Y | Z | Ar |
|---|---|---|---|---|---|
| 1.139 | C(CH₃)₃ | CH(CH₃) | H | CH₂ | 4-CH₃O—C₆H₄ |
| 1.140 | C(CH₃)₃ | CH(CH₃) | H | CH₂ | 4-CN—C₆H₄ |
| 1.141 | C(CH₃)₃ | CH(CH₃) | H | CH₂ | 3-Cl—C₆H₄ |
| 1.142 | C(CH₃)₃ | CH(CH₃) | H | CH₂ | 3-CH₃—C₆H₄ |
| 1.143 | C(CH₃)₃ | CH(CH₃) | H | CH₂ | 3-CH₃O—C₆H₄ |
| 1.144 | C(CH₃)₃ | CH(CH₃) | H | CH₂ | 3-CN—C₆H₄ |
| 1.145 | C(CH₃)₃ | CH(CH₃) | H | CH₂ | 2-Cl—C₆H₄ |
| 1.146 | C(CH₃)₃ | CH(CH₃) | H | CH₂ | 2-CH₃—C₆H₄ |
| 1.147 | C(CH₃)₃ | CH(CH₃) | H | CH₂ | 2-CH₃C—C₆H₄ |
| 1.148 | C(CH₃)₃ | CH(CH₃) | H | CH₂ | 2-CN—C₆H₄ |
| 1.149 | C(CH₃)₃ | CH(CH₃) | H | CH₂ | 3,4-(CH₃O)₂C₆H₃ |
| 1.150 | C(CH₃)₃ | CH(CH₃) | H | CH₂ | 2,4-Cl₂—C₆H₃ |
| 1.151 | C(CH₃)₃ | CH(CH₃) | H | CH₂ | 2,4-(CH₃)₂—C₆H₃ |
| 1.152 | C(CH₃)₃ | CH(CH₃) | H | CH₂ | 3,4-(CH₃)₂C₆H₃ |
| 1.153 | C(CH₃)₃ | CH(CH₃) | H | CH₂ | 4-NO₂—C₆H₄ |
| 1.154 | CH(CH₃)₂ | C(CH₃)₂—CH₂ | H | CH₂ | 4-Cl—C₆H₄ |
| 1.155 | CH(CH₃)₂ | C(CH₃)₂—CH₂ | H | CH₂ | 4-CH₃—C₆H₄ |
| 1.156 | CH(CH₃)₂ | C(CH₃)₂—CH₂ | H | CH₂ | 4-CH₃O—C₆H₄ |
| 1.157 | CH(CH₃)₂ | C(CH₃)₂—CH₂ | H | CH₂ | 4-CN—C₆H₄ |
| 1.158 | CH(CH₃)₂ | C(CH₃)₂—CH₂ | H | CH₂ | 3-Cl—C₆H₄ |
| 1.159 | CH(CH₃)₂ | C(CH₃)₂—CH₂ | H | CH₂ | 3-CH₃—C₆H₄ |
| 1.160 | CH(CH₃)₂ | C(CH₃)₂—CH₂ | H | CH₂ | 3-CH₃O—C₆H₄ |
| 1.161 | CH(CH₃)₂ | C(CH₃)₂—CH₂ | H | CH₂ | 3-CN—C₆H₄ |
| 1.162 | CH(CH₃)₂ | C(CH₃)₂—CH₂ | H | CH₂ | 2-Cl—C₆H₄ |
| 1.163 | CH(CH₃)₂ | C(CH₃)₂—CH₂ | H | CH₂ | 2-CH₃—C₆H₄ |
| 1.164 | CH(CH₃)₂ | C(CH₃)₂—CH₂ | H | CH₂ | 2-CH₃O—C₆H₄ |
| 1.165 | CH(CH₃)₂ | C(CH₃)₂—CH₂ | H | CH₂ | 2-CN—C₆H₄ |
| 1.166 | CH(CH₃)₂ | C(CH₃)₂—CH₂ | H | CH₂ | 3,4-(CH₃O)₂C₆H₃ |
| 1.167 | CH(CH₃)₂ | C(CH₃)₂—CH₂ | H | CH₂ | 2,4-Cl₂—C₆H₃ |
| 1.168 | CH(CH₃)₂ | C(CH₃)₂—CH₂ | H | CH₂ | 2,4-(CH₃)₂—C₆H₃ |
| 1.169 | CH(CH₃)₂ | C(CH₃)₂—CH₂ | H | CH₂ | 3,4-(CH₃)₂C₆H₃ |
| 1.170 | CH(CH₃)₂ | C(CH₃)₂—CH₂ | H | CH₂ | 4-NO₂—C₆H₄ |
| 1.171 | CH(CH₃)C₂H₅ | C(CH₃)₂—CH₂ | H | CH₂ | 4-Cl—C₆H₄ |
| 1.172 | CH(CH₃)C₂H₅ | C(CH₃)₂—CH₂ | H | CH₂ | 4-CH₃—C₆H₄ |
| 1.173 | CH(CH₃)C₂H₅ | C(CH₃)₂—CH₂ | H | CH₂ | 4-CH₃O—C₆H₄ |
| 1.174 | CH(CH₃)C₂H₅ | C(CH₃)₂—CH₂ | H | CH₂ | 4-CN—C₆H₄ |
| 1.175 | CH(CH₃)C₂H₅ | C(CH₃)₂—CH₂ | H | CH₂ | 3-Cl—C₆H₄ |
| 1.176 | CH(CH₃)C₂H₅ | C(CH₃)₂—CH₂ | H | CH₂ | 3-CH₃—C₆H₄ |
| 1.177 | CH(CH₃)C₂H₅ | C(CH₃)₂—CH₂ | H | CH₂ | 3-CH₃O—C₆H₄ |
| 1.178 | CH(CH₃)C₂H₅ | C(CH₃)₂—CH₂ | H | CH₂ | 3-CN—C₆H₄ |
| 1.179 | CH(CH₃)C₂H₅ | C(CH₃)₂—CH₂ | H | CH₂ | 2-Cl—C₆H₄ |
| 1.180 | CH(CH₃)C₂H₅ | C(CH₃)₂—CH₂ | H | CH₂ | 2-CH₃—C₆H₄ |
| 1.181 | CH(CH₃)C₂H₅ | C(CH₃)₂—CH₂ | H | CH₂ | 2-CH₃O—C₆H₄ |
| 1.182 | CH(CH₃)C₂H₅ | C(CH₃)₂—CH₂ | H | CH₂ | 2-CN—C₆H₄ |
| 1.183 | CH(CH₃)C₂H₅ | C(CH₃)₂—CH₂ | H | CH₂ | 3,4-(CH₃O)₂C₆H₃ |
| 1.184 | CH(CH₃)C₂H₅ | C(CH₃)₂—CH₂ | H | CH₂ | 2,4-Cl₂—C₆H₃ |
| 1.185 | CH(CH₃)C₂H₅ | C(CH₃)₂—CH₂ | H | CH₂ | 2,4-(CH₃)₂—C₆H₃ |
| 1.186 | CH(CH₃)C₂H₅ | C(CH₃)₂—CH₂ | H | CH₂ | 3,4-(CH₃)₂C₆H₃ |
| 1.187 | CH(CH₃)C₂H₅ | C(CH₃)₂—CH₂ | H | CH₂ | 4-NO₂—C₆H₄ |
| 1.188 | C(CH₃)₃ | C(CH₃)₂—CH₂ | H | CH₂ | 4-Cl—C₆H₄ |
| 1.189 | C(CH₃)₃ | C(CH₃)₂—CH₂ | H | CH₂ | 4-CH₃—C₆H₄ |
| 1.190 | C(CH₃)₃ | C(CH₃)₂—CH₂ | H | CH₂ | 4-CH₃O—C₆H₄ |
| 1.191 | C(CH₃)₃ | C(CH₃)₂—CH₂ | H | CH₂ | 4-CN—C₆H₄ |
| 1.192 | C(CH₃)₃ | C(CH₃)₂—CH₂ | H | CH₂ | 3-Cl—C₆H₄ |
| 1.193 | C(CH₃)₃ | C(CH₃)₂—CH₂ | H | CH₂ | 3-CH₃—C₆H₄ |
| 1.194 | C(CH₃)₃ | C(CH₃)₂—CH₂ | H | CH₂ | 3-CH₃O—C₆H₄ |
| 1.195 | C(CH₃)₃ | C(CH₃)₂—CH₂ | H | CH₂ | 3-CN—C₆H₄ |
| 1.196 | C(CH₃)₃ | C(CH₃)₂—CH₂ | H | CH₂ | 2-Cl—C₆H₄ |
| 1.197 | C(CH₃)₃ | C(CH₃)₂—CH₂ | H | CH₂ | 2-CH₃—C₆H₄ |
| 1.198 | C(CH₃)₃ | C(CH₃)₂—CH₂ | H | CH₂ | 2-CH₃O—C₆H₄ |
| 1.199 | C(CH₃)₃ | C(CH₃)₂—CH₂ | H | CH₂ | 2-CN—C₆H₄ |
| 1.200 | C(CH₃)₃ | C(CH₃)₂—CH₂ | H | CH₂ | 3,4-(CH₃O)₂C₆H₃ |
| 1.201 | C(CH₃)₃ | C(CH₃)₂—CH₂ | H | CH₂ | 2,4-Cl₂—C₆H₃ |
| 1.202 | C(CH₃)₃ | C(CH₃)₂—CH₂ | H | CH₂ | 2,4-(CH₃)₂—C₆H₃ |
| 1.203 | C(CH₃)₃ | C(CH₃)₂—CH₂ | H | CH₂ | 3,4-(CH₃)₂C₆H₃ |
| 1.204 | C(CH₃)₃ | C(CH₃)₂—CH₂ | H | CH₂ | 4-NO₂—C₆H₄ |
| 1.205 | CH(CH₃)₂ | CH₂ | CH₃ | CH₂ | 4-Cl—C₆H₄ |
| 1.206 | CH(CH₃)₂ | CH₂ | CH₃ | CH₂ | 4-CH₃—C₆H₄ |
| 1.207 | CH(CH₃)₂ | CH₂ | CH₃ | CH₂ | 4-CH₃O—C₆H₄ |
| 1.208 | CH(CH₃)₂ | CH₂ | CH₃ | CH₂ | 4-CN—C₆H₄ |

TABLE A-continued $$R^1-O-\overset{O}{\underset{}{C}}-NH-\overset{CH(CH_3)_2}{\underset{S}{CH}}-\overset{O}{\underset{}{C}}-NH-A-\overset{Y}{\underset{}{C}}=N-O-Z-Ar \qquad (I')$$

| No. | R¹ | A | Y | Z | Ar |
|---|---|---|---|---|---|
| 1.209 | $CH(CH_3)_2$ | $CH_2$ | $CH_3$ | $CH_2$ | 3-Cl—$C_6H_4$ |
| 1.210 | $CH(CH_3)_2$ | $CH_2$ | $CH_3$ | $CH_2$ | 3-$CH_3$—$C_6H_4$ |
| 1.211 | $CH(CH_3)_2$ | $CH_2$ | $CH_3$ | $CH_2$ | 3-$CH_3$O—$C_6H_4$ |
| 1.212 | $CH(CH_3)_2$ | $CH_2$ | $CH_3$ | $CH_2$ | 3-CN—$C_6H_4$ |
| 1.213 | $CH(CH_3)_2$ | $CH_2$ | $CH_3$ | $CH_2$ | 2-Cl—$C_6H_4$ |
| 1.214 | $CH(CH_3)_2$ | $CH_2$ | $CH_3$ | $CH_2$ | 2-$CH_3$—$C_6H_4$ |
| 1.215 | $CH(CH_3)_2$ | $CH_2$ | $CH_3$ | $CH_2$ | 2-$CH_3$O—$C_6H_4$ |
| 1.216 | $CH(CH_3)_2$ | $CH_2$ | $CH_3$ | $CH_2$ | 2-CN—$C_6H_4$ |
| 1.217 | $CH(CH_3)_2$ | $CH_2$ | $CH_3$ | $CH_2$ | 3,4-$(CH_3O)_2C_6H_3$ |
| 1.218 | $CH(CH_3)_2$ | $CH_2$ | $CH_3$ | $CH_2$ | 2,4-$Cl_2$—$C_6H_3$ |
| 1.219 | $CH(CH_3)_2$ | $CH_2$ | $CH_3$ | $CH_2$ | 2,4-$(CH_3)_2$—$C_6H_3$ |
| 1.220 | $CH(CH_3)_2$ | $CH_2$ | $CH_3$ | $CH_2$ | 3,4-$(CH_3)_2C_6H_3$ |
| 1.221 | $CH(CH_3)_2$ | $CH_2$ | $CH_3$ | $CH_2$ | 4-$NO_2$—$C_6H_4$ |
| 1.222 | $CH(CH_3)C_2H_5$ | $CH_2$ | $CH_3$ | $CH_2$ | 4-Cl—$C_6H_4$ |
| 1.223 | $CH(CH_3)C_2H_5$ | $CH_2$ | $CH_3$ | $CH_2$ | 4-$CH_3$—$C_6H_4$ |
| 1.224 | $CH(CH_3)C_2H_5$ | $CH_2$ | $CH_3$ | $CH_2$ | 4-$CH_3$O—$C_6H_4$ |
| 1.225 | $CH(CH_3)C_2H_5$ | $CH_2$ | $CH_3$ | $CH_2$ | 4-CN—$C_6H_4$ |
| 1.226 | $CH(CH_3)C_2H_5$ | $CH_2$ | $CH_3$ | $CH_2$ | 3-Cl—$C_6H_4$ |
| 1.227 | $CH(CH_3)C_2H_5$ | $CH_2$ | $CH_3$ | $CH_2$ | 3-$CH_3$—$C_6H_4$ |
| 1.228 | $CH(CH_3)C_2H_5$ | $CH_2$ | $CH_3$ | $CH_2$ | 3-$CH_3$O—$C_6H_4$ |
| 1.229 | $CH(CH_3)C_2H_5$ | $CH_2$ | $CH_3$ | $CH_2$ | 3-CN—$C_6H_4$ |
| 1.230 | $CH(CH_3)C_2H_5$ | $CH_2$ | $CH_3$ | $CH_2$ | 2-Cl—$C_6H_4$ |
| 1.231 | $CH(CH_3)C_2H_5$ | $CH_2$ | $CH_3$ | $CH_2$ | 2-$CH_3$—$C_6H_4$ |
| 1.232 | $CH(CH_3)C_2H_5$ | $CH_2$ | $CH_3$ | $CH_2$ | 2-$CH_3$O—$C_6H_4$ |
| 1.233 | $CH(CH_3)C_2H_5$ | $CH_2$ | $CH_3$ | $CH_2$ | 2-CN—$C_6H_4$ |
| 1.234 | $CH(CH_3)C_2H_5$ | $CH_2$ | $CH_3$ | $CH_2$ | 3,4-$(CH_3O)_2C_6H_3$ |
| 1.235 | $CH(CH_3)C_2H_5$ | $CH_2$ | $CH_3$ | $CH_2$ | 2,4-$Cl_2$—$C_6H_3$ |
| 1.236 | $CH(CH_3)C_2H_5$ | $CH_2$ | $CH_3$ | $CH_2$ | 2,4-$(CH_3)_2$—$C_6H_3$ |
| 1.237 | $CH(CH_3)C_2H_5$ | $CH_2$ | $CH_3$ | $CH_2$ | 3,4-$(CH_3)_2C_6H_3$ |
| 1.238 | $CH(CH_3)C_2H_5$ | $CH_2$ | $CH_3$ | $CH_2$ | 4-$NO_2$—$C_6H_4$ |
| 1.239 | $C(CH_3)_3$ | $CH_2$ | $CH_3$ | $CH_2$ | 4-Cl—$C_6H_4$ |
| 1.240 | $C(CH_3)_3$ | $CH_2$ | $CH_3$ | $CH_2$ | 4-$CH_3$—$C_6H_4$ |
| 1.241 | $C(CH_3)_3$ | $CH_2$ | $CH_3$ | $CH_2$ | 4-$CH_3$O—$C_6H_4$ |
| 1.242 | $C(CH_3)_3$ | $CH_2$ | $CH_3$ | $CH_2$ | 4-CN—$C_6H_4$ |
| 1.243 | $C(CH_3)_3$ | $CH_2$ | $CH_3$ | $CH_2$ | 3-Cl—$C_6H_4$ |
| 1.244 | $C(CH_3)_3$ | $CH_2$ | $CH_3$ | $CH_2$ | 3-$CH_3$—$C_6H_4$ |
| 1.245 | $C(CH_3)_3$ | $CH_2$ | $CH_3$ | $CH_2$ | 3-$CH_3$O—$C_6H_4$ |
| 1.246 | $C(CH_3)_3$ | $CH_2$ | $CH_3$ | $CH_2$ | 3-CN—$C_6H_4$ |
| 1.247 | $C(CH_3)_3$ | $CH_2$ | $CH_3$ | $CH_2$ | 2-Cl—$C_6H_4$ |
| 1.248 | $C(CH_3)_3$ | $CH_2$ | $CH_3$ | $CH_2$ | 2-$CH_3$—$C_6H_4$ |
| 1.249 | $C(CH_3)_3$ | $CH_2$ | $CH_3$ | $CH_2$ | 2-$CH_3$O—$C_6H_4$ |
| 1.250 | $C(CH_3)_3$ | $CH_2$ | $CH_3$ | $CH_2$ | 2-CN—$C_6H_4$ |
| 1.251 | $C(CH_3)_3$ | $CH_2$ | $CH_3$ | $CH_2$ | 3,4-$(CH_3O)_2C_6H_3$ |
| 1.252 | $C(CH_3)_3$ | $CH_2$ | $CH_3$ | $CH_2$ | 2,4-$Cl_2$—$C_6H_3$ |
| 1.253 | $C(CH_3)_3$ | $CH_2$ | $CH_3$ | $CH_2$ | 2,4-$(CH_3)_2$—$C_6H_3$ |
| 1.254 | $C(CH_3)_3$ | $CH_2$ | $CH_3$ | $CH_2$ | 3,4-$(CH_3)_2C_6H_3$ |
| 1.255 | $C(CH_3)_3$ | $CH_2$ | $CH_3$ | $CH_2$ | 4-$NO_2$—$C_6H_4$ |
| 1.256 | $CH(CH_3)_2$ | $CH_2$ | H | $CH_2$ | 4-Cl—$C_6H_4$ |
| 1.257 | $CH(CH_3)_2$ | $CH_2$ | H | $CH_2$ | 4-$CH_3$—$C_6H_4$ |
| 1.258 | $CH(CH_3)_2$ | $CH_2$ | H | $CH_2$ | 4-$CH_3$O—$C_6H_4$ |
| 1.259 | $CH(CH_3)_2$ | $CH_2$ | H | $CH_2$ | 4-CN—$C_6H_4$ |
| 1.260 | $CH(CH_3)_2$ | $CH_2$ | H | $CH_2$ | 3-Cl—$C_6H_4$ |
| 1.261 | $CH(CH_3)_2$ | $CH_2$ | H | $CH_2$ | 3-$CH_3$—$C_6H_4$ |
| 1.262 | $CH(CH_3)_2$ | $CH_2$ | H | $CH_2$ | 3-$CH_3$O—$C_6H_4$ |
| 1.263 | $CH(CH_3)_2$ | $CH_2$ | H | $CH_2$ | 3-CN—$C_6H_4$ |
| 1.264 | $CH(CH_3)_2$ | $CH_2$ | H | $CH_2$ | 2-Cl—$C_6H_4$ |
| 1.265 | $CH(CH_3)_2$ | $CH_2$ | H | $CH_2$ | 2-$CH_3$—$C_6H_4$ |
| 1.266 | $CH(CH_3)_2$ | $CH_2$ | H | $CH_2$ | 2-$CH_3$O—$C_6H_4$ |
| 1.267 | $CH(CH_3)_2$ | $CH_2$ | H | $CH_2$ | 2-CN—$C_6H_4$ |
| 1.268 | $CH(CH_3)_2$ | $CH_2$ | H | $CH_2$ | 3,4-$(CH_3O)_2C_6H_3$ |
| 1.269 | $CH(CH_3)_2$ | $CH_2$ | H | $CH_2$ | 2,4-$Cl_2$—$C_6H_3$ |
| 1.270 | $CH(CH_3)_2$ | $CH_2$ | H | $CH_2$ | 2,4-$(CH_3)_2$—$C_6H_3$ |
| 1.271 | $CH(CH_3)_2$ | $CH_2$ | H | $CH_2$ | 3,4-$(CH_3)_2C_6H_3$ |
| 1.272 | $CH(CH_3)_2$ | $CH_2$ | H | $CH_2$ | 4-$NO_2$—$C_6H_4$ |
| 1.273 | $CH(CH_3)C_2H_5$ | $CH_2$ | H | $CH_2$ | 4-Cl—$C_6H_4$ |
| 1.274 | $CH(CH_3)C_2H_5$ | $CH_2$ | H | $CH_2$ | 4-$CH_3$—$C_6H_4$ |
| 1.275 | $CH(CH_3)C_2H_5$ | $CH_2$ | H | $CH_2$ | 4-$CH_3$O—$C_6H_4$ |
| 1.276 | $CH(CH_3)C_2H_5$ | $CH_2$ | H | $CH_2$ | 4-CN—$C_6H_4$ |
| 1.277 | $CH(CH_3)C_2H_5$ | $CH_2$ | H | $CH_2$ | 3-Cl—$C_6H_4$ |
| 1.278 | $CH(CH_3)C_2H_5$ | $CH_2$ | H | $CH_2$ | 3-$CH_3$—$C_6H_4$ |

TABLE A-continued $$R^1-O-\overset{O}{\underset{}{C}}-NH-\overset{CH(CH_3)_2}{\underset{S}{CH}}-\overset{O}{\underset{}{C}}-NH-A-\overset{Y}{\underset{}{C}}=N-O-Z-Ar \quad (I')$$

| No. | R¹ | A | Y | Z | Ar |
|---|---|---|---|---|---|
| 1.279 | CH(CH₃)C₂H₅ | CH₂ | H | CH₂ | 3-CH₃O—C₆H₄ |
| 1.280 | CH(CH₃)C₂H₅ | CH₂ | H | CH₂ | 3-CN—C₆H₄ |
| 1.281 | CH(CH₃)C₂H₅ | CH₂ | H | CH₂ | 2-Cl—C₆H₄ |
| 1.282 | CH(CH₃)C₂H₅ | CH₂ | H | CH₂ | 2-CH₃—C₆H₄ |
| 1.283 | CH(CH₃)C₂H₅ | CH₂ | H | CH₂ | 2-CH₃O—C₆H₄ |
| 1.284 | CH(CH₃)C₂H₅ | CH₂ | H | CH₂ | 2-CN—C₆H₄ |
| 1.285 | CH(CH₃)C₂H₅ | CH₂ | H | CH₂ | 3,4-(CH₃O)₂C₆H₃ |
| 1.286 | CH(CH₃)C₂H₅ | CH₂ | H | CH₂ | 2,4-Cl₂—C₆H₃ |
| 1.287 | CH(CH₃)C₂H₅ | CH₂ | H | CH₂ | 2,4-(CH₃)₂—C₆H₃ |
| 1.288 | CH(CH₃)C₂H₅ | CH₂ | H | CH₂ | 3,4-(CH₃)₂C₆H₃ |
| 1.289 | CH(CH₃)C₂H₅ | CH₂ | H | CH₂ | 4-NO₂—C₆H₄ |
| 1.290 | C(CH₃)₃ | CH₂ | H | CH₂ | 4-Cl—C₆H₄ |
| 1.291 | C(CH₃)₃ | CH₂ | H | CH₂ | 4-CH₃—C₆H₄ |
| 1.292 | C(CH₃)₃ | CH₂ | H | CH₂ | 4-CH₃O—C₆H₄ |
| 1.293 | C(CH₃)₃ | CH₂ | H | CH₂ | 4-CN—C₆H₄ |
| 1.294 | C(CH₃)₃ | CH₂ | H | CH₂ | 3-Cl—C₆H₄ |
| 1.295 | C(CH₃)₃ | CH₂ | H | CH₂ | 3-CH₃—C₆H₄ |
| 1.296 | C(CH₃)₃ | CH₂ | H | CH₂ | 3-CH₃O—C₆H₄ |
| 1.297 | C(CH₃)₃ | CH₂ | H | CH₂ | 3-CN—C₆H₄ |
| 1.298 | C(CH₃)₃ | CH₂ | H | CH₂ | 2-Cl—C₆H₄ |
| 1.299 | C(CH₃)₃ | CH₂ | H | CH₂ | 2-CH₃—C₆H₄ |
| 1.300 | C(CH₃)₃ | CH₂ | H | CH₂ | 2-CH₃O—C₆H₄ |
| 1.301 | C(CH₃)₃ | CH₂ | H | CH₂ | 2-CN—C₆H₄ |
| 1.302 | C(CH₃)₃ | CH₂ | H | CH₂ | 3,4-(CH₃O)₂C₆H₃ |
| 1.303 | C(CH₃)₃ | CH₂ | H | CH₂ | 2,4-Cl₂—C₆H₃ |
| 1.304 | C(CH₃)₃ | CH₂ | H | CH₂ | 2,4-(CH₃)₂—C₆H₃ |
| 1.305 | C(CH₃)₃ | CH₂ | H | CH₂ | 3,4-(CH₃)₂C₆H₃ |
| 1.306 | C(CH₃)₃ | CH₂ | H | CH₂ | 4-NO₂—C₆H₄ |
| 1.307 | CH(CH₃)₂ | CH(CH₃) | CH₃ | CH₂CH₂ | 4-Cl—C₆H₄ |
| 1.308 | CH(CH₃)₂ | CH(CH₃) | CH₃ | CH₂CH₂ | 4-CH₃—C₆H₄ |
| 1.309 | CH(CH₃)₂ | CH(CH₃) | CH₃ | CH₂CH₂ | 4-CH₃O—C₆H₄ |
| 1.310 | CH(CH₃)₂ | CH(CH₃) | CH₃ | CH₂CH₂ | 4-CN—C₆H₄ |
| 1.311 | CH(CH₃)₂ | CH(CH₃) | CH₃ | CH₂CH₂ | 3-Cl—C₆H₄ |
| 1.312 | CH(CH₃)₂ | CH(CH₃) | CH₃ | CH₂CH₂ | 3-CH₃—C₆H₄ |
| 1.313 | CH(CH₃)₂ | CH(CH₃) | CH₃ | CH₂CH₂ | 3-CH₃O—C₆H₄ |
| 1.314 | CH(CH₃)₂ | CH(CH₃) | CH₃ | CH₂CH₂ | 3-CN—C₆H₄ |
| 1.315 | CH(CH₃)₂ | CH(CH₃) | CH₃ | CH₂CH₂ | 2-Cl—C₆H₄ |
| 1.316 | CH(CH₃)₂ | CH(CH₃) | CH₃ | CH₂CH₂ | 2-CH₃—C₆H₄ |
| 1.317 | CH(CH₃)₂ | CH(CH₃) | CH₃ | CH₂CH₂ | 2-CH₃O—C₆H₄ |
| 1.318 | CH(CH₃)₂ | CH(CH₃) | CH₃ | CH₂CH₂ | 2-CN—C₆H₄ |
| 1.319 | CH(CH₃)₂ | CH(CH₃) | CH₃ | CH₂CH₂ | 3,4-(CH₃O)₂C₆H₃ |
| 1.320 | CH(CH₃)₂ | CH(CH₃) | CH₃ | CH₂CH₂ | 2,4-Cl₂—C₆H₃ |
| 1.321 | CH(CH₃)₂ | CH(CH₃) | CH₃ | CH₂CH₂ | 2,4-(CH₃)₂—C₆H₃ |
| 1.322 | CH(CH₃)₂ | CH(CH₃) | CH₃ | CH₂CH₂ | 3,4-(CH₃)₂C₆H₃ |
| 1.323 | CH(CH₃)₂ | CH(CH₃) | CH₃ | CH₂CH₂ | 4-NO₂—C₆H₄ |
| 1.324 | CH(CH₃)C₂H₅ | CH(CH₃) | CH₃ | CH₂CH₂ | 4-Cl—C₆H₄ |
| 1.325 | CH(CH₃)C₂H₅ | CH(CH₃) | CH₃ | CH₂CH₂ | 4-CH₃—C₆H₄ |
| 1.326 | CH(CH₃)C₂H₅ | CH(CH₃) | CH₃ | CH₂CH₂ | 4-CH₃O—C₆H₄ |
| 1.327 | CH(CH₃)C₂H₅ | CH(CH₃) | CH₃ | CH₂CH₂ | 4-CN—C₆H₄ |
| 1.328 | CH(CH₃)C₂H₅ | CH(CH₃) | CH₃ | CH₂CH₂ | 3-Cl—C₆H₄ |
| 1.329 | CH(CH₃)C₂H₅ | CH(CH₃) | CH₃ | CH₂CH₂ | 3-CH₃—C₆H₄ |
| 1.330 | CH(CH₃)C₂H₅ | CH(CH₃) | CH₃ | CH₂CH₂ | 3-CH₃O—C₆H₄ |
| 1.331 | CH(CH₃)C₂H₅ | CH(CH₃) | CH₃ | CH₂CH₂ | 3-CN—C₆H₄ |
| 1.332 | CH(CH₃)C₂H₅ | CH(CH₃) | CH₃ | CH₂CH₂ | 2-Cl—C₆H₄ |
| 1.333 | CH(CH₃)C₂H₅ | CH(CH₃) | CH₃ | CH₂CH₂ | 2-CH₃—C₆H₄ |
| 1.334 | CH(CH₃)C₂H₅ | CH(CH₃) | CH₃ | CH₂CH₂ | 2-CH₃O—C₆H₄ |
| 1.335 | CH(CH₃)C₂H₅ | CH(CH₃) | CH₃ | CH₂CH₂ | 2-CN—C₆H₄ |
| 1.336 | CH(CH₃)C₂H₅ | CH(CH₃) | CH₃ | CH₂CH₂ | 3,4-(CH₃O)₂C₆H₃ |
| 1.337 | CH(CH₃)C₂H₅ | CH(CH₃) | CH₃ | CH₂CH₂ | 2,4-Cl₂—C₆H₃ |
| 1.338 | CH(CH₃)C₂H₅ | CH(CH₃) | CH₃ | CH₂CH₂ | 2,4-(CH₃)₂—C₆H₃ |
| 1.339 | CH(CH₃)C₂H₅ | CH(CH₃) | CH₃ | CH₂CH₂ | 3,4-(CH₃)₂C₆H₃ |
| 1.340 | CH(CH₃)C₂H₅ | CH(CH₃) | CH₃ | CH₂CH₂ | 4-NO₂—C₆H₄ |
| 1.341 | C(CH₃)₃ | CH(CH₃) | CH₃ | CH₂CH₂ | 4-Cl—C₆H₄ |
| 1.342 | C(CH₃)₃ | CH(CH₃) | CH₃ | CH₂CH₂ | 4-CH₃—C₆H₄ |
| 1.343 | C(CH₃)₃ | CH(CH₃) | CH₃ | CH₂CH₂ | 4-CH₃O—C₆H₄ |
| 1.344 | C(CH₃)₃ | CH(CH₃) | CH₃ | CH₂CH₂ | 4-CN—C₆H₄ |
| 1.345 | C(CH₃)₃ | CH(CH₃) | CH₃ | CH₂CH₂ | 3-Cl—C₆H₄ |
| 1.346 | C(CH₃)₃ | CH(CH₃) | CH₃ | CH₂CH₂ | 3-CH₃—C₆H₄ |
| 1.347 | C(CH₃)₃ | CH(CH₃) | CH₃ | CH₂CH₂ | 3-CH₃O—C₆H₄ |
| 1.348 | C(CH₃)₃ | CH(CH₃) | CH₃ | CH₂CH₂ | 3-CN—C₆H₄ |

TABLE A-continued $$R^1-O-\overset{O}{C}-NH-\overset{CH(CH_3)_2}{\underset{S}{CH}}-\overset{O}{C}-NH-A-\overset{Y}{C}=N-O-Z-Ar \quad (I')$$

| No. | R¹ | A | Y | Z | Ar |
|---|---|---|---|---|---|
| 1.349 | C(CH₃)₃ | CH(CH₃) | CH₃ | CH₂CH₂ | 2-Cl—C₆H₄ |
| 1.350 | C(CH₃)₃ | CH(CH₃) | CH₃ | CH₂CH₂ | 2-CH₃—C₆H₄ |
| 1.351 | C(CH₃)₃ | CH(CH₃) | CH₃ | CH₂CH₂ | 2-CH₃O—C₆H₄ |
| 1.352 | C(CH₃)₃ | CH(CH₃) | CH₃ | CH₂CH₂ | 2-CN—C₆H₄ |
| 1.353 | C(CH₃)₃ | CH(CH₃) | CH₃ | CH₂CH₂ | 3,4-(CH₃O)₂C₆H₃ |
| 1.354 | C(CH₃)₃ | CH(CH₃) | CH₃ | CH₂CH₂ | 2,4-Cl₂—C₆H₃ |
| 1.355 | C(CH₃)₃ | CH(CH₃) | CH₃ | CH₂CH₂ | 2,4-(CH₃)₂—C₆H₃ |
| 1.356 | C(CH₃)₃ | CH(CH₃) | CH₃ | CH₂CH₂ | 3,4-(CH₃)₂C₆H₃ |
| 1.357 | C(CH₃)₃ | CH(CH₃) | CH₃ | CH₂CH₂ | 4-NO₂—C₆H₄ |
| 1.358 | CH(CH₃)₂ | C(CH₃)₂—CH₂ | CH₃ | CH₂CH₂ | 4-Cl—C₆H₄ |
| 1.359 | CH(CH₃)₂ | C(CH₃)₂—CH₂ | CH₃ | CH₂CH₂ | 4-CH₃—C₆H₄ |
| 1.36G | CH(CH₃)₂ | C(CH₃)₂—CH₂ | CH₃ | CH₂CH₂ | 4-CH₃O—C₆H₄ |
| 1.361 | CH(CH₃)₂ | C(CH₃)₂—CH₂ | CH₃ | CH₂CH₂ | 4-CN—C₆H₄ |
| 1.362 | CH(CH₃)₂ | C(CH₃)₂—CH₂ | CH₃ | CH₂CH₂ | 3-Cl—C₆H₄ |
| 1.363 | CH(CH₃)₂ | C(CH₃)₂—CH₂ | CH₃ | CH₂CH₂ | 3-CH₃—C₆H₄ |
| 1.364 | CH(CH₃)₂ | C(CH₃)₂—CH₂ | CH₃ | CH₂CH₂ | 3-CH₃O—C₆H₄ |
| 1.365 | CH(CH₃)₂ | C(CH₃)₂—CH₂ | CH₃ | CH₂CH₂ | 3-CN—C₆H₄ |
| 1.366 | CH(CH₃)₂ | C(CH₃)₂—CH₂ | CH₃ | CH₂CH₂ | 2-Cl—C₆H₄ |
| 1.367 | CH(CH₃)₂ | C(CH₃)₂—CH₂ | CH₃ | CH₂CH₂ | 2-CH₃—C₆H₄ |
| 1.368 | CH(CH₃)₂ | C(CH₃)₂—CH₂ | CH₃ | CH₂CH₂ | 2-CH₃O—C₆H₄ |
| 1.369 | CH(CH₃)₂ | C(CH₃)₂—CH₂ | CH₃ | CH₂CH₂ | 2-CN—C₆H₄ |
| 1.370 | CH(CH₃)₂ | C(CH₃)₂—CH₂ | CH₃ | CH₂CH₂ | 3,4-(CH₃O)₂C₆H₃ |
| 1.371 | CH(CH₃)₂ | C(CH₃)₂—CH₂ | CH₃ | CH₂CH₂ | 2,4-Cl₂—C₆H₃ |
| 1.372 | CH(CH₃)₂ | C(CH₃)₂—CH₂ | CH₃ | CH₂CH₂ | 2,4-(CH₃)₂—C₆H₃ |
| 1.373 | CH(CH₃)₂ | C(CH₃)₂—CH₂ | CH₃ | CH₂CH₂ | 3,4-(CH₃)₂C₆H₃ |
| 1.374 | CH(CH₃)₂ | C(CH₃)₂—CH₂ | CH₃ | CH₂CH₂ | 4-NO₂—C₆H₄ |
| 1.375 | CH(CH₃)C₂H₅ | C(CH₃)₂—CH₂ | CH₃ | CH₂CH₂ | 4-Cl—C₆H₄ |
| 1.376 | CH(CH₃)C₂H₅ | C(CH₃)₂—CH₂ | CH₃ | CH₂CH₂ | 4-CH₃—C₆H₄ |
| 1.377 | CH(CH₃)C₂H₅ | C(CH₃)₂—CH₂ | CH₃ | CH₂CH₂ | 4-CH₃O—C₆H₄ |
| 1.378 | CH(CH₃)C₂H₅ | C(CH₃)₂—CH₂ | CH₃ | CH₂CH₂ | 4-CN—C₆H₄ |
| 1.379 | CH(CH₃)C₂H₅ | C(CH₃)₂—CH₂ | CH₃ | CH₂CH₂ | 3-Cl—C₆H₄ |
| 1.380 | CH(CH₃)C₂H₅ | C(CH₃)₂—CH₂ | CH₃ | CH₂CH₂ | 3-CH₃—C₆H₄ |
| 1.381 | CH(CH₃)C₂H₅ | C(CH₃)₂—CH₂ | CH₃ | CH₂CH₂ | 3-CH₃O—C₆H₄ |
| 1.382 | CH(CH₃)C₂H₅ | C(CH₃)₂—CH₂ | CH₃ | CH₂CH₂ | 3-CN—C₆H₄ |
| 1.383 | CH(CH₃)C₂H₅ | C(CH₃)₂—CH₂ | CH₃ | CH₂CH₂ | 2-Cl—C₆H₄ |
| 1.384 | CH(CH₃)C₂H₅ | C(CH₃)₂—CH₂ | CH₃ | CH₂CH₂ | 2-CH₃—C₆H₄ |
| 1.385 | CH(CH₃)C₂H₅ | C(CH₃)₂—CH₂ | CH₃ | CH₂CH₂ | 2-CH₃O—C₆H₄ |
| 1.386 | CH(CH₃)C₂H₅ | C(CH₃)₂—CH₂ | CH₃ | CH₂CH₂ | 2-CN—C₆H₄ |
| 1.387 | CH(CH₃)C₂H₅ | C(CH₃)₂—CH₂ | CH₃ | CH₂CH₂ | 3,4-(CH₃O)₂C₆H₃ |
| 1.388 | CH(CH₃)C₂H₅ | C(CH₃)₂—CH₂ | CH₃ | CH₂CH₂ | 2,4-Cl₂—C₆H₃ |
| 1.389 | CH(CH₃)C₂H₅ | C(CH₃)₂—CH₂ | CH₃ | CH₂CH₂ | 2,4-(CH₃)₂—C₆H₃ |
| 1.390 | CH(CH₃)C₂H₅ | C(CH₃)₂—CH₂ | CH₃ | CH₂CH₂ | 3,4-(CH₃)₂C₆H₃ |
| 1.391 | CH(CH₃)C₂H₅ | C(CH₃)₂—CH₂ | CH₃ | CH₂CH₂ | 4-NO₂—C₆H₄ |
| 1.392 | C(CH₃)₃ | C(CH₃)₂—CH₂ | CH₃ | CH₂CH₂ | 4-Cl—C₆H₄ |
| 1.393 | C(CH₃)₃ | C(CH₃)₂—CH₂ | CH₃ | CH₂CH₂ | 4-CH₃—C₆H₄ |
| 1.394 | C(CH₃)₃ | C(CH₃)₂—CH₂ | CH₃ | CH₂CH₂ | 4-CH₃O—C₆H₄ |
| 1.395 | C(CH₃)₃ | C(CH₃)₂—CH₂ | CH₃ | CH₂CH₂ | 4-CN—C₆H₄ |
| 1.396 | C(CH₃)₃ | C(CH₃)₂—CH₂ | CH₃ | CH₂CH₂ | 3-Cl—C₆H₄ |
| 1.397 | C(CH₃)₃ | C(CH₃)₂—CH₂ | CH₃ | CH₂CH₂ | 3-CH₃—C₆H₄ |
| 1.398 | C(CH₃)₃ | C(CH₃)₂—CH₂ | CH₃ | CH₂CH₂ | 3-CH₃O—C₆H₄ |
| 1.399 | C(CH₃)₃ | C(CH₃)₂—CH₂ | CH₃ | CH₂CH₂ | 3-CN—C₆H₄ |
| 1.400 | C(CH₃)₃ | C(CH₃)₂—CH₂ | CH₃ | CH₂CH₂ | 2-Cl—C₆H₄ |
| 1.401 | C(CH₃)₃ | C(CH₃)₂—CH₂ | CH₃ | CH₂CH₂ | 2-CH₃—C₆H₄ |
| 1.402 | C(CH₃)₃ | C(CH₃)₂—CH₂ | CH₃ | CH₂CH₂ | 2-CH₃O—C₆H₄ |
| 1.403 | C(CH₃)₃ | C(CH₃)₂—CH₂ | CH₃ | CH₂CH₂ | 2-CN—C₆H₄ |
| 1.404 | C(CH₃)₃ | C(CH₃)₂—CH₂ | CH₃ | CH₂CH₂ | 3,4-(CH₃O)₂C₆H₃ |
| 1.405 | C(CH₃)₃ | C(CH₃)₂—CH₂ | CH₃ | CH₂CH₂ | 2,4-Cl₂—C₆H₃ |
| 1.406 | C(CH₃)₃ | C(CH₃)₂—CH₂ | CH₃ | CH₂CH₂ | 2,4-(CH₃)₂—C₆H₃ |
| 1.407 | C(CH₃)₃ | C(CH₃)₂—CH₂ | CH₃ | CH₂CH₂ | 3,4-(CH₃)₂C₆H₃ |
| 1.408 | C(CH₃)₃ | C(CH₃)₂—CH₂ | CH₃ | CH₂CH₂ | 4-NO₂—C₆H₄ |
| 1.409 | CH(CH₃)₂ | CH(CH₃) | H | CH₂CH₂ | 4-Cl—C₆H₄ |
| 1.410 | CH(CH₃)₂ | CH(CH₃) | H | CH₂CH₂ | 4-CH₃—C₆H₄ |
| 1.411 | CH(CH₃)₂ | CH(CH₃) | H | CH₂CH₂ | 4-CH₃O—C₆H₄ |
| 1.412 | CH(CH₃)₂ | CH(CH₃) | H | CH₂CH₂ | 4-CN—C₆H₄ |
| 1.413 | CH(CH₃)₂ | CH(CH₃) | H | CH₂CH₂ | 3-Cl—C₆H₄ |
| 1.414 | CH(CH₃)₂ | CH(CH₃) | H | CH₂CH₂ | 3-CH₃—C₆H₄ |
| 1.415 | CH(CH₃)₂ | CH(CH₃) | H | CH₂CH₂ | 3-CH₃O—C₆H₄ |
| 1.416 | CH(CH₃)₂ | CH(CH₃) | H | CH₂CH₂ | 3-CN—C₆H₄ |
| 1.417 | CH(CH₃)₂ | CH(CH₃) | H | CH₂CH₂ | 2-Cl—C₆H₄ |
| 1.418 | CH(CH₃)₂ | CH(CH₃) | H | CH₂CH₂ | 2-CH₃—C₆H₄ |

TABLE A-continued $$R^1-O-\overset{O}{\underset{}{C}}-NH-\overset{CH(CH_3)_2}{\underset{\underline{S}}{CH}}-\overset{O}{\underset{}{C}}-NH-A-\overset{Y}{\underset{}{C}}=N-O-Z-Ar \qquad (I')$$

| No. | R¹ | A | Y | Z | Ar |
|---|---|---|---|---|---|
| 1.419 | CH(CH$_3$)$_2$ | CH(CH$_3$) | H | CH$_2$CH$_2$ | 2-CH$_3$O—C$_6$H$_4$ |
| 1.420 | CH(CH$_3$)$_2$ | CH(CH$_3$) | H | CH$_2$CH$_2$ | 2-CN—C$_6$H$_4$ |
| 1.421 | CH(CH$_3$)$_2$ | CH(CH$_3$) | H | CH$_2$CH$_2$ | 3,4-(CH$_3$O)$_2$C$_6$H$_3$ |
| 1.422 | CH(CH$_3$)$_2$ | CH(CH$_3$) | H | CH$_2$CH$_2$ | 2,4-Cl$_2$—C$_6$H$_3$ |
| 1.423 | CH(CH$_3$)$_2$ | CH(CH$_3$) | H | CH$_2$CH$_2$ | 2,4-(CH$_3$)$_2$—C$_6$H$_3$ |
| 1.424 | CH(CH$_3$)$_2$ | CH(CH$_3$) | H | CH$_2$CH$_2$ | 3,4-(CH$_3$)$_2$C$_6$H$_3$ |
| 1.425 | CH(CH$_3$)$_2$ | CH(CH$_3$) | H | CH$_2$CH$_2$ | 4-NO$_2$—C$_6$H$_4$ |
| 1.426 | CH(CH$_3$)C$_2$H$_5$ | CH(CH$_3$) | H | CH$_2$CH$_2$ | 4-Cl—C$_6$H$_4$ |
| 1.427 | CH(CH$_3$)C$_2$H$_5$ | CH(CH$_3$) | H | CH$_2$CH$_2$ | 4-CH$_3$—C$_6$H$_4$ |
| 1.428 | CH(CH$_3$)C$_2$H$_5$ | CH(CH$_3$) | H | CH$_2$CH$_2$ | 4-CH$_3$O—C$_6$H$_4$ |
| 1.429 | CH(CH$_3$)C$_2$H$_5$ | CH(CH$_3$) | H | CH$_2$CH$_2$ | 4-CN—C$_6$H$_4$ |
| 1.430 | CH(CH$_3$)C$_2$H$_5$ | CH(CH$_3$) | H | CH$_2$CH$_2$ | 3-Cl—C$_6$H$_4$ |
| 1.431 | CH(CH$_3$)C$_2$H$_5$ | CH(CH$_3$) | H | CH$_2$CH$_2$ | 3-CH$_3$—C$_6$H$_4$ |
| 1.432 | CH(CH$_3$)C$_2$H$_5$ | CH(CH$_3$) | H | CH$_2$CH$_2$ | 3-CH$_3$O—C$_6$H$_4$ |
| 1.433 | CH(CH$_3$)C$_2$H$_5$ | CH(CH$_3$) | H | CH$_2$CH$_2$ | 3-CN—C$_6$H$_4$ |
| 1.434 | CH(CH$_3$)C$_2$H$_5$ | CH(CH$_3$) | H | CH$_2$CH$_2$ | 2-Cl—C$_6$H$_4$ |
| 1.435 | CH(CH$_3$)C$_2$H$_5$ | CH(CH$_3$) | H | CH$_2$CH$_2$ | 2-CH$_3$—C$_6$H$_4$ |
| 1.436 | CH(CH$_3$)C$_2$H$_5$ | CH(CH$_3$) | H | CH$_2$CH$_2$ | 2-CH$_3$O—C$_6$H$_4$ |
| 1.437 | CH(CH$_3$)C$_2$H$_5$ | CH(CH$_3$) | H | CH$_2$CH$_2$ | 2-CN—C$_6$H$_4$ |
| 1.438 | CH(CH$_3$)C$_2$H$_5$ | CH(CH$_3$) | H | CH$_2$CH$_2$ | 3,4-(CH$_3$O)$_2$C$_6$H$_3$ |
| 1.439 | CH(CH$_3$)C$_2$H$_5$ | CH(CH$_3$) | H | CH$_2$CH$_2$ | 2,4-Cl$_2$—C$_6$H$_3$ |
| 1.440 | CH(CH$_3$)C$_2$H$_5$ | CH(CH$_3$) | H | CH$_2$CH$_2$ | 2,4-(CH$_3$)$_2$—C$_6$H$_3$ |
| 1.441 | CH(CH$_3$)C$_2$H$_5$ | CH(CH$_3$) | H | CH$_2$CH$_2$ | 3,4-(CH$_3$)$_2$C$_6$H$_3$ |
| 1.442 | CH(CH$_3$)C$_2$H$_5$ | CH(CH$_3$) | H | CH$_2$CH$_2$ | 4-NO$_2$—C$_6$H$_4$ |
| 1.443 | C(CH$_3$)$_3$ | CH(CH$_3$) | H | CH$_2$CH$_2$ | 4-Cl—C$_6$H$_4$ |
| 1.444 | C(CH$_3$)$_3$ | CH(CH$_3$) | H | CH$_2$CH$_2$ | 4-CH$_3$—C$_6$H$_4$ |
| 1.445 | C(CH$_3$)$_3$ | CH(CH$_3$) | H | CH$_2$CH$_2$ | 4-CH$_3$O—C$_6$H$_4$ |
| 1.446 | C(CH$_3$)$_3$ | CH(CH$_3$) | H | CH$_2$CH$_2$ | 4-CN—C$_6$H$_4$ |
| 1.447 | C(CH$_3$)$_3$ | CH(CH$_3$) | H | CH$_2$CH$_2$ | 3-Cl—C$_6$H$_4$ |
| 1.448 | C(CH$_3$)$_3$ | CH(CH$_3$) | H | CH$_2$CH$_2$ | 3-CH$_3$—C$_6$H$_4$ |
| 1.449 | C(CH$_3$)$_3$ | CH(CH$_3$) | H | CH$_2$CH$_2$ | 3-CH$_3$O—C$_6$H$_4$ |
| 1.450 | C(CH$_3$)$_3$ | CH(CH$_3$) | H | CH$_2$CH$_2$ | 3-CN—C$_6$H$_4$ |
| 1.451 | C(CH$_3$)$_3$ | CH(CH$_3$) | H | CH$_2$CH$_2$ | 2-Cl—C$_6$H$_4$ |
| 1.452 | C(CH$_3$)$_3$ | CH(CH$_3$) | H | CH$_2$CH$_2$ | 2-CH$_3$—C$_6$H$_4$ |
| 1.453 | C(CH$_3$)$_3$ | CH(CH$_3$) | H | CH$_2$CH$_2$ | 2-CH$_3$O—C$_6$H$_4$ |
| 1.454 | C(CH$_3$)$_3$ | CH(CH$_3$) | H | CH$_2$CH$_2$ | 2-CN—C$_6$H$_4$ |
| 1.455 | C(CH$_3$)$_3$ | CH(CH$_3$) | H | CH$_2$CH$_2$ | 3,4-(CH$_3$O)$_2$C$_6$H$_3$ |
| 1.456 | C(CH$_3$)$_3$ | CH(CH$_3$) | H | CH$_2$CH$_2$ | 2,4-Cl$_2$—C$_6$H$_3$ |
| 1.457 | C(CH$_3$)$_3$ | CH(CH$_3$) | H | CH$_2$CH$_2$ | 2,4-(CH$_3$)$_2$—C$_6$H$_3$ |
| 1.458 | C(CH$_3$)$_3$ | CH(CH$_3$) | H | CH$_2$CH$_2$ | 3,4-(CH$_3$)$_2$C$_6$H$_3$ |
| 1.459 | C(CH$_3$)$_3$ | CH(CH$_3$) | H | CH$_2$CH$_2$ | 4-NO$_2$—C$_6$H$_4$ |
| 1.460 | CH(CH$_3$)$_2$ | C(CH$_3$)$_2$—CH$_2$ | H | CH$_2$CH$_2$ | 4-Cl—C$_6$H$_4$ |
| 1.461 | CH(CH$_3$)$_2$ | C(CH$_3$)$_2$—CH$_2$ | H | CH$_2$CH$_2$ | 4-CH$_3$—C$_6$H$_4$ |
| 1.462 | CH(CH$_3$)$_2$ | C(CH$_3$)$_2$—CH$_2$ | H | CH$_2$CH$_2$ | 4-CH$_3$O—C$_6$H$_4$ |
| 1.463 | CH(CH$_3$)$_2$ | C(CH$_3$)$_2$—CH$_2$ | H | CH$_2$CH$_2$ | 4-CN—C$_6$H$_4$ |
| 1.464 | CH(CH$_3$)$_2$ | C(CH$_3$)$_2$—CH$_2$ | H | CH$_2$CH$_2$ | 3-Cl—C$_6$H$_4$ |
| 1.465 | CH(CH$_3$)$_2$ | C(CH$_3$)$_2$—CH$_2$ | H | CH$_2$CH$_2$ | 3-CH$_3$—C$_6$H$_4$ |
| 1.466 | CH(CH$_3$)$_2$ | C(CH$_3$)$_2$—CH$_2$ | H | CH$_2$CH$_2$ | 3-CH$_3$O—C$_6$H$_4$ |
| 1.467 | CH(CH$_3$)$_2$ | C(CH$_3$)$_2$—CH$_2$ | H | CH$_2$CH$_2$ | 3-CN—C$_6$H$_4$ |
| 1.468 | CH(CH$_3$)$_2$ | C(CH$_3$)$_2$—CH$_2$ | H | CH$_2$CH$_2$ | 2-Cl—C$_6$H$_4$ |
| 1.469 | CH(CH$_3$)$_2$ | C(CH$_3$)$_2$—CH$_2$ | H | CH$_2$CH$_2$ | 2-CH$_3$—C$_6$H$_4$ |
| 1.470 | CH(CH$_3$)$_2$ | C(CH$_3$)$_2$—CH$_2$ | H | CH$_2$CH$_2$ | 2-CH$_3$O—C$_6$H$_4$ |
| 1.471 | CH(CH$_3$)$_2$ | C(CH$_3$)$_2$—CH$_2$ | H | CH$_2$CH$_2$ | 2-CN—C$_6$H$_4$ |
| 1.472 | CH(CH$_3$)$_2$ | C(CH$_3$)$_2$—CH$_2$ | H | CH$_2$CH$_2$ | 3,4-(CH$_3$O)$_2$C$_6$H$_3$ |
| 1.473 | CH(CH$_3$)$_2$ | C(CH$_3$)$_2$—CH$_2$ | H | CH$_2$CH$_2$ | 2,4-Cl$_2$—C$_6$H$_3$ |
| 1.474 | CH(CH$_3$)$_2$ | C(CH$_3$)$_2$—CH$_2$ | H | CH$_2$CH$_2$ | 2,4-(CH$_3$)$_2$—C$_6$H$_3$ |
| 1.475 | CH(CH$_3$)$_2$ | C(CH$_3$)$_2$—CH$_2$ | H | CH$_2$CH$_2$ | 3,4-(CH$_3$)$_2$C$_6$H$_3$ |
| 1.476 | CH(CH$_3$)$_2$ | C(CH$_3$)$_2$—CH$_2$ | H | CH$_2$CH$_2$ | 4-NO$_2$—C$_6$H$_4$ |
| 1.477 | CH(CH$_3$)C$_2$H$_5$ | C(CH$_3$)$_2$—CH$_2$ | H | CH$_2$CH$_2$ | 4-Cl—C$_6$H$_4$ |
| 1.478 | CH(CH$_3$)C$_2$H$_5$ | C(CH$_3$)$_2$—CH$_2$ | H | CH$_2$CH$_2$ | 4-CH$_3$—C$_6$H$_4$ |
| 1.479 | CH(CH$_3$)C$_2$H$_5$ | C(CH$_3$)$_2$—CH$_2$ | H | CH$_2$CH$_2$ | 4-CH$_3$O—C$_6$H$_4$ |
| 1.480 | CH(CH$_3$)C$_2$H$_5$ | C(CH$_3$)$_2$—CH$_2$ | H | CH$_2$CH$_2$ | 4-CN—C$_6$H$_4$ |
| 1.481 | CH(CH$_3$)C$_2$H$_5$ | C(CH$_3$)$_2$—CH$_2$ | H | CH$_2$CH$_2$ | 3-Cl—C$_6$H$_4$ |
| 1.482 | CH(CH$_3$)C$_2$H$_5$ | C(CH$_3$)$_2$—CH$_2$ | H | CH$_2$CH$_2$ | 3-CH$_3$—C$_6$H$_4$ |
| 1.483 | CH(CH$_3$)C$_2$H$_5$ | C(CH$_3$)$_2$—CH$_2$ | H | CH$_2$CH$_2$ | 3-CH$_3$O—C$_6$H$_4$ |
| 1.484 | CH(CH$_3$)C$_2$H$_5$ | C(CH$_3$)$_2$—CH$_2$ | H | CH$_2$CH$_2$ | 3-CN—C$_6$H$_4$ |
| 1.485 | CH(CH$_3$)C$_2$H$_5$ | C(CH$_3$)$_2$—CH$_2$ | H | CH$_2$CH$_2$ | 2-Cl—C$_6$H$_4$ |
| 1.486 | CH(CH$_3$)C$_2$H$_5$ | C(CH$_3$)$_2$—CH$_2$ | H | CH$_2$CH$_2$ | 2-CH$_3$—C$_6$H$_4$ |
| 1.487 | CH(CH$_3$)C$_2$H$_5$ | C(CH$_3$)$_2$—CH$_2$ | H | CH$_2$CH$_2$ | 2-CH$_3$O—C$_6$H$_4$ |
| 1.488 | CH(CH$_3$)C$_2$H$_5$ | C(CH$_3$)$_2$—CH$_2$ | H | CH$_2$CH$_2$ | 2-CN—C$_6$H$_4$ |

TABLE A-continued $$R^1-O-\overset{O}{C}-NH-\underset{S}{\overset{CH(CH_3)_2}{\underset{|}{CH}}}-\overset{O}{C}-NH-A-\overset{Y}{\underset{|}{C}}=N-O-Z-Ar \quad (I')$$

| No. | R¹ | A | Y | Z | Ar |
|---|---|---|---|---|---|
| 1.489 | CH(CH₃)C₂H₅ | C(CH₃)₂—CH₂ | H | CH₂CH₂ | 3,4-(CH₃O)₂C₆H₃ |
| 1.490 | CH(CH₃)C₂H₅ | C(CH₃)₂—CH₂ | H | CH₂CH₂ | 2,4-Cl₂—C₆H₃ |
| 1.491 | CH(CH₃)C₂H₅ | C(CH₃)₂—CH₂ | H | CH₂CH₂ | 2,4-(CH₃)₂—C₆H₃ |
| 1.492 | CH(CH₃)C₂H₅ | C(CH₃)₂—CH₂ | H | CH₂CH₂ | 3,4-(CH₃)₂C₆H₃ |
| 1.493 | CH(CH₃)C₂H₅ | C(CH₃)₂—CH₂ | H | CH₂CH₂ | 4-NO₂—C₆H₄ |
| 1.494 | C(CH₃)₃ | C(CH₃)₂—CH₂ | H | CH₂CH₂ | 4-Cl—C₆H₄ |
| 1.495 | C(CH₃)₃ | C(CH₃)₂—CH₂ | H | CH₂CH₂ | 4-CH₃—C₆H₄ |
| 1.496 | C(CH₃)₃ | C(CH₃)₂—CH₂ | H | CH₂CH₂ | 4-CH₃O—C₆H₄ |
| 1.497 | C(CH₃)₃ | C(CH₃)₂—CH₂ | H | CH₂CH₂ | 4-CN—C₆H₄ |
| 1.498 | C(CH₃)₃ | C(CH₃)₂—CH₂ | H | CH₂CH₂ | 3-Cl—C₆H₄ |
| 1.499 | C(CH₃)₃ | C(CH₃)₂—CH₂ | H | CH₂CH₂ | 3-CH₃—C₆H₄ |
| 1.500 | C(CH₃)₃ | C(CH₃)₂—CH₂ | H | CH₂CH₂ | 3-CH₃O—C₆H₄ |
| 1.501 | C(CH₃)₃ | C(CH₃)₂—CH₂ | H | CH₂CH₂ | 3-CN—C₆H₄ |
| 1.502 | C(CH₃)₃ | C(CH₃)₂—CH₂ | H | CH₂CH₂ | 2-Cl—C₆H₄ |
| 1.503 | C(CH₃)₃ | C(CH₃)₂—CH₂ | H | CH₂CH₂ | 2-CH₃—C₆H₄ |
| 1.504 | C(CH₃)₃ | C(CH₃)₂—CH₂ | H | CH₂CH₂ | 2-CH₃O—C₆H₄ |
| 1.505 | C(CH₃)₃ | C(CH₃)₂—CH₂ | H | CH₂CH₂ | 2-CN—C₆H₄ |
| 1.506 | C(CH₃)₃ | C(CH₃)₂—CH₂ | H | CH₂CH₂ | 3,4-(CH₃O)₂C₆H₃ |
| 1.507 | C(CH₃)₃ | C(CH₃)₂—CH₂ | H | CH₂CH₂ | 2,4-Cl₂—C₆H₃ |
| 1.508 | C(CH₃)₃ | C(CH₃)₂—CH₂ | H | CH₂CH₂ | 2,4-(CH₃)₂—C₆H₃ |
| 1.509 | C(CH₃)₃ | C(CH₃)₂—CH₂ | H | CH₂CH₂ | 3,4-(CH₃)₂C₆H₃ |
| 1.510 | C(CH₃)₃ | C(CH₃)₂—CH₂ | H | CH₂CH₂ | 4-NO₂—C₆H₄ |
| 1.511 | CH(CH₃)₂ | CH₂ | CH₃ | CH₂CH₂ | 4-Cl—C₆H₄ |
| 1.512 | CH(CH₃)₂ | CH₂ | CH₃ | CH₂CH₂ | 4-CH₃—C₆H₄ |
| 1.513 | CH(CH₃)₂ | CH₂ | CH₃ | CH₂CH₂ | 4-CH₃O—C₆H₄ |
| 1.514 | CH(CH₃)₂ | CH₂ | CH₃ | CH₂CH₂ | 4-CN—C₆H₄ |
| 1.515 | CH(CH₃)₂ | CH₂ | CH₃ | CH₂CH₂ | 3-Cl—C₆H₄ |
| 1.516 | CH(CH₃)₂ | CH₂ | CH₃ | CH₂CH₂ | 3-CH₃—C₆H₄ |
| 1.517 | CH(CH₃)₂ | CH₂ | CH₃ | CH₂CH₂ | 3-CH₃O—C₆H₄ |
| 1.518 | CH(CH₃)₂ | CH₂ | CH₃ | CH₂CH₂ | 3-CN—C₆H₄ |
| 1.519 | CH(CH₃)₂ | CH₂ | CH₃ | CH₂CH₂ | 2-Cl—C₆H₄ |
| 1.520 | CH(CH₃)₂ | CH₂ | CH₃ | CH₂CH₂ | 2-CH₃—C₆H₄ |
| 1.521 | CH(CH₃)₂ | CH₂ | CH₃ | CH₂CH₂ | 2-CH₃O—C₆H₄ |
| 1.522 | CH(CH₃)₂ | CH₂ | CH₃ | CH₂CH₂ | 2-CN—C₆H₄ |
| 1.523 | CH(CH₃)₂ | CH₂ | CH₃ | CH₂CH₂ | 3,4-(CH₃O)₂C₆H₃ |
| 1.524 | CH(CH₃)₂ | CH₂ | CH₃ | CH₂CH₂ | 2,4-Cl₂—C₆H₃ |
| 1.525 | CH(CH₃)₂ | CH₂ | CH₃ | CH₂CH₂ | 2,4-(CH₃)₂—C₆H₃ |
| 1.526 | CH(CH₃)₂ | CH₂ | CH₃ | CH₂CH₂ | 3,4-(CH₃)₂C₆H₃ |
| 1.527 | CH(CH₃)₂ | CH₂ | CH₃ | CH₂CH₂ | 4-NO₂—C₆H₄ |
| 1.528 | CH(CH₃)C₂H₅ | CH₂ | CH₃ | CH₂CH₂ | 4-Cl—C₆H₄ |
| 1.529 | CH(CH₃)C₂H₅ | CH₂ | CH₃ | CH₂CH₂ | 4-CH₃—C₆H₄ |
| 1.530 | CH(CH₃)C₂H₅ | CH₂ | CH₃ | CH₂CH₂ | 4-CH₃O—C₆H₄ |
| 1.531 | CH(CH₃)C₂H₅ | CH₂ | CH₃ | CH₂CH₂ | 4-CN—C₆H₄ |
| 1.532 | CH(CH₃)C₂H₅ | CH₂ | CH₃ | CH₂CH₂ | 3-Cl—C₆H₄ |
| 1.533 | CH(CH₃)C₂H₅ | CH₂ | CH₃ | CH₂CH₂ | 3-CH₃—C₆H₄ |
| 1.534 | CH(CH₃)C₂H₅ | CH₂ | CH₃ | CH₂CH₂ | 3-CH₃O—C₆H₄ |
| 1.535 | CH(CH₃)C₂H₅ | CH₂ | CH₃ | CH₂CH₂ | 3-CN—C₆H₄ |
| 1.536 | CH(CH₃)C₂H₅ | CH₂ | CH₃ | CH₂CH₂ | 2-Cl—C₆H₄ |
| 1.537 | CH(CH₃)C₂H₅ | CH₂ | CH₃ | CH₂CH₂ | 2-CH₃—C₆H₄ |
| 1.538 | CH(CH₃)C₂H₅ | CH₂ | CH₃ | CH₂CH₂ | 2-CH₃O—C₆H₄ |
| 1.539 | CH(CH₃)C₂H₅ | CH₂ | CH₃ | CH₂CH₂ | 2-CN—C₆H₄ |
| 1.540 | CH(CH₃)C₂H₅ | CH₂ | CH₃ | CH₂CH₂ | 3,4-(CH₃O)₂C₆H₃ |
| 1.541 | CH(CH₃)C₂H₅ | CH₂ | CH₃ | CH₂CH₂ | 2,4-Cl₂—C₆H₃ |
| 1.542 | CH(CH₃)C₂H₅ | CH₂ | CH₃ | CH₂CH₂ | 2,4-(CH₃)₂—C₆H₃ |
| 1.543 | CH(CH₃)C₂H₅ | CH₂ | CH₃ | CH₂CH₂ | 3,4-(CH₃)₂C₆H₃ |
| 1.544 | CH(CH₃)C₂H₅ | CH₂ | CH₃ | CH₂CH₂ | 4-NO₂—C₆H₄ |
| 1.545 | C(CH₃)₃ | CH₂ | CH₃ | CH₂CH₂ | 4-Cl—C₆H₄ |
| 1.546 | C(CH₃)₃ | CH₂ | CH₃ | CH₂CH₂ | 4-CH₃—C₆H₄ |
| 1.547 | C(CH₃)₃ | CH₂ | CH₃ | CH₂CH₂ | 4-CH₃O—C₆H₄ |
| 1.548 | C(CH₃)₃ | CH₂ | CH₃ | CH₂CH₂ | 4-CN—C₆H₄ |
| 1.549 | C(CH₃)₃ | CH₂ | CH₃ | CH₂CH₂ | 3-Cl—C₆H₄ |
| 1.550 | C(CH₃)₃ | CH₂ | CH₃ | CH₂CH₂ | 3-CH₃—C₆H₄ |
| 1.551 | C(CH₃) | CH₂ | CH₃ | CH₂CH₂ | 3-CH₃O—C₆H₄ |
| 1.552 | C(CH₃)₃ | CH₂ | CH₃ | CH₂CH₂ | 3-CN—C₆H₄ |
| 1.553 | C(CH₃)₃ | CH₂ | CH₃ | CH₂CH₂ | 2-Cl—C₆H₄ |
| 1.554 | C(CH₃)₃ | CH₂ | CH₃ | CH₂CH₂ | 2-CH₃—C₆H₄ |
| 1.555 | C(CH₃) | CH₂ | CH₃ | CH₂CH₂ | 2-CH₃O—C₆H₄ |
| 1.556 | C(CH₃)₃ | CH₂ | CH₃ | CH₂CH₂ | 2-CN—C₆H₄ |
| 1.557 | C(CH₃)₃ | CH₂ | CH₃ | CH₂CH₂ | 3,4-(CH₃O)₂C₆H₃ |
| 1.558 | C(CH₃)₃ | CH₂ | CH₃ | CH₂CH₂ | 2,4-Cl₂—C₆H₃ |

TABLE A-continued $$R^1-O-\overset{O}{\underset{}{C}}-NH-\underset{\underline{S}}{\overset{CH(CH_3)_2}{\underset{|}{CH}}}-\overset{O}{\underset{}{C}}-NH-A-\overset{Y}{\underset{|}{C}}=N-O-Z-Ar \quad (I')$$

| No. | R¹ | A | Y | Z | Ar |
|---|---|---|---|---|---|
| 1.559 | C(CH₃)₃ | CH₂ | CH₃ | CH₂CH₂ | 2,4-(CH₃)₂—C₆H₃ |
| 1.560 | C(CH₃)₃ | CH₂ | CH₃ | CH₂CH₂ | 3,4-(CH₃)₂C₆H₃ |
| 1.561 | C(CH₃)₃ | CH₂ | CH₃ | CH₂CH₂ | 4-NO₂—C₆H₄ |
| 1.562 | CH(CH₃)₂ | CH₂ | H | CH₂CH₂ | 4-Cl—C₆H₄ |
| 1.563 | CH(CH₃)₂ | CH₂ | H | CH₂CH₂ | 4-CH₃—C₆H₄ |
| 1.564 | CH(CH₃)₂ | CH₂ | H | CH₂CH₂ | 4-CH₃O—C₆H₄ |
| 1.565 | CH(CH₃)₂ | CH₂ | H | CH₂CH₂ | 4-CN—C₆H₄ |
| 1.566 | CH(CH₃)₂ | CH₂ | H | CH₂CH₂ | 3-Cl—C₆H₄ |
| 1.567 | CH(CH₃)₂ | CH₂ | H | CH₂CH₂ | 3-CH₃—C₆H₄ |
| 1.568 | CH(CH₃)₂ | CH₂ | H | CH₂CH₂ | 3-CH₃O—C₆H₄ |
| 1.569 | CH(CH₃)₂ | CH₂ | H | CH₂CH₂ | 3-CN—C₆H₄ |
| 1.570 | CH(CH₃)₂ | CH₂ | H | CH₂CH₂ | 2-Cl—C₆H₄ |
| 1.571 | CH(CH₃)₂ | CH₂ | H | CH₂CH₂ | 2-CH₃—C₆H₄ |
| 1.572 | CH(CH₃)₂ | CH₂ | H | CH₂CH₂ | 2-CH₃O—C₆H₄ |
| 1.573 | CH(CH₃)₂ | CH₂ | H | CH₂CH₂ | 2-CN—C₆H₄ |
| 1.574 | CH(CH₃)₂ | CH₂ | H | CH₂CH₂ | 3,4-(CH₃O)₂C₆H₃ |
| 1.575 | CH(CH₃)₂ | CH₂ | H | CH₂CH₂ | 2,4-Cl₂—C₆H₃ |
| 1.576 | CH(CH₃)₂ | CH₂ | H | CH₂CH₂ | 2,4-(CH₃)₂—C₆H₃ |
| 1.577 | CH(CH₃)₂ | CH₂ | H | CH₂CH₂ | 3,4-(CH₃)₂C₆H₃ |
| 1.578 | CH(CH₃)₂ | CH₂ | H | CH₂CH₂ | 4-NO₂—C₆H₄ |
| 1.579 | CH(CH₃)C₂H₅ | CH₂ | H | CH₂CH₂ | 4-Cl—C₆H₄ |
| 1.580 | CH(CH₃)C₂H₅ | CH₂ | H | CH₂CH₂ | 4-CH₃—C₆H₄ |
| 1.581 | CH(CH₃)C₂H₅ | CH₂ | H | CH₂CH₂ | 4-CH₃O—C₆H₄ |
| 1.582 | CH(CH₃)C₂H₅ | CH₂ | H | CH₂CH₂ | 4-CN—C₆H₄ |
| 1.583 | CH(CH₃)C₂H₅ | CH₂ | H | CH₂CH₂ | 3-Cl—C₆H₄ |
| 1.584 | CH(CH₃)C₂H₅ | CH₂ | H | CH₂CH₂ | 3-CH₃—C₆H₄ |
| 1.585 | CH(CH₃)C₂H₅ | CH₂ | H | CH₂CH₂ | 3-CH₃O—C₆H₄ |
| 1.586 | CH(CH₃)C₂H₅ | CH₂ | H | CH₂CH₂ | 3-CN—C₆H₄ |
| 1.587 | CH(CH₃)C₂H₅ | CH₂ | H | CH₂CH₂ | 2-Cl—C₆H₄ |
| 1.588 | CH(CH₃)C₂H₅ | CH₂ | H | CH₂CH₂ | 2-CH₃—C₆H₄ |
| 1.589 | CH(CH₃)C₂H₅ | CH₂ | H | CH₂CH₂ | 2-CH₃O—C₆H₄ |
| 1.590 | CH(CH₃)C₂H₅ | CH₂ | H | CH₂CH₂ | 2-CN—C₆H₄ |
| 1.591 | CH(CH₃)C₂H₅ | CH₂ | H | CH₂CH₂ | 3,4-(CH₃O)₂C₆H₃ |
| 1.592 | CH(CH₃)C₂H₅ | CH₂ | H | CH₂CH₂ | 2,4-Cl₂—C₆H₃ |
| 1.593 | CH(CH₃)C₂H₅ | CH₂ | H | CH₂CH₂ | 2,4-(CH₃)₂—C₆H₃ |
| 1.594 | CH(CH₃)C₂H₅ | CH₂ | H | CH₂CH₂ | 3,4-(CH₃)₂C₆H₃ |
| 1.595 | CH(CH₃)C₂H₅ | CH₂ | H | CH₂CH₂ | 4-NO₂—C₆H₄ |
| 1.596 | C(CH₃)₃ | CH₂ | H | CH₂CH₂ | 4-Cl—C₆H₄ |
| 1.597 | C(CH₃)₃ | CH₂ | H | CH₂CH₂ | 4-CH₃—C₆H₄ |
| 1.598 | C(CH₃)₃ | CH₂ | H | CH₂CH₂ | 4-CH₃O—C₆H₄ |
| 1.599 | C(CH₃)₃ | CH₂ | H | CH₂CH₂ | 4-CN—C₆H₄ |
| 1.600 | C(CH₃)₃ | CH₂ | H | CH₂CH₂ | 3-Cl—C₆H₄ |
| 1.601 | C(CH₃)₃ | CH₂ | H | CH₂CH₂ | 3-CH₃—C₆H₄ |
| 1.602 | C(CH₃)₃ | CH₂ | H | CH₂CH₂ | 3-CH₃O—C₆H₄ |
| 1.603 | C(CH₃)₃ | CH₂ | H | CH₂CH₂ | 3-CN—C₆H₄ |
| 1.604 | C(CH₃)₃ | CH₂ | H | CH₂CH₂ | 2-Cl—C₆H₄ |
| 1.605 | C(CH₃)₃ | CH₂ | H | CH₂CH₂ | 2-CH₃—C₆H₄ |
| 1.606 | C(CH₃)₃ | CH₂ | H | CH₂CH₂ | 2-CH₃O—C₆H₄ |
| 1.607 | C(CH₃)₃ | CH₂ | H | CH₂CH₂ | 2-CN—C₆H₄ |
| 1.608 | C(CH₃)₃ | CH₂ | H | CH₂CH₂ | 3,4-(CH₃O)₂C₆H₃ |
| 1.609 | C(CH₃)₃ | CH₂ | H | CH₂CH₂ | 2,4-Cl₂—C₆H₃ |
| 1.610 | C(CH₃)₃ | CH₂ | H | CH₂CH₂ | 2,4-(CH₃)₂—C₆H₃ |
| 1.611 | C(CH₃)₃ | CH₂ | H | CH₂CH₂ | 3,4-(CH₃)₂C₆H₃ |
| 1.612 | C(CH₃)₃ | CH₂ | H | CH₂CH₂ | 4-NO₂—C₆H₄ |
| 1.1225 | CH(CH₃)₂ | CH(CH₃) | CH₃ | CH(CH₃) | 4-Cl—C₆H₄ |
| 1.1226 | CH(CH₃)₂ | CH(CH₃) | CH₃ | CH(CH₃) | 4-CH₃—C₆H₄ |
| 1.1227 | CH(CH₃)₂ | CH(CH₃) | CH₃ | CH(CH₃) | 4-CH₃O—C₆H₄ |
| 1.1228 | CH(CH₃)₂ | CH(CH₃) | CH₃ | CH(CH₃) | 4-CN—C₆H₄ |
| 1.1229 | CH(CH₃)₂ | CH(CH₃) | CH₃ | CH(CH₃) | 3-Cl—C₆H₄ |
| 1.1230 | CH(CH₃)₂ | CH(CH₃) | CH₃ | CH(CH₃) | 3-CH₃—C₆H₄ |
| 1.1231 | CH(CH₃)₂ | CH(CH₃) | CH₃ | CH(CH₃) | 3-CH₃O—C₆H₄ |
| 1.1232 | CH(CH₃)₂ | CH(CH₃) | CH₃ | CH(CH₃) | 3-CN—C₆H₄ |
| 1.1233 | CH(CH₃)₂ | CH(CH₃) | CH₃ | CH(CH₃) | 2-Cl—C₆H₄ |
| 1.1234 | CH(CH₃)₂ | CH(CH₃) | CH₃ | CH(CH₃) | 2-CH₃—C₆H₄ |
| 1.1235 | CH(CH₃)₂ | CH(CH₃) | CH₃ | CH(CH₃) | 2-CH₃O—C₆H₄ |
| 1.1236 | CH(CH₃)₂ | CH(CH₃) | CH₃ | CH(CH₃) | 2-CN—C₆H₄ |
| 1.1237 | CH(CH₃)₂ | CH(CH₃) | CH₃ | CH(CH₃) | 3,4-(CH₃O)₂C₆H₃ |
| 1.1238 | CH(CH₃)₂ | CH(CH₃) | CH₃ | CH(CH₃) | 2,4-Cl₂—C₆H₃ |
| 1.1239 | CH(CH₃)₂ | CH(CH₃) | CH₃ | CH(CH₃) | 2,4-(CH₃)₂—C₆H₃ |
| 1.1240 | CH(CH₃)₂ | CH(CH₃) | CH₃ | CH(CH₃) | 3,4-(CH₃)₂C₆H₃ |

TABLE A-continued $$R^1-O-\overset{O}{\underset{}{C}}-NH-\overset{CH(CH_3)_2}{\underset{S}{CH}}-\overset{O}{\underset{}{C}}-NH-A-\overset{Y}{\underset{}{C}}=N-O-Z-Ar$$

(I')

| No. | R¹ | A | Y | Z | Ar |
|---|---|---|---|---|---|
| 1.1241 | CH(CH₃)₂ | CH(CH₃) | CH₃ | CH(CH₃) | 4-NO₂—C₆H₄ |
| 1.1242 | CH(CH₃)C₂H₅ | CH(CH₃) | CH₃ | CH(CH₃) | 4-Cl—C₆H₄ |
| 1.1243 | CH(CH₃)C₂H₅ | CH(CH₃) | CH₃ | CH(CH₃) | 4-CH₃—C₆H₄ |
| 1.1244 | CH(CH₃)C₂H₅ | CH(CH₃) | CH₃ | CH(CH₃) | 4-CH₃O—C₆H₄ |
| 1.1245 | CH(CH₃)C₂H₅ | CH(CH₃) | CH₃ | CH(CH₃) | 4-CN—C₆H₄ |
| 1.1246 | CH(CH₃)C₂H₅ | CH(CH₃) | CH₃ | CH(CH₃) | 3-Cl—C₆H₄ |
| 1.1247 | CH(CH₃)C₂H₅ | CH(CH₃) | CH₃ | CH(CH₃) | 3-CH₃—C₆H₄ |
| 1.1248 | CH(CH₃)C₂H₅ | CH(CH₃) | CH₃ | CH(CH₃) | 3-CH₃O—C₆H₄ |
| 1.1249 | CH(CH₃)C₂H₅ | CH(CH₃) | CH₃ | CH(CH₃) | 3-CN—C₆H₄ |
| 1.1250 | CH(CH₃)C₂H₅ | CH(CH₃) | CH₃ | CH(CH₃) | 2-Cl—C₆H₄ |
| 1.1251 | CH(CH₃)C₂H₅ | CH(CH₃) | CH₃ | CH(CH₃) | 2-CH₃—C₆H₄ |
| 1.1252 | CH(CH₃)C₂H₅ | CH(CH₃) | CH₃ | CH(CH₃) | 2-CH₃O—C₆H₄ |
| 1.1253 | CH(CH₃)C₂H₅ | CH(CH₃) | CH₃ | CH(CH₃) | 2-CN—C₆H₄ |
| 1.1254 | CH(CH₃)C₂H₅ | CH(CH₃) | CH₃ | CH(CH₃) | 3,4-(CH₃O)₂C₆H₃ |
| 1.1255 | CH(CH₃)C₂H₅ | CH(CH₃) | CH₃ | CH(CH₃) | 2,4-Cl₂—C₆H₃ |
| 1.1256 | CH(CH₃)C₂H₅ | CH(CH₃) | CH₃ | CH(CH₃) | 2,4-(CH₃)₂—C₆H₃ |
| 1.1257 | CH(CH₃)C₂H₅ | CH(CH₃) | CH₃ | CH(CH₃) | 3,4-(CH₃)₂C₆H₃ |
| 1.1258 | CH(CH₃)C₂H₅ | CH(CH₃) | CH₃ | CH(CH₃) | 4-NO₂—C₆H₄ |
| 1.1259 | C(CH₃)₃ | CH(CH₃) | CH₃ | CH(CH₃) | 4-Cl—C₆H₄ |
| 1.1260 | C(CH₃)₃ | CH(CH₃) | CH₃ | CH(CH₃) | 4-CH₃—C₆H₄ |
| 1.1261 | C(CH₃)₃ | CH(CH₃) | CH₃ | CH(CH₃) | 4-CH₃O—C₆H₄ |
| 1.1262 | C(CH₃)₃ | CH(CH₃) | CH₃ | CH(CH₃) | 4-CN—C₆H₄ |
| 1.1263 | C(CH₃)₃ | CH(CH₃) | CH₃ | CH(CH₃) | 3-Cl—C₆H₄ |
| 1.1264 | C(CH₃)₃ | CH(CH₃) | CH₃ | CH(CH₃) | 3-CH₃—C₆H₄ |
| 1.1265 | C(CH₃)₃ | CH(CH₃) | CH₃ | CH(CH₃) | 3-CH₃O—C₆H₄ |
| 1.1266 | C(CH₃)₃ | CH(CH₃) | CH₃ | CH(CH₃) | 3-CN—C₆H₄ |
| 1.1267 | C(CH₃)₃ | CH(CH₃) | CH₃ | CH(CH₃) | 2-Cl—C₆H₄ |
| 1.1268 | C(CH₃)₃ | CH(CH₃) | CH₃ | CH(CH₃) | 2-CH₃—C₆H₄ |
| 1.1269 | C(CH₃)₃ | CH(CH₃) | CH₃ | CH(CH₃) | 2-CH₃O—C₆H₄ |
| 1.1270 | C(CH₃)₃ | CH(CH₃) | CH₃ | CH(CH₃) | 2-CN—C₆H₄ |
| 1.1271 | C(CH₃)₃ | CH(CH₃) | CH₃ | CH(CH₃) | 3,4-(CH₃O)₂C₆H₃ |
| 1.1272 | C(CH₃)₃ | CH(CH₃) | CH₃ | CH(CH₃) | 2,4-Cl₂—C₆H₃ |
| 1.1273 | C(CH₃)₃ | CH(CH₃) | CH₃ | CH(CH₃) | 2,4-(CH₃)₂—C₆H₃ |
| 1.1274 | C(CH₃)₃ | CH(CH₃) | CH₃ | CH(CH₃) | 3,4-(CH₃)₂C₆H₃ |
| 1.1275 | C(CH₃)₃ | CH(CH₃) | CH₃ | CH(CH₃) | 4-NO₂—C₆H₄ |
| 1.1276 | CH(CH₃)₂ | C(CH₃)₂—CH₂ | CH₃ | CH(CH₃) | 4-Cl—C₆H₄ |
| 1.1277 | CH(CH₃)₂ | C(CH₃)₂—CH₂ | CH₃ | CH(CH₃) | 4-CH₃—C₆H₄ |
| 1.1278 | CH(CH₃)₂ | C(CH₃)₂—CH₂ | CH₃ | CH(CH₃) | 4-CH₃O—C₆H₄ |
| 1.1279 | CH(CH₃)₂ | C(CH₃)₂—CH₂ | CH₃ | CH(CH₃) | 4-CN—C₆H₄ |
| 1.1280 | CH(CH₃)₂ | C(CH₃)₂—CH₂ | CH₃ | CH(CH₃) | 3-Cl—C₆H₄ |
| 1.1281 | CH(CH₃)₂ | C(CH₃)₂—CH₂ | CH₃ | CH(CH₃) | 3-CH₃—C₆H₄ |
| 1.1282 | CH(CH₃)₂ | C(CH₃)₂—CH₂ | CH₃ | CH(CH₃) | 3-CH₃O—C₆H₄ |
| 1.1283 | CH(CH₃)₂ | C(CH₃)₂—CH₂ | CH₃ | CH(CH₃) | 3-CN—C₆H₄ |
| 1.1284 | CH(CH₃)₂ | C(CH₃)₂—CH₂ | CH₃ | CH(CH₃) | 2-Cl—C₆H₄ |
| 1.1285 | CH(CH₃)₂ | C(CH₃)₂—CH₂ | CH₃ | CH(CH₃) | 2-CH₃—C₆H₄ |
| 1.1286 | CH(CH₃)₂ | C(CH₃)₂—CH₂ | CH₃ | CH(CH₃) | 2-CH₃O—C₆H₄ |
| 1.1287 | CH(CH₃)₂ | C(CH₃)₂—CH₂ | CH₃ | CH(CH₃) | 2-CN—C₆H₄ |
| 1.1288 | CH(CH₃)₂ | C(CH₃)₂—CH₂ | CH₃ | CH(CH₃) | 3,4-(CH₃O)₂C₆H₃ |
| 1.1289 | CH(CH₃)₂ | C(CH₃)₂—CH₂ | CH₃ | CH(CH₃) | 2,4-Cl₂—C₆H₃ |
| 1.1290 | CH(CH₃)₂ | C(CH₃)₂—CH₂ | CH₃ | CH(CH₃) | 2,4-(CH₃)₂—C₆H₃ |
| 1.1291 | CH(CH₃)₂ | C(CH₃)₂—CH₂ | CH₃ | CH(CH₃) | 3,4-(CH₃)₂C₆H₃ |
| 1.1292 | CH(CH₃)₂ | C(CH₃)₂—CH₂ | CH₃ | CH(CH₃) | 4-NO₂—C₆H₄ |
| 1.1293 | CH(CH₃)C₂H₅ | C(CH₃)₂—CH₂ | CH₃ | CH(CH₃) | 4-Cl—C₆H₄ |
| 1.1294 | CH(CH₃)C₂H₅ | C(CH₃)₂—CH₂ | CH₃ | CH(CH₃) | 4-CH₃—C₆H₄ |
| 1.1295 | CH(CH₃)C₂H₅ | C(CH₃)₂—CH₂ | CH₃ | CH(CH₃) | 4-CH₃—C₆H₄ |
| 1.1296 | CH(CH₃)C₂H₅ | C(CH₃)₂—CH₂ | CH₃ | CH(CH₃) | 4-CN—C₆H₄ |
| 1.1297 | CH(CH₃)C₂H₅ | C(CH₃)₂—CH₂ | CH₃ | CH(CH₃) | 3-Cl—C₆H₄ |
| 1.1298 | CH(CH₃)C₂H₅ | C(CH₃)₂—CH₂ | CH₃ | CH(CH₃) | 3-CH₃—C₆H₄ |
| 1.1299 | CH(CH₃)C₂H₅ | C(CH₃)₂—CH₂ | CH₃ | CH(CH₃) | 3-CH₃O—C₆H₄ |
| 1.1300 | CH(CH₃)C₂H₅ | C(CH₃)₂—CH₂ | CH₃ | CH(CH₃) | 3-CN—C₆H₄ |
| 1.1301 | CH(CH₃)C₂H₅ | C(CH₃)₂—CH₂ | CH₃ | CH(CH₃) | 2-Cl—C₆H₄ |
| 1.1302 | CH(CH₃)C₂H₅ | C(CH₃)₂—CH₂ | CH₃ | CH(CH₃) | 2-CH₃—C₆H₄ |
| 1.1303 | CH(CH₃)C₂H₅ | C(CH₃)₂—CH₂ | CH₃ | CH(CH₃) | 2-CH₃O—C₆H₄ |
| 1.1304 | CH(CH₃)C₂H₅ | C(CH₃)₂—CH₂ | CH₃ | CH(CH₃) | 2-CN—C₆H₄ |
| 1.1305 | CH(CH₃)C₂H₅ | C(CH₃)₂—CH₂ | CH₃ | CH(CH₃) | 3,4-(CH₃O)₂C₆H₃ |
| 1.1306 | CH(CH₃)C₂H₅ | C(CH₃)₂—CH₂ | CH₃ | CH(CH₃) | 2,4-Cl₂—C₆H₃ |
| 1.1307 | CH(CH₃)C₂H₅ | C(CH₃)₂—CH₂ | CH₃ | CH(CH₃) | 2,4-(CH₃)₂—C₆H₃ |
| 1.1308 | CH(CH₃)C₂H₅ | C(CH₃)₂—CH₂ | CH₃ | CH(CH₃) | 3,4-(CH₃)₂C₆H₃ |
| 1.1309 | CH(CH₃)C₂H₅ | C(CH₃)₂—CH₂ | CH₃ | CH(CH₃) | 4-NO₂—C₆H₄ |
| 1.1310 | C(CH₃)₃ | C(CH₃)₂—CH₂ | CH₃ | CH(CH₃) | 4-Cl—C₆H₄ |

TABLE A-continued $$R^1-O-\overset{O}{\underset{S}{C}}-NH-\overset{CH(CH_3)_2}{\underset{}{CH}}-\overset{O}{C}-NH-A-\overset{Y}{\underset{}{C}}=N-O-Z-Ar \qquad (I')$$

| No. | R¹ | A | Y | Z | Ar |
|---|---|---|---|---|---|
| 1.1311 | C(CH₃)₃ | C(CH₃)₂—CH₂ | CH₃ | CH(CH₃) | 4-CH₃—C₆H₄ |
| 1.1312 | C(CH₃)₃ | C(CH₃)₂—CH₂ | CH₃ | CH(CH₃) | 4-CH₃O—C₆H₄ |
| 1.1313 | C(CH₃)₃ | C(CH₃)₂—CH₂ | CH₃ | CH(CH₃) | 4-CN—C₆H₄ |
| 1.1314 | C(CH₃)₃ | C(CH₃)₂—CH₂ | CH₃ | CH(CH₃) | 3-Cl—C₆H₄ |
| 1.1315 | C(CH₃)₃ | C(CH₃)₂—CH₂ | CH₃ | CH(CH₃) | 3-CH₃—C₆H₄ |
| 1.1316 | C(CH₃)₃ | C(CH₃)₂—CH₂ | CH₃ | CH(CH₃) | 3-CH₃O—C₆H₄ |
| 1.1317 | C(CH₃)₃ | C(CH₃)₂—CH₂ | CH₃ | CH(CH₃) | 3-CN—C₆H₄ |
| 1.1318 | C(CH₃)₃ | C(CH₃)₂—CH₂ | CH₃ | CH(CH₃) | 2-Cl—C₆H₄ |
| 1.1319 | C(CH₃)₃ | C(CH₃)₂—CH₂ | CH₃ | CH(CH₃) | 2-CH₃—C₆H₄ |
| 1.1320 | C(CH₃)₃ | C(CH₃)₂—CH₂ | CH₃ | CH(CH₃) | 2-CH₃O—C₆H₄ |
| 1.1321 | C(CH₃)₃ | C(CH₃)₂—CH₂ | CH₃ | CH(CH₃) | 2-CN—C₆H₄ |
| 1.1322 | C(CH₃)₃ | C(CH₃)₂—CH₂ | CH₃ | CH(CH₃) | 3,4-(CH₃O)₂C₆H₃ |
| 1.1323 | C(CH₃)₃ | C(CH₃)₂—CH₂ | CH₃ | CH(CH₃) | 2,4-Cl₂—C₆H₃ |
| 1.1324 | C(CH₃)₃ | C(CH₃)₂—CH₂ | CH₃ | CH(CH₃) | 2,4-(CH₃)₂—C₆H₃ |
| 1.1325 | C(CH₃)₃ | C(CH₃)₂—CH₂ | CH₃ | CH(CH₃) | 3,4-(CH₃)₂C₆H₃ |
| 1.1326 | C(CH₃)₃ | C(CH₃)₂—CH₂ | CH₃ | CH(CH₃) | 4-NO₂—C₆H₄ |
| 1.1327 | CH(CH₃)₂ | CH(CH₃) | H | CH(CH₃) | 4-Cl—C₆H₄ |
| 1.1328 | CH(CH₃)₂ | CH(CH₃) | H | CH(CH₃) | 4-CH₃—C₆H₄ |
| 1.1329 | CH(CH₃)₂ | CH(CH₃) | H | CH(CH₃) | 4-CH₃O—C₆H₄ |
| 1.1330 | CH(CH₃)₂ | CH(CH₃) | H | CH(CH₃) | 4-CN—C₆H₄ |
| 1.1331 | CH(CH₃)₂ | CH(CH₃) | H | CH(CH₃) | 3-Cl—C₆H₄ |
| 1.1332 | CH(CH₃)₂ | CH(CH₃) | H | CH(CH₃) | 3-CH₃—C₆H₄ |
| 1.1333 | CH(CH₃)₂ | CH(CH₃) | H | CH(CH₃) | 3-CH₃O—C₆H₄ |
| 1.1334 | CH(CH₃)₂ | CH(CH₃) | H | CH(CH₃) | 3-CN—C₆H₄ |
| 1.1335 | CH(CH₃)₂ | CH(CH₃) | H | CH(CH₃) | 2-Cl—C₆H₄ |
| 1.1336 | CH(CH₃)₂ | CH(CH₃) | H | CH(CH₃) | 2-CH₃—C₆H₄ |
| 1.1337 | CH(CH₃)₂ | CH(CH₃) | H | CH(CH₃) | 2-CH₃O—C₆H₄ |
| 1.1338 | CH(CH₃)₂ | CH(CH₃) | H | CH(CH₃) | 2-CN—C₆H₄ |
| 1.1339 | CH(CH₃)₂ | CH(CH₃) | H | CH(CH₃) | 3,4-(CH₃O)₂C₆H₃ |
| 1.1340 | CH(CH₃)₂ | CH(CH₃) | H | CH(CH₃) | 2,4-Cl₂—C₆H₃ |
| 1.1341 | CH(CH₃)₂ | CH(CH₃) | H | CH(CH₃) | 2,4-(CH₃)₂—C₆H₃ |
| 1.1342 | CH(CH₃)₂ | CH(CH₃) | H | CH(CH₃) | 3,4-(CH₃)₂C₆H₃ |
| 1.1343 | CH(CH₃)₂ | CH(CH₃) | H | CH(CH₃) | 4-NO₂—C₆H₄ |
| 1.1344 | CH(CH₃)C₂H₅ | CH(CH₃) | H | CH(CH₃) | 4-Cl—C₆H₄ |
| 1.1345 | CH(CH₃)C₂H₅ | CH(CH₃) | H | CH(CH₃) | 4-CH₃—C₆H₄ |
| 1.1346 | CH(CH₃)C₂H₅ | CH(CH₃) | H | CH(CH₃) | 4-CH₃O—C₆H₄ |
| 1.1347 | CH(CH₃)C₂H₅ | CH(CH₃) | H | CH(CH₃) | 4-CN—C₆H₄ |
| 1.1348 | CH(CH₃)C₂H₅ | CH(CH₃) | H | CH(CH₃) | 3-Cl—C₆H₄ |
| 1.1349 | CH(CH₃)C₂H₅ | CH(CH₃) | H | CH(CH₃) | 3-CH₃—C₆H₄ |
| 1.1350 | CH(CH₃)C₂H₅ | CH(CH₃) | H | CH(CH₃) | 3-CH₃O—C₆H₄ |
| 1.1351 | CH(CH₃)C₂H₅ | CH(CH₃) | H | CH(CH₃) | 3-CN—C₆H₄ |
| 1.1352 | CH(CH₃)C₂H₅ | CH(CH₃) | H | CH(CH₃) | 2-Cl—C₆H₄ |
| 1.1353 | CH(CH₃)C₂H₅ | CH(CH₃) | H | CH(CH₃) | 2-CH₃—C₆H₄ |
| 1.1354 | CH(CH₃)C₂H₅ | CH(CH₃) | H | CH(CH₃) | 2-CH₃O—C₆H₄ |
| 1.1355 | CH(CH₃)C₂H₅ | CH(CH₃) | H | CH(CH₃) | 2-CN—C₆H₄ |
| 1.1356 | CH(CH₃)C₂H₅ | CH(CH₃) | H | CH(CH₃) | 3,4-(CH₃O)₂C₆H₃ |
| 1.1357 | CH(CH₃)C₂H₅ | CH(CH₃) | H | CH(CH₃) | 2,4-Cl₂—C₆H₃ |
| 1.1358 | CH(CH₃)C₂H₅ | CH(CH₃) | H | CH(CH₃) | 2,4-(CH₃)₂—C₆H₃ |
| 1.1359 | CH(CH₃)C₂H₅ | CH(CH₃) | H | CH(CH₃) | 3,4-(CH₃)₂C₆H₃ |
| 1.1360 | CH(CH₃)C₂H₅ | CH(CH₃) | H | CH(CH₃) | 4-NO₂—C₆H₄ |
| 1.1361 | C(CH₃)₃ | CH(CH₃) | H | CH(CH₃) | 4-Cl—C₆H₄ |
| 1.1362 | C(CH₃)₃ | CH(CH₃) | H | CH(CH₃) | 4-CH₃—C₆H₄ |
| 1.1363 | C(CH₃)₃ | CH(CH₃) | H | CH(CH₃) | 4-CH₃O—C₆H₄ |
| 1.1364 | C(CH₃)₃ | CH(CH₃) | H | CH(CH₃) | 4-CN—C₆H₄ |
| 1.1365 | C(CH₃)₃ | CH(CH₃) | H | CH(CH₃) | 3-Cl—C₆H₄ |
| 1.1366 | C(CH₃)₃ | CH(CH₃) | H | CH(CH₃) | 3-CH₃—C₆H₄ |
| 1.1367 | C(CH₃)₃ | CH(CH₃) | H | CH(CH₃) | 3-CH₃O—C₆H₄ |
| 1.1368 | C(CH₃)₃ | CH(CH₃) | H | CH(CH₃) | 3-CN—C₆H₄ |
| 1.1369 | C(CH₃)₃ | CH(CH₃) | H | CH(CH₃) | 2-Cl—C₆H₄ |
| 1.1370 | C(CH₃)₃ | CH(CH₃) | H | CH(CH₃) | 2-CH₃—C₆H₄ |
| 1.1371 | C(CH₃)₃ | CH(CH₃) | H | CH(CH₃) | 2-CH₃O—C₆H₄ |
| 1.1372 | C(CH₃)₃ | CH(CH₃) | H | CH(CH₃) | 2-CN—C₆H₄ |
| 1.1373 | C(CH₃)₃ | CH(CH₃) | H | CH(CH₃) | 3,4-(CH₃O)₂C₆H₃ |
| 1.1374 | C(CH₃)₃ | CH(CH₃) | H | CH(CH₃) | 2,4-Cl₂—C₆H₃ |
| 1.1375 | C(CH₃)₃ | CH(CH₃) | H | CH(CH₃) | 2,4-(CH₃)₂—C₆H₃ |
| 1.1376 | C(CH₃)₃ | CH(CH₃) | H | CH(CH₃) | 3,4-(CH₃)₂C₆H₃ |
| 1.1377 | C(CH₃)₃ | CH(CH₃) | H | CH(CH₃) | 4-NO₂—C₆H₄ |
| 1.1378 | CH(CH₃)₂ | C(CH₃)₂—CH₂ | H | CH(CH₃) | 4-Cl—C₆H₄ |
| 1.1379 | CH(CH₃)₂ | C(CH₃)₂—CH₂ | H | CH(CH₃) | 4-CH₃—C₆H₄ |
| 1.1380 | CH(CH₃)₂ | C(CH₃)₂—CH₂ | H | CH(CH₃) | 4-CH₃O—C₆H₄ |

TABLE A-continued $$R^1-O-\overset{O}{\underset{}{C}}-NH-\overset{CH(CH_3)_2}{\underset{S}{CH}}-\overset{O}{\underset{}{C}}-NH-A-\overset{Y}{\underset{}{C}}=N-O-Z-Ar \quad (I')$$

| No. | R$^1$ | A | Y | Z | Ar |
|---|---|---|---|---|---|
| 1.1381 | CH(CH$_3$)$_2$ | C(CH$_3$)$_2$—CH$_2$ | H | CH(CH$_3$) | 4-CN—C$_6$H$_4$ |
| 1.1382 | CH(CH$_3$)$_2$ | C(CH$_3$)$_2$—CH$_2$ | H | CH(CH$_3$) | 3-Cl—C$_6$H$_4$ |
| 1.1383 | CH(CH$_3$)$_2$ | C(CH$_3$)$_2$—CH$_2$ | H | CH(CH$_3$) | 3-CH$_3$—C$_6$H$_4$ |
| 1.1384 | CH(CH$_3$)$_2$ | C(CH$_3$)$_2$—CH$_2$ | H | CH(CH$_3$) | 3-CH$_3$O—C$_6$H$_4$ |
| 1.1385 | CH(CH$_3$)$_2$ | C(CH$_3$)$_2$—CH$_2$ | H | CH(CH$_3$) | 3-CN—C$_6$H$_4$ |
| 1.1386 | CH(CH$_3$)$_2$ | C(CH$_3$)$_2$—CH$_2$ | H | CH(CH$_3$) | 2-Cl—C$_6$H$_4$ |
| 1.1387 | CH(CH$_3$)$_2$ | C(CH$_3$)$_2$—CH$_2$ | H | CH(CH$_3$) | 2-CH$_3$—C$_6$H$_4$ |
| 1.1388 | CH(CH$_3$)$_2$ | C(CH$_3$)$_2$—CH$_2$ | H | CH(CH$_3$) | 2-CH$_3$O—C$_6$H$_4$ |
| 1.1389 | CH(CH$_3$)$_2$ | C(CH$_3$)$_2$—CH$_2$ | H | CH(CH$_3$) | 2-CN—C$_6$H$_4$ |
| 1.1390 | CH(CH$_3$)$_2$ | C(CH$_3$)$_2$—CH$_2$ | H | CH(CH$_3$) | 3,4-(CH$_3$O)$_2$C$_6$H$_3$ |
| 1.1391 | CH(CH$_3$)$_2$ | C(CH$_3$)$_2$—CH$_2$ | H | CH(CH$_3$) | 2,4-Cl$_2$—C$_6$H$_3$ |
| 1.1392 | CH(CH$_3$)$_2$ | C(CH$_3$)$_2$—CH$_2$ | H | CH(CH$_3$) | 2,4-(CH$_3$)$_2$—C$_6$H$_3$ |
| 1.1393 | CH(CH$_3$)$_2$ | C(CH$_3$)$_2$—CH$_2$ | H | CH(CH$_3$) | 3,4-(CH$_3$)$_2$C$_6$H$_3$ |
| 1.1394 | CH(CH$_3$)$_2$ | C(CH$_3$)$_2$—CH$_2$ | H | CH(CH$_3$) | 4-NO$_2$—C$_6$H$_4$ |
| 1.1395 | CH(CH$_3$)C$_2$H$_5$ | C(CH$_3$)$_2$—CH$_2$ | H | CH(CH$_3$) | 4-Cl—C$_6$H$_4$ |
| 1.1396 | CH(CH$_3$)C$_2$H$_5$ | C(CH$_3$)$_2$—CH$_2$ | H | CH(CH$_3$) | 4-CH$_3$—C$_6$H$_4$ |
| 1.1397 | CH(CH$_3$)C$_2$H$_5$ | C(CH$_3$)$_2$—CH$_2$ | H | CH(CH$_3$) | 4-CH$_3$O—C$_6$H$_4$ |
| 1.1398 | CH(CH$_3$)C$_2$H$_5$ | C(CH$_3$)$_2$—CH$_2$ | H | CH(CH$_3$) | 4-CN—C$_6$H$_4$ |
| 1.1399 | CH(CH$_3$)C$_2$H$_5$ | C(CH$_3$)$_2$—CH$_2$ | H | CH(CH$_3$) | 3-Cl—C$_6$H$_4$ |
| 1.1400 | CH(CH$_3$)C$_2$H$_5$ | C(CH$_3$)$_2$—CH$_2$ | H | CH(CH$_3$) | 3-CH$_3$—C$_6$H$_4$ |
| 1.1401 | CH(CH$_3$)C$_2$H$_5$ | C(CH$_3$)$_2$—CH$_2$ | H | CH(CH$_3$) | 3-CH$_3$O—C$_6$H$_4$ |
| 1.1402 | CH(CH$_3$)C$_2$H$_5$ | C(CH$_3$)$_2$—CH$_2$ | H | CH(CH$_3$) | 3-CN—C$_6$H$_4$ |
| 1.1403 | CH(CH$_3$)C$_2$H$_5$ | C(CH$_3$)$_2$—CH$_2$ | H | CH(CH$_3$) | 2-Cl—C$_6$H$_4$ |
| 1.1404 | CH(CH$_3$)C$_2$H$_5$ | C(CH$_3$)$_2$—CH$_2$ | H | CH(CH$_3$) | 2-CH$_3$—C$_6$H$_4$ |
| 1.1405 | CH(CH$_3$)C$_2$H$_5$ | C(CH$_3$)$_2$—CH$_2$ | H | CH(CH$_3$) | 2-CH$_3$O—C$_6$H$_4$ |
| 1.1406 | CH(CH$_3$)C$_2$H$_5$ | C(CH$_3$)$_2$—CH$_2$ | H | CH(CH$_3$) | 2-CN—C$_6$H$_4$ |
| 1.1407 | CH(CH$_3$)C$_2$H$_5$ | C(CH$_3$)$_2$—CH$_2$ | H | CH(CH$_3$) | 3,4-(CH$_3$O)$_2$C$_6$H$_3$ |
| 1.1408 | CH(CH$_3$)C$_2$H$_5$ | C(CH$_3$)$_2$—CH$_2$ | H | CH(CH$_3$) | 2,4-Cl$_2$—C$_6$H$_3$ |
| 1.1409 | CH(CH$_3$)C$_2$H$_5$ | C(CH$_3$)$_2$—CH$_2$ | H | CH(CH$_3$) | 2,4-(CH$_3$)$_2$—C$_6$H$_3$ |
| 1.1410 | CH(CH$_3$)C$_2$H$_5$ | C(CH$_3$)$_2$—CH$_2$ | H | CH(CH$_3$) | 3,4-(CH$_3$)$_2$C$_6$H$_3$ |
| 1.1411 | CH(CH$_3$)C$_2$H$_5$ | C(CH$_3$)$_2$—CH$_2$ | H | CH(CH$_3$) | 4-NO$_2$—C$_6$H$_4$ |
| 1.1412 | C(CH$_3$)$_3$ | C(CH$_3$)$_2$—CH$_2$ | H | CH(CH$_3$) | 4-Cl—C$_6$H$_4$ |
| 1.1413 | C(CH$_3$)$_3$ | C(CH$_3$)$_2$—CH$_2$ | H | CH(CH$_3$) | 4-CH$_3$—C$_6$H$_4$ |
| 1.1414 | C(CH$_3$)$_3$ | C(CH$_3$)$_2$—CH$_2$ | H | CH(CH$_3$) | 4-CH$_3$O—C$_6$H$_4$ |
| 1.1415 | C(CH$_3$)$_3$ | C(CH$_3$)$_2$—CH$_2$ | H | CH(CH$_3$) | 4-CN—C$_6$H$_4$ |
| 1.1416 | C(CH$_3$)$_3$ | C(CH$_3$)$_2$—CH$_2$ | H | CH(CH$_3$) | 3-Cl—C$_6$H$_4$ |
| 1.1417 | C(CH$_3$)$_3$ | C(CH$_3$)$_2$—CH$_2$ | H | CH(CH$_3$) | 3-CH$_3$—C$_6$H$_4$ |
| 1.1418 | C(CH$_3$)$_3$ | C(CH$_3$)$_2$—CH$_2$ | H | CH(CH$_3$) | 3-CH$_3$O—C$_6$H$_4$ |
| 1.1419 | C(CH$_3$)$_3$ | C(CH$_3$)$_2$—CH$_2$ | H | CH(CH$_3$) | 3-CN—C$_6$H$_4$ |
| 1.1420 | C(CH$_3$)$_3$ | C(CH$_3$)$_2$—CH$_2$ | H | CH(CH$_3$) | 2-Cl—C$_6$H$_4$ |
| 1.1421 | C(CH$_3$)$_3$ | C(CH$_3$)$_2$—CH$_2$ | H | CH(CH$_3$) | 2-CH$_3$—C$_6$H$_4$ |
| 1.1422 | C(CH$_3$)$_3$ | C(CH$_3$)$_2$—CH$_2$ | H | CH(CH$_3$) | 2-CH$_3$O—C$_6$H$_4$ |
| 1.1423 | C(CH$_3$)$_3$ | C(CH$_3$)$_2$—CH$_2$ | H | CH(CH$_3$) | 2-CN—C$_6$H$_4$ |
| 1.1424 | C(CH$_3$)$_3$ | C(CH$_3$)$_2$—CH$_2$ | H | CH(CH$_3$) | 3,4-(CH$_3$O)$_2$C$_6$H$_3$ |
| 1.1425 | C(CH$_3$)$_3$ | C(CH$_3$)$_2$—CH$_2$ | H | CH(CH$_3$) | 2,4-Cl$_2$—C$_6$H$_3$ |
| 1.1426 | C(CH$_3$)$_3$ | C(CH$_3$)$_2$—CH$_2$ | H | CH(CH$_3$) | 2,4-(CH$_3$)$_2$—C$_6$H$_3$ |
| 1.1427 | C(CH$_3$)$_3$ | C(CH$_3$)$_2$—CH$_2$ | H | CH(CH$_3$) | 3,4-(CH$_3$)$_2$C$_6$H$_3$ |
| 1.1428 | C(CH$_3$)$_3$ | C(CH$_3$)$_2$—CH$_2$ | H | CH(CH$_3$) | 4-NO$_2$—C$_6$H$_4$ |
| 1.1429 | CH(CH$_3$)$_2$ | CH$_2$ | CH$_3$ | CH(CH$_3$) | 4-Cl—C$_6$H$_4$ |
| 1.1430 | CH(CH$_3$)$_2$ | CH$_2$ | CH$_3$ | CH(CH$_3$) | 4-CH$_3$—C$_6$H$_4$ |
| 1.1431 | CH(CH$_3$)$_2$ | CH$_2$ | CH$_3$ | CH(CH$_3$) | 4-CH$_3$O—C$_6$H$_4$ |
| 1.1432 | CH(CH$_3$)$_2$ | CH$_2$ | CH$_3$ | CH(CH$_3$) | 4-CN—C$_6$H$_4$ |
| 1.1433 | CH(CH$_3$)$_2$ | CH$_2$ | CH$_3$ | CH(CH$_3$) | 3-Cl—C$_6$H$_4$ |
| 1.1434 | CH(CH$_3$)$_2$ | CH$_2$ | CH$_3$ | CH(CH$_3$) | 3-CH$_3$—C$_6$H$_4$ |
| 1.1435 | CH(CH$_3$)$_2$ | CH$_2$ | CH$_3$ | CH(CH$_3$) | 3-CH$_3$O—C$_6$H$_4$ |
| 1.1436 | CH(CH$_3$)$_2$ | CH$_2$ | CH$_3$ | CH(CH$_3$) | 3-CN—C$_6$H$_4$ |
| 1.1437 | CH(CH$_3$)$_2$ | CH$_2$ | CH$_3$ | CH(CH$_3$) | 2-CL-C$_6$H$_4$ |
| 1.1438 | CH(CH$_3$)$_2$ | CH$_2$ | CH$_3$ | CH(CH$_3$) | 2-CH$_3$—C$_6$H$_4$ |
| 1.1439 | CH(CH$_3$)$_2$ | CH$_2$ | CH$_3$ | CH(CH$_3$) | 2-CH$_3$O—C$_6$H$_4$ |
| 1.1440 | CH(CH$_3$)$_2$ | CH$_2$ | CH$_3$ | CH(CH$_3$) | 2-CN—C$_6$H$_4$ |
| 1.1441 | CH(CH$_3$)$_2$ | CH$_2$ | CH$_3$ | CH(CH$_3$) | 3,4-(CH$_3$O)$_2$C$_6$H$_3$ |
| 1.1442 | CH(CH$_3$)$_2$ | CH$_2$ | CH$_3$ | CH(CH$_3$) | 2,4-Cl$_2$—C$_6$H$_3$ |
| 1.1443 | CH(CH$_3$)$_3$ | CH$_2$ | CH$_3$ | CH(CH$_3$) | 2,4-(CH$_3$)$_2$—C$_6$H$_3$ |
| 1.1444 | CH(CH$_3$)$_3$ | CH$_2$ | CH$_3$ | CH(CH$_3$) | 3,4-(CH$_3$)$_2$C$_6$H$_3$ |
| 1.1445 | CH(CH$_3$)$_3$ | CH$_2$ | CH$_3$ | CH(CH$_3$) | 4-NO$_2$—C$_6$H$_4$ |
| 1.1446 | CH(CH$_3$)C$_2$H$_5$ | CH$_2$ | CH$_3$ | CH(CH$_3$) | 4-Cl—C$_6$H$_4$ |
| 1.1447 | CH(CH$_3$)C$_2$H$_5$ | CH$_2$ | CH$_3$ | CH(CH$_3$) | 4-CH$_3$—C$_6$H$_4$ |
| 1.1448 | CH(CH$_3$)C$_2$H$_5$ | CH$_2$ | CH$_3$ | CH(CH$_3$) | 4-CH$_3$O—C$_6$H$_4$ |
| 1.1449 | CH(CH$_3$)C$_2$H$_5$ | CH$_2$ | CH$_3$ | CH(CH$_3$) | 4-CN—C$_6$H$_4$ |
| 1.1450 | CH(CH$_3$)C$_2$H$_5$ | CH$_2$ | CH$_3$ | CH(CH$_3$) | 3-Cl—C$_6$H$_4$ |

TABLE A-continued $$R^1-O-\overset{O}{C}-NH-\overset{CH(CH_3)_2}{\underset{\underline{S}}{CH}}-\overset{O}{C}-NH-A-\overset{Y}{\underset{}{C}}=N-O-Z-Ar \quad (I')$$

| No. | $R^1$ | A | Y | Z | Ar |
|---|---|---|---|---|---|
| 1.1451 | $CH(CH_3)C_2H_5$ | $CH_2$ | $CH_3$ | $CH(CH_3)$ | $3\text{-}CH_3\text{—}C_6H_4$ |
| 1.1452 | $CH(CH_3)C_2H_5$ | $CH_2$ | $CH_3$ | $CH(CH_3)$ | $3\text{-}CH_3O\text{—}C_6H_4$ |
| 1.1453 | $CH(CH_3)C_2H_5$ | $CH_2$ | $CH_3$ | $CH(CH_3)$ | $3\text{-}CN\text{—}C_6H_4$ |
| 1.1454 | $CH(CH_3)C_2H_5$ | $CH_2$ | $CH_3$ | $CH(CH_3)$ | $2\text{-}Cl\text{—}C_6H_4$ |
| 1.1455 | $CH(CH_3)C_2H_5$ | $CH_2$ | $CH_3$ | $CH(CH_3)$ | $2\text{-}CH_3\text{—}C_6H_4$ |
| 1.1456 | $CH(CH_3)C_2H_5$ | $CH_2$ | $CH_3$ | $CH(CH_3)$ | $2\text{-}CH_3O\text{—}C_6H_4$ |
| 1.1457 | $CH(CH_3)C_2H_5$ | $CH_2$ | $CH_3$ | $CH(CH_3)$ | $2\text{-}CN\text{—}C_6H_4$ |
| 1.1458 | $CH(CH_3)C_2H_5$ | $CH_2$ | $CH_3$ | $CH(CH_3)$ | $3,4\text{-}(CH_3O)_2C_6H_3$ |
| 1.1459 | $CH(CH_3)C_2H_5$ | $CH_2$ | $CH_3$ | $CH(CH_3)$ | $2,4\text{-}Cl_2\text{—}C_6H_3$ |
| 1.1460 | $CH(CH_3)C_2H_5$ | $CH_2$ | $CH_3$ | $CH(CH_3)$ | $2,4\text{-}(CH_3)_2\text{—}C_6H_3$ |
| 1.1461 | $CH(CH_3)C_2H_5$ | $CH_2$ | $CH_3$ | $CH(CH_3)$ | $3,4\text{-}(CH_3)_2C_6H_3$ |
| 1.1462 | $CH(CH_3)C_2H_5$ | $CH_2$ | $CH_3$ | $CH(CH_3)$ | $4\text{-}NO_2\text{—}C_6H_4$ |
| 1.1463 | $C(CH_3)_3$ | $CH_2$ | $CH_3$ | $CH(CH_3)$ | $4\text{-}Cl\text{—}C_6H_4$ |
| 1.1464 | $C(CH_3)_3$ | $CH_2$ | $CH_3$ | $CH(CH_3)$ | $4\text{-}CH_3\text{—}C_6H_4$ |
| 1.1465 | $C(CH_3)_3$ | $CH_2$ | $CH_3$ | $CH(CH_3)$ | $4\text{-}CH_3O\text{—}C_6H_4$ |
| 1.1466 | $C(CH_3)_3$ | $CH_2$ | $CH_3$ | $CH(CH_3)$ | $4\text{-}CN\text{—}C_6H_4$ |
| 1.1467 | $C(CH_3)_3$ | $CH_2$ | $CH_3$ | $CH(CH_3)$ | $3\text{-}Cl\text{—}C_6H_4$ |
| 1.1468 | $C(CH_3)_3$ | $CH_2$ | $CH_3$ | $CH(CH_3)$ | $3\text{-}CH_3\text{—}C_6H_4$ |
| 1.1469 | $C(CH_3)_3$ | $CH_2$ | $CH_3$ | $CH(CH_3)$ | $3\text{-}CH_3O\text{—}C_6H_4$ |
| 1.1470 | $C(CH_3)_3$ | $CH_2$ | $CH_3$ | $CH(CH_3)$ | $3\text{-}CN\text{—}C_6H_4$ |
| 1.1471 | $C(CH_3)_3$ | $CH_2$ | $CH_3$ | $CH(CH_3)$ | $2\text{-}Cl\text{—}C_6H_4$ |
| 1.1472 | $C(CH_3)_3$ | $CH_2$ | $CH_3$ | $CH(CH_3)$ | $2\text{-}CH_3\text{—}C_6H_4$ |
| 1.1473 | $C(CH_3)_3$ | $CH_2$ | $CH_3$ | $CH(CH_3)$ | $2\text{-}CH_3O\text{—}C_6H_4$ |
| 1.1474 | $C(CH_3)_3$ | $CH_2$ | $CH_3$ | $CH(CH_3)$ | $2\text{-}CN\text{—}C_6H_4$ |
| 1.1475 | $C(CH_3)_3$ | $CH_2$ | $CH_3$ | $CH(CH_3)$ | $3,4\text{-}(CH_3O)_2C_6H_3$ |
| 1.1476 | $C(CH_3)_3$ | $CH_2$ | $CH_3$ | $CH(CH_3)$ | $2,4\text{-}Cl_2\text{—}C_6H_3$ |
| 1.1477 | $C(CH_3)_3$ | $CH_2$ | $CH_3$ | $CH(CH_3)$ | $2,4\text{-}(CH_3)_2\text{—}C_6H_3$ |
| 1.1478 | $C(CH_3)_3$ | $CH_2$ | $CH_3$ | $CH(CH_3)$ | $3,4\text{-}(CH_3)_2C_6H_3$ |
| 1.1479 | $C(CH_3)_3$ | $CH_2$ | $CH_3$ | $CH(CH_3)$ | $4\text{-}NO_2\text{—}C_6H_4$ |
| 1.1480 | $CH(CH_3)_2$ | $CH_2$ | H | $CH(CH_3)$ | $4\text{-}Cl\text{—}C_6H_4$ |
| 1.1481 | $CH(CH_3)_2$ | $CH_2$ | H | $CH(CH_3)$ | $4\text{-}CH_3\text{—}C_6H_4$ |
| 1.1482 | $CH(CH_3)_2$ | $CH_2$ | H | $CH(CH_3)$ | $4\text{-}CH_3O\text{—}C_6H_4$ |
| 1.1483 | $CH(CH_3)_2$ | $CH_2$ | H | $CH(CH_3)$ | $4\text{-}CN\text{—}C_6H_4$ |
| 1.1484 | $CH(CH_3)_2$ | $CH_2$ | H | $CH(CH_3)$ | $3\text{-}Cl\text{—}C_6H_4$ |
| 1.1485 | $CH(CH_3)_2$ | $CH_2$ | H | $CH(CH_3)$ | $3\text{-}CH_3\text{—}C_6H_4$ |
| 1.1486 | $CH(CH_3)_2$ | $CH_2$ | H | $CH(CH_3)$ | $3\text{-}CH_3O\text{—}C_6H_4$ |
| 1.1487 | $CH(CH_3)_2$ | $CH_2$ | H | $CH(CH_3)$ | $3\text{-}CN\text{—}C_6H_4$ |
| 1.1488 | $CH(CH_3)_2$ | $CH_2$ | H | $CH(CH_3)$ | $2\text{-}Cl\text{—}C_6H_4$ |
| 1.1489 | $CH(CH_3)_2$ | $CH_2$ | H | $CH(CH_3)$ | $2\text{-}CH_3\text{—}C_6H_4$ |
| 1.1490 | $CH(CH_3)_2$ | $CH_2$ | H | $CH(CH_3)$ | $2\text{-}CH_3O\text{—}C_6H_4$ |
| 1.1491 | $CH(CH_3)_2$ | $CH_2$ | H | $CH(CH_3)$ | $2\text{-}CN\text{—}C_6H_4$ |
| 1.1492 | $CH(CH_3)_2$ | $CH_2$ | H | $CH(CH_3)$ | $3,4\text{-}(CH_3O)_2C_6H_3$ |
| 1.1493 | $CH(CH_3)_2$ | $CH_2$ | H | $CH(CH_3)$ | $2,4\text{-}Cl_2\text{—}C_6H_3$ |
| 1.1494 | $CH(CH_3)_2$ | $CH_2$ | H | $CH(CH_3)$ | $2,4\text{-}(CH_3)_2\text{—}C_6H_3$ |
| 1.1495 | $CH(CH_3)_2$ | $CH_2$ | H | $CH(CH_3)$ | $3,4\text{-}(CH_3)_2C_6H_3$ |
| 1.1496 | $CH(CH_3)_2$ | $CH_2$ | H | $CH(CH_3)$ | $4\text{-}NO_2\text{—}C_6H_4$ |
| 1.1497 | $CH(CH_3)C_2H_5$ | $CH_2$ | H | $CH(CH_3)$ | $4\text{-}Cl\text{—}C_6H_4$ |
| 1.1498 | $CH(CH_3)C_2H_5$ | $CH_2$ | H | $CH(CH_3)$ | $4\text{-}CH_3\text{—}C_6H_4$ |
| 1.1499 | $CH(CH_3)C_2H_5$ | $CH_2$ | H | $CH(CH_3)$ | $4\text{-}CH_3O\text{—}C_6H_4$ |
| 1.1500 | $CH(CH_3)C_2H_5$ | $CH_2$ | H | $CH(CH_3)$ | $4\text{-}CN\text{—}C_6H_4$ |
| 1.1501 | $CH(CH_3)C_2H_5$ | $CH_2$ | H | $CH(CH_3)$ | $3\text{-}Cl\text{—}C_6H_4$ |
| 1.1502 | $CH(CH_3)C_2H_5$ | $CH_2$ | H | $CH(CH_3)$ | $3\text{-}CH_3\text{—}C_6H_4$ |
| 1.1503 | $CH(CH_3)C_2H_5$ | $CH_2$ | H | $CH(CH_3)$ | $3\text{-}CH_3O\text{—}C_6H_4$ |
| 1.1504 | $CH(CH_3)C_2H_5$ | $CH_2$ | H | $CH(CH_3)$ | $3\text{-}CN\text{—}C_6H_4$ |
| 1.1505 | $CH(CH_3)C_2H_5$ | $CH_2$ | H | $CH(CH_3)$ | $2\text{-}Cl\text{—}C_6H_4$ |
| 1.1506 | $CH(CH_3)C_2H_5$ | $CH_2$ | H | $CH(CH_3)$ | $2\text{-}CH_3\text{—}C_6H_4$ |
| 1.1507 | $CH(CH_3)C_2H_5$ | $CH_2$ | H | $CH(CH_3)$ | $2\text{-}CH_3O\text{—}C_6H_4$ |
| 1.1508 | $CH(CH_3)C_2H_5$ | $CH_2$ | H | $CH(CH_3)$ | $2\text{-}CN\text{—}C_6H_4$ |
| 1.1509 | $CH(CH_3)C_2H_5$ | $CH_2$ | H | $CH(CH_3)$ | $3,4\text{-}(CH_3O)_2C_6H_3$ |
| 1.1510 | $CH(CH_3)C_2H_5$ | $CH_2$ | H | $CH(CH_3)$ | $2,4\text{-}Cl_2\text{—}C_6H_3$ |
| 1.1511 | $CH(CH_3)C_2H_5$ | $CH_2$ | H | $CH(CH_3)$ | $2,4\text{-}(CH_3)_2\text{—}C_6H_3$ |
| 1.1512 | $CH(CH_3)C_2H_5$ | $CH_2$ | H | $CH(CH_3)$ | $3,4\text{-}(CH_3)_2C_6H_3$ |
| 1.1513 | $CH(CH_3)C_2H_5$ | $CH_2$ | H | $CH(CH_3)$ | $4\text{-}NO_2\text{—}C_6H_4$ |
| 1.1514 | $C(CH_3)_3$ | $CH_2$ | H | $CH(CH_3)$ | $4\text{-}Cl\text{—}C_6H_4$ |
| 1.1515 | $C(CH_3)_3$ | $CH_2$ | H | $CH(CH_3)$ | $4\text{-}CH_3\text{—}C_6H_4$ |
| 1.1516 | $C(CH_3)_3$ | $CH_2$ | H | $CH(CH_3)$ | $4\text{-}CH_3O\text{—}C_6H_4$ |
| 1.1517 | $C(CH_3)_3$ | $CH_2$ | H | $CH(CH_3)$ | $4\text{-}CN\text{—}C_6H_4$ |
| 1.1518 | $C(CH_3)_3$ | $CH_2$ | H | $CH(CH_3)$ | $3\text{-}Cl\text{—}C_6H_4$ |
| 1.1519 | $C(CH_3)_3$ | $CH_2$ | H | $CH(CH_3)$ | $3\text{-}CH_3\text{—}C_6H_4$ |
| 1.1520 | $C(CH_3)_3$ | $CH_2$ | H | $CH(CH_3)$ | $3\text{-}CH_3O\text{—}C_6H_4$ |

TABLE A-continued $$R^1-O-\underset{O}{\overset{O}{C}}-NH-\underset{\underline{S}}{\overset{CH(CH_3)_2}{CH}}-\underset{O}{\overset{O}{C}}-NH-A-\underset{\overset{|}{Y}}{C}=N-O-Z-Ar \quad (I')$$

| No. | R¹ | A | Y | Z | Ar |
|---|---|---|---|---|---|
| 1.1521 | C(CH$_3$)$_3$ | CH$_2$ | H | CH(CH$_3$) | 3-CN—C$_6$H$_4$ |
| 1.1522 | C(CH$_3$)$_3$ | CH$_2$ | H | CH(CH$_3$) | 2-Cl—C$_6$H$_4$ |
| 1.1523 | C(CH$_3$)$_3$ | CH$_2$ | H | CH(CH$_3$) | 2-CH$_3$—C$_6$H$_4$ |
| 1.1524 | C(CH$_3$)$_3$ | CH$_2$ | H | CH(CH$_3$) | 2-CH$_3$O—C$_6$H$_4$ |
| 1.1525 | C(CH$_3$)$_3$ | CH$_2$ | H | CH(CH$_3$) | 2-CN—C$_6$H$_4$ |
| 1.1526 | C(CH$_3$)$_3$ | CH$_2$ | H | CH(CH$_3$) | 3,4-(CH$_3$O)$_2$C$_6$H$_3$ |
| 1.1527 | C(CH$_3$)$_3$ | CH$_2$ | H | CH(CH$_3$) | 2,4-Cl$_2$—C$_6$H$_3$ |
| 1.1528 | C(CH$_3$)$_3$ | CH$_2$ | H | CH(CH$_3$) | 2,4-(CH$_3$)$_2$—C$_6$H$_3$ |
| 1.1529 | C(CH$_3$)$_3$ | CH$_2$ | H | CH(CH$_3$) | 3,4-(CH$_3$)$_2$C$_6$H$_3$ |
| 1.1530 | C(CH$_3$)$_3$ | CH$_2$ | H | CH(CH$_3$) | 4-NO$_2$—C$_6$H$_4$ |
| 1.1531 | CH(CH$_3$)$_2$ | CH(CH$_3$) | CH$_3$ | CH(CH$_3$)CH$_2$ | 4-Cl—C$_6$H$_4$ |
| 1.1532 | CH(CH$_3$)$_2$ | CH(CH$_3$) | CH$_3$ | CH(CH$_3$)CH$_2$ | 4-CH$_3$—C$_6$H$_4$ |
| 1.1533 | CH(CH$_3$)$_2$ | CH(CH$_3$) | CH$_3$ | CH(CH$_3$)CH$_2$ | 4-CH$_3$O—C$_6$H$_4$ |
| 1.1534 | CH(CH$_3$)$_2$ | CH(CH$_3$) | CH$_3$ | CH(CH$_3$)CH$_2$ | 4-CN—C$_6$H$_4$ |
| 1.1535 | CH(CH$_3$)$_2$ | CH(CH$_3$) | CH$_3$ | CH(CH$_3$)CH$_2$ | 3-Cl—C$_6$H$_4$ |
| 1.1536 | CH(CH$_3$)$_2$ | CH(CH$_3$) | CH$_3$ | CH(CH$_3$)CH$_2$ | 3-CH$_3$—C$_6$H$_4$ |
| 1.1537 | CH(CH$_3$)$_2$ | CH(CH$_3$) | CH$_3$ | CH(CH$_3$)CH$_2$ | 3-CH$_3$O—C$_6$H$_4$ |
| 1.1538 | CH(CH$_3$)$_2$ | CH(CH$_3$) | CH$_3$ | CH(CH$_3$)CH$_2$ | 3-CN—C$_6$H$_4$ |
| 1.1539 | CH(CH$_3$)$_2$ | CH(CH$_3$) | CH$_3$ | CH(CH$_3$)CH$_2$ | 2-Cl—C$_6$H$_4$ |
| 1.1540 | CH(CH$_3$)$_2$ | CH(CH$_3$) | CH$_3$ | CH(CH$_3$)CH$_2$ | 2-CH$_3$—C$_6$H$_4$ |
| 1.1541 | CH(CH$_3$)$_2$ | CH(CH$_3$) | CH$_3$ | CH(CH$_3$)CH$_2$ | 2-CH$_3$O—C$_6$H$_4$ |
| 1.1542 | CH(CH$_3$)$_2$ | CH(CH$_3$) | CH$_3$ | CH(CH$_3$)CH$_2$ | 2-CN—C$_6$H$_4$ |
| 1.1543 | CH(CH$_3$)$_2$ | CH(CH$_3$) | CH$_3$ | CH(CH$_3$)CH$_2$ | 3,4-(CH$_3$O)$_2$C$_6$H$_3$ |
| 1.1544 | CH(CH$_3$)$_2$ | CH(CH$_3$) | CH$_3$ | CH(CH$_3$)CH$_2$ | 2,4-Cl$_2$—C$_6$H$_3$ |
| 1.1545 | CH(CH$_3$)$_2$ | CH(CH$_3$) | CH$_3$ | CH(CH$_3$)CH$_2$ | 2,4-(CH$_3$)$_2$—C$_6$H$_3$ |
| 1.1546 | CH(CH$_3$)$_2$ | CH(CH$_3$) | CH$_3$ | CH(CH$_3$)CH$_2$ | 3,4-(CH$_3$)$_2$C$_6$H$_3$ |
| 1.1547 | CH(CH$_3$)$_2$ | CH(CH$_3$) | CH$_3$ | CH(CH$_3$)CH$_2$ | 4-NO$_2$—C$_6$H$_4$ |
| 1.1548 | CH(CH$_3$)C$_2$H$_5$ | CH(CH$_3$) | CH$_3$ | CH(CH$_3$)CH$_2$ | 4-Cl—C$_6$H$_4$ |
| 1.1549 | CH(CH$_3$)C$_2$H$_5$ | CH(CH$_3$) | CH$_3$ | CH(CH$_3$)CH$_2$ | 4-CH$_3$—C$_6$H$_4$ |
| 1.1550 | CH(CH$_3$)C$_2$H$_5$ | CH(CH$_3$) | CH$_3$ | CH(CH$_3$)CH$_2$ | 4-CH$_3$O—C$_6$H$_4$ |
| 1.1551 | CH(CH$_3$)C$_2$H$_5$ | CH(CH$_3$) | CH$_3$ | CH(CH$_3$)CH$_2$ | 4-CN—C$_6$H$_4$ |
| 1.1552 | CH(CH$_3$)C$_2$H$_5$ | CH(CH$_3$) | CH$_3$ | CH(CH$_3$)CH$_2$ | 3-Cl—C$_6$H$_4$ |
| 1.1553 | CH(CH$_3$)C$_2$H$_5$ | CH(CH$_3$) | CH$_3$ | CH(CH$_3$)CH$_2$ | 3-CH$_3$—C$_6$H$_4$ |
| 1.1554 | CH(CH$_3$)C$_2$H$_5$ | CH(CH$_3$) | CH$_3$ | CH(CH$_3$)CH$_2$ | 3-CH$_3$O—C$_6$H$_4$ |
| 1.1555 | CH(CH$_3$)C$_2$H$_5$ | CH(CH$_3$) | CH$_3$ | CH(CH$_3$)CH$_2$ | 3-CN—C$_6$H$_4$ |
| 1.1556 | CH(CH$_3$)C$_2$H$_5$ | CH(CH$_3$) | CH$_3$ | CH(CH$_3$)CH$_2$ | 2-Cl—C$_6$H$_4$ |
| 1.1557 | CH(CH$_3$)C$_2$H$_5$ | CH(CH$_3$) | CH$_3$ | CH(CH$_3$)CH$_2$ | 2-CH$_3$—C$_6$H$_4$ |
| 1.1558 | CH(CH$_3$)C$_2$H$_5$ | CH(CH$_3$) | CH$_3$ | CH(CH$_3$)CH$_2$ | 2-CH$_3$O—C$_6$H$_4$ |
| 1.1559 | CH(CH$_3$)C$_2$H$_5$ | CH(CH$_3$) | CH$_3$ | CH(CH$_3$)CH$_2$ | 2-CN—C$_6$H$_4$ |
| 1.1560 | CH(CH$_3$)C$_2$H$_5$ | CH(CH$_3$) | CH$_3$ | CH(CH$_3$)CH$_2$ | 3,4-(CH$_3$)$_2$C$_6$H$_3$ |
| 1.1561 | CH(CH$_3$)C$_2$H$_5$ | CH(CH$_3$) | CH$_3$ | CH(CH$_3$)CH$_2$ | 2,4-Cl$_2$—C$_6$H$_3$ |
| 1.1562 | CH(CH$_3$)C$_2$H$_5$ | CH(CH$_3$) | CH$_3$ | CH(CH$_3$)CH$_2$ | 2,4-(CH$_3$)$_2$—C$_6$H$_3$ |
| 1.1563 | CH(CH$_3$)C$_2$H$_5$ | CH(CH$_3$) | CH$_3$ | CH(CH$_3$)CH$_2$ | 3,4-(CH$_3$)$_2$C$_6$H$_3$ |
| 1.1564 | CH(CH$_3$)C$_2$H$_5$ | CH(CH$_3$) | CH$_3$ | CH(CH$_3$)CH$_2$ | 3,4-NO$_2$—C$_6$H$_4$ |
| 1.1565 | C(CH$_3$)$_3$ | CH(CH$_3$) | CH$_3$ | CH(CH$_3$)CH$_2$ | 4-Cl—C$_6$H$_4$ |
| 1.1566 | C(CH$_3$)$_3$ | CH(CH$_3$) | CH$_3$ | CH(CH$_3$)CH$_2$ | 4-CH$_3$—C$_6$H$_4$ |
| 1.1567 | C(CH$_3$)$_3$ | CH(CH$_3$) | CH$_3$ | CH(CH$_3$)CH$_2$ | 4-CH$_3$O—C$_6$H$_4$ |
| 1.1568 | C(CH$_3$)$_3$ | CH(CH$_3$) | CH$_3$ | CH(CH$_3$)CH$_2$ | 4-CN—C$_6$H$_4$ |
| 1.1569 | C(CH$_3$)$_3$ | CH(CH$_3$) | CH$_3$ | CH(CH$_3$)CH$_2$ | 3-Cl—C$_6$H$_4$ |
| 1.1570 | C(CH$_3$)$_3$ | CH(CH$_3$) | CH$_3$ | CH(CH$_3$)CH$_2$ | 3-CH$_3$—C$_6$H$_4$ |
| 1.1571 | C(CH$_3$)$_3$ | CH(CH$_3$) | CH$_3$ | CH(CH$_3$)CH$_2$ | 3-CH$_3$O—C$_6$H$_4$ |
| 1.1572 | C(CH$_3$)$_3$ | CH(CH$_3$) | CH$_3$ | CH(CH$_3$)CH$_2$ | 3-CN—C$_6$H$_4$ |
| 1.1573 | C(CH$_3$)$_3$ | CH(CH$_3$) | CH$_3$ | CH(CH$_3$)CH$_2$ | 2-Cl—C$_6$H$_4$ |
| 1.1574 | C(CH$_3$)$_3$ | CH(CH$_3$) | CH$_3$ | CH(CH$_3$)CH$_2$ | 2-CH$_3$—C$_6$H$_4$ |
| 1.1575 | C(CH$_3$)$_3$ | CH(CH$_3$) | CH$_3$ | CH(CH$_3$)CH$_2$ | 2-CH$_3$O—C$_6$H$_4$ |
| 1.1576 | C(CH$_3$)$_3$ | CH(CH$_3$) | CH$_3$ | CH(CH$_3$)CH$_2$ | 2-CN—C$_6$H$_4$ |
| 1.1577 | C(CH$_3$)$_3$ | CH(CH$_3$) | CH$_3$ | CH(CH$_3$)CH$_2$ | 3,4-(CH$_3$O)$_2$C$_6$H$_3$ |
| 1.1578 | C(CH$_3$)$_3$ | CH(CH$_3$) | CH$_3$ | CH(CH$_3$)CH$_2$ | 2,4-Cl$_2$—C$_6$H$_3$ |
| 1.1579 | C(CH$_3$)$_3$ | CH(CH$_3$) | CH$_3$ | CH(CH$_3$)CH$_2$ | 2,4-(CH$_3$)$_2$—C$_6$H$_3$ |
| 1.1580 | C(CH$_3$)$_3$ | CH(CH$_3$) | CH$_3$ | CH(CH$_3$)CH$_2$ | 3,4-(CH$_3$)$_2$C$_6$H$_3$ |
| 1.1581 | C(CH$_3$)$_3$ | CH(CH$_3$) | CH$_3$ | CH(CH$_3$)CH$_2$ | 4-NO$_2$—C$_6$H$_4$ |
| 1.1582 | CH(CH$_3$)$_2$ | C(CH$_3$)$_2$—CH$_2$ | CH$_3$ | CH(CH$_3$)CH$_2$ | 2,4-Cl—C$_6$H$_4$ |
| 1.1583 | CH(CH$_3$)$_2$ | C(CH$_3$)$_2$—CH$_2$ | CH$_3$ | CH(CH$_3$)CH$_2$ | 4-CH$_3$—C$_6$H$_4$ |
| 1.1584 | CH(CH$_3$)$_2$ | C(CH$_3$)$_2$—CH$_2$ | CH$_3$ | CH(CH$_3$)CH$_2$ | 4-CH$_3$O—C$_6$H$_4$ |
| 1.1585 | CH(CH$_3$)$_2$ | C(CH$_3$)$_2$—CH$_2$ | CH$_3$ | CH(CH$_3$)CH$_2$ | 4-CN—C$_6$H$_4$ |
| 1.1586 | CH(CH$_3$)$_2$ | C(CH$_3$)$_2$—CH$_2$ | CH$_3$ | CH(CH$_3$)CH$_2$ | 3-Cl—C$_6$H$_4$ |
| 1.1587 | CH(CH$_3$)$_2$ | C(CH$_3$)$_2$—CH$_2$ | CH$_3$ | CH(CH$_3$)CH$_2$ | 3-CH$_3$—C$_6$H$_4$ |
| 1.1588 | CH(CH$_3$)$_2$ | C(CH$_3$)$_2$—CH$_2$ | CH$_3$ | CH(CH$_3$)CH$_2$ | 3-CH$_3$O—C$_6$H$_4$ |
| 1.1589 | CH(CH$_3$)$_2$ | C(CH$_3$)$_2$—CH$_2$ | CH$_3$ | CH(CH$_3$)CH$_2$ | 3-CN—C$_6$H$_4$ |
| 1.1590 | CH(CH$_3$)$_2$ | C(CH$_3$)$_2$—CH$_2$ | CH$_3$ | CH(CH$_3$)CH$_2$ | 2-Cl—C$_6$H$_4$ |

TABLE A-continued $$R^1-O-\overset{O}{\underset{}{C}}-NH-\underset{\underset{S}{\|}}{CH}-\overset{O}{\underset{}{C}}-NH-A-\overset{Y}{\underset{}{C}}=N-O-Z-Ar$$

with CH(CH₃)₂ on the CH carbon (I')

| No. | R¹ | A | Y | Z | Ar |
|---|---|---|---|---|---|
| 1.1591 | CH(CH₃)₂ | C(CH₃)₂—CH₂ | CH₃ | CH(CH₃)CH₂ | 2-CH₃—C₆H₄ |
| 1.1592 | CH(CH₃)₂ | C(CH₃)₂—CH₂ | CH₃ | CH(CH₃)CH₂ | 2-CH₃O—C₆H₄ |
| 1.1593 | CH(CH₃)₂ | C(CH₃)₂—CH₂ | CH₃ | CH(CH₃)CH₂ | 2-CN—C₆H₄ |
| 1.1594 | CH(CH₃)₂ | C(CH₃)₂—CH₂ | CH₃ | CH(CH₃)CH₂ | 3,4-(CH₃O)₂C₆H₃ |
| 1.1595 | CH(CH₃)₂ | C(CH₃)₂—CH₂ | CH₃ | CH(CH₃)CH₂ | 2,4-Cl₂—C₆H₃ |
| 1.1596 | CH(CH₃)₂ | C(CH₃)₂—CH₂ | CH₃ | CH(CH₃)CH₂ | 2,4-(CH₃)₂—C₆H₃ |
| 1.1597 | CH(CH₃)₂ | C(CH₃)₂—CH₂ | CH₃ | CH(CH₃)CH₂ | 3,4-(CH₃)₂C₆H₃ |
| 1.1598 | CH(CH₃)₂ | C(CH₃)₂—CH₂ | CH₃ | CH(CH₃)CH₂ | 4-NO₂—C₆H₄ |
| 1.1599 | CH(CH₃)C₂H₅ | C(CH₃)₂—CH₂ | CH₃ | CH(CH₃)CH₂ | 4-Cl—C₆H₄ |
| 1.1600 | CH(CH₃)C₂H₅ | C(CH₃)₂—CH₂ | CH₃ | CH(CH₃)CH₂ | 4-CH₃—C₆H₄ |
| 1.1601 | CH(CH₃)C₂H₅ | C(CH₃)₂—CH₂ | CH₃ | CH(CH₃)CH₂ | 4-CH₃O—C₆H₄ |
| 1.1602 | CH(CH₃)C₂H₅ | C(CH₃)₂—CH₂ | CH₃ | CH(CH₃)CH₂ | ,4-CN—C₆H₄ |
| 1.1603 | CH(CH₃)C₂H₅ | C(CH₃)₂—CH₂ | CH₃ | CH(CH₃)CH₂ | 3-Cl—C₆H₄ |
| 1.1604 | CH(CH₃)C₂H₅ | C(CH₃)₂—CH₂ | CH₃ | CH(CH₃)CH₂ | 3-CH₃—C₆H₄ |
| 1.1605 | CH(CH₃)C₂H₅ | C(CH₃)₂—CH₂ | CH₃ | CH(CH₃)CH₂ | 3-CH₃O—C₆H₄ |
| 1.1606 | CH(CH₃)C₂H₅ | C(CH₃)₂—CH₂ | CH₃ | CH(CH₃)CH₂ | 3-CN—C₆H₄ |
| 1.1607 | CH(CH₃)C₂H₅ | C(CH₃)₂—CH₂ | CH₃ | CH(CH₃)CH₂ | 2-Cl—C₆H₄ |
| 1.1608 | CH(CH₃)C₂H₅ | C(CH₃)₂—CH₂ | CH₃ | CH(CH₃)CH₂ | 2-CH₃—C₆H₄ |
| 1.1609 | CH(CH₃)C₂H₅ | C(CH₃)₂—CH₂ | CH₃ | CH(CH₃)CH₂ | 2-CH₃O—C₆H₄ |
| 1.1610 | CH(CH₃)C₂H₅ | C(CH₃)₂—CH₂ | CH₃ | CH(CH₃)CH₂ | 2-CN—C₆H₄ |
| 1.1611 | CH(CH₃)C₂H₅ | C(CH₃)₂—CH₂ | CH₃ | CH(CH₃)CH₂ | 3,4-(CH₃O)₂C₆H₃ |
| 1.1612 | CH(CH₃)C₂H₅ | C(CH₃)₂—CH₂ | CH₃ | CH(CH₃)CH₂ | 2,4-Cl₂—C₆H₃ |
| 1.1613 | CH(CH₃)C₂H₅ | C(CH₃)₂—CH₂ | CH₃ | CH(CH₃)CH₂ | 2,4-(CH₃)₂—C₆H₃ |
| 1.1614 | CH(CH₃)C₂H₅ | C(CH₃)₂—CH₂ | CH₃ | CH(CH₃)CH₂ | 3,4-(CH₃)₂C₆H₃ |
| 1.1615 | CH(CH₃)C₂H₅ | C(CH₃)₂—CH₂ | CH₃ | CH(CH₃)CH₂ | 4-NO₂—C₆H₄ |
| 1.1616 | C(CH₃)₃ | C(CH₃)₂—CH₂ | CH₃ | CH(CH₃)CH₂ | 4-Cl—C₆H₄ |
| 1.1617 | C(CH₃)₃ | C(CH₃)₂—CH₂ | CH₃ | CH(CH₃)CH₂ | ,4-CH₃—C₆H₄ |
| 1.1618 | C(CH₃)₃ | C(CH₃)₂—CH₂ | CH₃ | CH(CH₃)CH₂ | 4-CH₃O—C₆H₄ |
| 1.1619 | C(CH₃)₃ | C(CH₃)₂—CH₂ | CH₃ | CH(CH₃)CH₂ | 4-CN—C₆H₄ |
| 1.1620 | C(CH₃)₃ | C(CH₃)₂—CH₂ | CH₃ | CH(CH₃)CH₂ | 3-Cl—C₆H₄ |
| 1.1621 | C(CH₃)₃ | C(CH₃)₂—CH₂ | CH₃ | CH(CH₃)CH₂ | 3-CH₃—C₆H₄ |
| 1.1622 | C(CH₃)₃ | C(CH₃)₂—CH₂ | CH₃ | CH(CH₃)CH₂ | 3-CH₃O—C₆H₄ |
| 1.1623 | C(CH₃)₃ | C(CH₃)₂—CH₂ | CH₃ | CH(CH₃)CH₂ | 3-CN—C₆H₄ |
| 1.1624 | C(CH₃)₃ | C(CH₃)₂—CH₂ | CH₃ | CH(CH₃)CH₂ | 2-Cl—C₆H₄ |
| 1.1625 | C(CH₃)₃ | C(CH₃)₂—CH₂ | CH₃ | CH(CH₃)CH₂ | 2-CH₃—C₆H₄ |
| 1.1626 | C(CH₃)₃ | C(CH₃)₂—CH₂ | CH₃ | CH(CH₃)CH₂ | 2-CH₃O—C₆H₄ |
| 1.1627 | C(CH₃)₃ | C(CH₃)₂—CH₂ | CH₃ | CH(CH₃)CH₂ | 2-CN—C₆H₄ |
| 1.1628 | C(CH₃)₃ | C(CH₃)₂—CH₂ | CH₃ | CH(CH₃)CH₂ | 3,4-(CH₃O)₂C₆H₃ |
| 1.1629 | C(CH₃)₃ | C(CH₃)₂—CH₂ | CH₃ | CH(CH₃)CH₂ | 2,4-Cl₂—C₆H₃ |
| 1.1630 | C(CH₃)₃ | C(CH₃)₂—CH₂ | CH₃ | CH(CH₃)CH₂ | 2,4-(CH₃)₂—C₆H₃ |
| 1.1631 | C(CH₃)₃ | C(CH₃)₂—CH₂ | CH₃ | CH(CH₃)CH₂ | 3,4-(CH₃)₂C₆H₃ |
| 1.1632 | C(CH₃)₃ | C(CH₃)₂—CH₂ | CH₃ | CH(CH₃)CH₂ | 4-NO₂—C₆H₄ |
| 1.1633 | CH(CH₃)₂ | CH(CH₃) | H | CH(CH₃)CH₂ | 4-Cl—C₆H₄ |
| 1.1634 | CH(CH₃)₂ | CH(CH₃) | H | CH(CH₃)CH₂ | 4-CH₃—C₆H₄ |
| 1.1635 | CH(CH₃)₂ | CH(CH₃) | H | CH(CH₃)CH₂ | 4-CH₃O—C₆H₄ |
| 1.1636 | CH(CH₃)₂ | CH(CH₃) | H | CH(CH₃)CH₂ | 4-CN—C₆H₄ |
| 1.1637 | CH(CH₃)₂ | CH(CH₃) | H | CH(CH₃)CH₂ | 3-Cl—C₆H₄ |
| 1.1638 | CH(CH₃)₂ | CH(CH₃) | H | CH(CH₃)CH₂ | 3-CH₃—C₆H₄ |
| 1.1639 | CH(CH₃)₂ | CH(CH₃) | H | CH(CH₃)CH₂ | 3-CH₃O—C₆H₄ |
| 1.1640 | CH(CH₃)₂ | CH(CH₃) | H | CH(CH₃)CH₂ | 3-CN—C₆H₄ |
| 1.1641 | CH(CH₃)₂ | CH(CH₃) | H | CH(CH₃)CH₂ | 2-Cl—C₆H₄ |
| 1.1642 | CH(CH₃)₂ | CH(CH₃) | H | CH(CH₃)CH₂ | 2-CH₃—C₆H₄ |
| 1.1643 | CH(CH₃)₂ | CH(CH₃) | H | CH(CH₃)CH₂ | 2-CH₃O—C₆H₄ |
| 1.1644 | CH(CH₃)₂ | CH(CH₃) | H | CH(CH₃)CH₂ | 2-CN—C₆H₄ |
| 1.1645 | CH(CH₃)₂ | CH(CH₃) | H | CH(CH₃)CH₂ | 3,4-(CH₃O)₂C₆H₃ |
| 1.1646 | CH(CH₃)₂ | CH(CH₃) | H | CH(CH₃)CH₂ | 2,4-Cl₂—C₆H₃ |
| 1.1647 | CH(CH₃)₂ | CH(CH₃) | H | CH(CH₃)CH₂ | 2,4-(CH₃)₂—C₆H₃ |
| 1.1648 | CH(CH₃)₂ | CH(CH₃) | H | CH(CH₃)CH₂ | 3,4-(CH₃)₂C₆H₃ |
| 1.1649 | CH(CH₃)₂ | CH(CH₃) | H | CH(CH₃)CH₂ | 4-NO₂—C₆H₄ |
| 1.1650 | CH(CH₃)C₂H₅ | CH(CH₃) | H | CH(CH₃)CH₂ | 4-Cl—C₆H₄ |
| 1.1651 | CH(CH₃)C₂H₅ | CH(CH₃) | H | CH(CH₃)CH₂ | 4-CH₃—C₆H₄ |
| 1.1652 | CH(CH₃)C₂H₅ | CH(CH₃) | H | CH(CH₃)CH₂ | 4-CH₃O—C₆H₄ |
| 1.1653 | CH(CH₃)C₂H₅ | CH(CH₃) | H | CH(CH₃)CH₂ | 4-CN—C₆H₄ |
| 1.1654 | CH(CH₃)C₂H₅ | CH(CH₃) | H | CH(CH₃)CH₂ | 3-Cl—C₆H₄ |
| 1.1655 | CH(CH₃)C₂H₅ | CH(CH₃) | H | CH(CH₃)CH₂ | 3-CH₃—C₆H₄ |
| 1.1656 | CH(CH₃)C₂H₅ | CH(CH₃) | H | CH(CH₃)CH₂ | 3-CH₃O—C₆H₄ |
| 1.1657 | CH(CH₃)C₂H₅ | CH(CH₃) | H | CH(CH₃)CH₂ | 3-CN—C₆H₄ |
| 1.1658 | CH(CH₃)C₂H₅ | CH(CH₃) | H | CH(CH₃)CH₂ | 2-Cl—C₆H₄ |
| 1.1659 | CH(CH₃)C₂H₅ | CH(CH₃) | H | CH(CH₃)CH₂ | 2-CH₃—C₆H₄ |
| 1.1660 | CH(CH₃)C₂H₅ | CH(CH₃) | H | CH(CH₃)CH₂ | 2-CH₃O—C₆H₄ |

TABLE A-continued $$R^1-O-\overset{O}{\underset{}{C}}-NH-\overset{CH(CH_3)_2}{\underset{S}{CH}}-\overset{O}{\underset{}{C}}-NH-A-\overset{Y}{\underset{}{C}}=N-O-Z-Ar \quad (I')$$

| No. | R¹ | A | Y | Z | Ar |
|---|---|---|---|---|---|
| 1.1661 | CH(CH₃)C₂H₅ | CH(CH₃) | H | CH(CH₃)CH₂ | 2-CN—C₆H₄ |
| 1.1662 | CH(CH₃)C₂H₅ | CH(CH₃) | H | CH(CH₃)CH₂ | 3,4-(CH₃O)₂C₆H₃ |
| 1.1663 | CH(CH₃)C₂H₅ | CH(CH₃) | H | CH(CH₃)CH₂ | 2,4-Cl₂—C₆H₃ |
| 1.1664 | CH(CH₃)C₂H₅ | CH(CH₃) | H | CH(CH₃)CH₂ | 2,4-(CH₃)₂—C₆H₃ |
| 1.1665 | CH(CH₃)C₂H₅ | CH(CH₃) | H | CH(CH₃)CH₂ | 3,4-(CH₃)₂C₆H₃ |
| 1.1666 | CH(CH₃)C₂H₅ | CH(CH₃) | H | CH(CH₃)CH₂ | 4-NO₂—C₆H₄ |
| 1.1667 | C(CH₃)₃ | CH(CH₃) | H | CH(CH₃)CH₂ | 4-Cl—C₆H₄ |
| 1.1668 | C(CH₃)₃ | CH(CH₃) | H | CH(CH₃)CH₂ | 4-CH₃—C₆H₄ |
| 1.1669 | C(CH₃)₃ | CH(CH₃) | H | CH(CH₃)CH₂ | 4-CH₃O—C₆H₄ |
| 1.1670 | C(CH₃)₃ | CH(CH₃) | H | CH(CH₃)CH₂ | 4-CN—C₆H₄ |
| 1.1671 | C(CH₃)₃ | CH(CH₃) | H | CH(CH₃)CH₂ | 3-Cl—C₆H₄ |
| 1.1672 | C(CH₃)₃ | CH(CH₃) | H | CH(CH₃)CH₂ | 3-CH₃—C₆H₄ |
| 1.1673 | C(CH₃)₃ | CH(CH₃) | H | CH(CH₃)CH₂ | 3-CH₃O—C₆H₄ |
| 1.1674 | C(CH₃)₃ | CH(CH₃) | H | CH(CH₃)CH₂ | 3-CN—C₆H₄ |
| 1.1675 | C(CH₃)₃ | CH(CH₃) | H | CH(CH₃)CH₂ | 2-Cl—C₆H₄ |
| 1.1676 | C(CH₃)₃ | CH(CH₃) | H | CH(CH₃)CH₂ | 2-CH₃—C₆H₄ |
| 1.1677 | C(CH₃)₃ | CH(CH₃) | H | CH(CH₃)CH₂ | 2-CH₃O—C₆H₄ |
| 1.1678 | C(CH₃)₃ | CH(CH₃) | H | CH(CH₃)CH₂ | 2-CN—C₆H₄ |
| 1.1679 | C(CH₃)₃ | CH(CH₃) | H | CH(CH₃)CH₂ | 3,4-(CH₃O)₂C₆H₃ |
| 1.1680 | C(CH₃)₃ | CH(CH₃) | H | CH(CH₃)CH₂ | 2,4-Cl₂—C₆H₃ |
| 1.1681 | C(CH₃)₃ | CH(CH₃) | H | CH(CH₃)CH₂ | 2,4-(CH₃)₂—C₆H₃ |
| 1.1682 | C(CH₃)₃ | CH(CH₃) | H | CH(CH₃)CH₂ | 3,4-(CH₃)₂C₆H₃ |
| 1.1683 | C(CH₃)₃ | CH(CH₃) | H | CH(CH₃)CH₂ | 4-NO₂—C₆H₄ |
| 1.1684 | CH(CH₃)₂ | C(CH₃)₂—CH₂ | H | CH(CH₃)CH₂ | 4-Cl—C₆H₄ |
| 1.1685 | CH(CH₃)₂ | C(CH₃)₂—CH₂ | H | CH(CH₃)CH₂ | 4-CH₃—C₆H₄ |
| 1.1686 | CH(CH₃)₂ | C(CH₃)₂—CH₂ | H | CH(CH₃)CH₂ | 4-CH₃O—C₆H₄ |
| 1.1687 | CH(CH₃)₂ | C(CH₃)₂—CH₂ | H | CH(CH₃)CH₂ | 4-CN—C₆H₄ |
| 1.1688 | CH(CH₃)₂ | C(CH₃)₂—CH₂ | H | CH(CH₃)CH₂ | 3-Cl—C₆H₄ |
| 1.1689 | CH(CH₃)₂ | C(CH₃)₂—CH₂ | H | CH(CH₃)CH₂ | 3-CH₃—C₆H₄ |
| 1.1690 | CH(CH₃)₂ | C(CH₃)₂—CH₂ | H | CH(CH₃)CH₂ | 3-CH₃O—C₆H₄ |
| 1.1691 | CH(CH₃)₂ | C(CH₃)₂—CH₂ | H | CH(CH₃)CH₂ | 3-CN—C₆H₄ |
| 1.1692 | CH(CH₃)₂ | C(CH₃)₂—CH₂ | H | CH(CH₃)CH₂ | 2-Cl—C₆H₄ |
| 1.1693 | CH(CH₃)₂ | C(CH₃)₂—CH₂ | H | CH(CH₃)CH₂ | 2-CH₃—C₆H₄ |
| 1.1694 | CH(CH₃)₂ | C(CH₃)₂—CH₂ | H | CH(CH₃)CH₂ | 2-CH₃O—C₆H₄ |
| 1.1695 | CH(CH₃)₂ | C(CH₃)₂—CH₂ | H | CH(CH₃)CH₂ | 2-CN—C₆H₄ |
| 1.1696 | CH(CH₃)₂ | C(CH₃)₂—CH₂ | H | CH(CH₃)CH₂ | 3,4-(CH₃O)₂C₆H₃ |
| 1.1697 | CH(CH₃)₂ | C(CH₃)₂—CH₂ | H | CH(CH₃)CH₂ | 2,4-Cl₂—C₆H₃ |
| 1.1698 | CH(CH₃)₂ | C(CH₃)₂—CH₂ | H | CH(CH₃)CH₂ | 2,4-(CH₃)₂—C₆H₃ |
| 1.1699 | CH(CH₃)₂ | C(CH₃)₂—CH₂ | H | CH(CH₃)CH₂ | 3,4-(CH₃)₂C₆H₃ |
| 1.1700 | CH(CH₃)₂ | C(CH₃)₂—CH₂ | H | CH(CH₃)CH₂ | 4-NO₂—C₆H₄ |
| 1.1701 | CH(CH₃)C₂H₅ | C(CH₃)₂—CH₂ | H | CH(CH₃)CH₂ | 4-Cl—C₆H₄ |
| 1.1702 | CH(CH₃)C₂H₅ | C(CH₃)₂—CH₂ | H | CH(CH₃)CH₂ | 4-CH₃—C₆H₄ |
| 1.1703 | CH(CH₃)C₂H₅ | C(CH₃)₂—CH₂ | H | CH(CH₃)CH₂ | 4-CH₃O—C₆H₄ |
| 1.1704 | CH(CH₃)C₂H₅ | C(CH₃)₂—CH₂ | H | CH(CH₃)CH₂ | 4-CN—C₆H₄ |
| 1.1705 | CH(CH₃)C₂H₅ | C(CH₃)₂—CH₂ | H | CH(CH₃)CH₂ | 3-Cl—C₆H₄ |
| 1.1706 | CH(CH₃)C₂H₅ | C(CH₃)₂—CH₂ | H | CH(CH₃)CH₂ | 3-CH₃—C₆H₄ |
| 1.1707 | CH(CH₃)C₂H₅ | C(CH₃)₂—CH₂ | H | CH(CH₃)CH₂ | 3-CH₃O—C₆H₄ |
| 1.1708 | CH(CH₃)C₂H₅ | C(CH₃)₂—CH₂ | H | CH(CH₃)CH₂ | 3-CN—C₆H₄ |
| 1.1709 | CH(CH₃)C₂H₅ | C(CH₃)₂—CH₂ | H | CH(CH₃)CH₂ | 2-Cl—C₆H₄ |
| 1.1710 | CH(CH₃)C₂H₅ | C(CH₃)₂—CH₂ | H | CH(CH₃)CH₂ | 2-CH₃—C₆H₄ |
| 1.1711 | CH(CH₃)C₂H₅ | C(CH₃)₂—CH₂ | H | CH(CH₃)CH₂ | 2-CH₃O—C₆H₄ |
| 1.1712 | CH(CH₃)C₂H₅ | C(CH₃)₂—CH₂ | H | CH(CH₃)CH₂ | 2-CN—C₆H₄ |
| 1.1713 | CH(CH₃)C₂H₅ | C(CH₃)₂—CH₂ | H | CH(CH₃)CH₂ | 3,4-(CH₃O)₂C₆H₃ |
| 1.1714 | CH(CH₃)C₂H₅ | C(CH₃)₂—CH₂ | H | CH(CH₃)CH₂ | 2,4-Cl₂—C₆H₃ |
| 1.1715 | CH(CH₃)C₂H₅ | C(CH₃)₂—CH₂ | H | CH(CH₃)CH₂ | 2,4-(CH₃)₂—CH₃ |
| 1.1716 | CH(CH₃)C₂H₅ | C(CH₃)₂—CH₂ | H | CH(CH₃)CH₂ | 3,4-(CH₃)₂C₆H₃ |
| 1.1717 | CH(CH₃)C₂H₅ | C(CH₃)₂—CH₂ | H | CH(CH₃)CH₂ | 4-NO₂—C₆H₄ |
| 1.1718 | C(CH₃)₃ | C(CH₃)₂—CH₂ | H | CH(CH₃)CH₂ | 4-Cl—C₆H₄ |
| 1.1719 | C(CH₃)₃ | C(CH₃)₂—CH₂ | H | CH(CH₃)CH₂ | 4-CH₃—C₆H₄ |
| 1.1720 | C(CH₃)₃ | C(CH₃)₂—CH₂ | H | CH(CH₃)CH₂ | 4-CH₃O—C₆H₄ |
| 1.1721 | C(CH₃)₃ | C(CH₃)₂—CH₂ | H | CH(CH₃)CH₂ | 4-CN—C₆H₄ |
| 1.1722 | C(CH₃)₃ | C(CH₃)₂—CH₂ | H | CH(CH₃)CH₂ | 3-Cl—C₆H₄ |
| 1.1723 | C(CH₃)₃ | C(CH₃)₂—CH₂ | H | CH(CH₃)CH₂ | 3-CH₃—C₆H₄ |
| 1.1724 | C(CH₃)₃ | C(CH₃)₂—CH₂ | H | CH(CH₃)CH₂ | 3-CH₃O—C₆H₄ |
| 1.1725 | C(CH₃)₃ | C(CH₃)₂—CH₂ | H | CH(CH₃)CH₂ | 3-CN—C₆H₄ |
| 1.1726 | C(CH₃)₃ | C(CH₃)₂—CH₂ | H | CH(CH₃)CH₂ | 2-Cl—C₆H₄ |
| 1.1727 | C(CH₃)₃ | C(CH₃)₂—CH₂ | H | CH(CH₃)CH₂ | 2-CH₃—C₆H₄ |
| 1.1728 | C(CH₃)₃ | C(CH₃)₂—CH₂ | H | CH(CH₃)CH₂ | 2-CH₃O—C₆H₄ |
| 1.1729 | C(CH₃)₃ | C(CH₃)₂—CH₂ | H | CH(CH₃)CH₂ | 2-CN—C₆H₄ |
| 1.1730 | C(CH₃)₃ | C(CH₃)₂—CH₂ | H | CH(CH₃)CH₂ | 3,4-(CH₃O)₂C₆H₃ |

TABLE A-continued $$R^1-O-\underset{O}{\overset{O}{C}}-NH-\underset{\underline{S}}{\overset{CH(CH_3)_2}{CH}}-\underset{O}{\overset{O}{C}}-NH-A-\overset{Y}{\underset{}{C}}=N-O-Z-Ar \quad (I')$$

| No. | R¹ | A | Y | Z | Ar |
|---|---|---|---|---|---|
| 1.1731 | C(CH₃)₃ | C(CH₃)₂—CH₂ | H | CH(CH₃)CH₂ | 2,4-Cl₂—C₆H₃ |
| 1.1732 | C(CH₃)₃ | C(CH₃)₂—CH₂ | H | CH(CH₃)CH₂ | 2,4-(CH₃)₂—C₆H₃ |
| 1.1733 | C(CH₃)₃ | C(CH₃)₂—CH₂ | H | CH(CH₃)CH₂ | 3 4-(CH₃)₂C₆H₃ |
| 1.1734 | C(CH₃)₃ | C(CH₃)₂—CH₂ | H | CH(CH₃)CH₂ | 4-NO₂—C₆H₄ |
| 1.1735 | CH(CH₃)₂ | CH₂ | CH₃ | CH(CH₃)CH₂ | 4-Cl—C₆H₄ |
| 1.1736 | CH(CH₃)₂ | CH₂ | CH₃ | CH(CH₃)CH₂ | 4-CH₃—C₆H₄ |
| 1.1737 | CH(CH₃)₂ | CH₂ | CH₃ | CH(CH₃)CH₂ | 4-CH₃O—C₆H₄ |
| 1.1738 | CH(CH₃)₂ | CH₂ | CH₃ | CH(CH₃)CH₂ | 4-CN—C₆H₄ |
| 1.1739 | CH(CH₃)₂ | CH₂ | CH₃ | CH(CH₃)CH₂ | 3-Cl—C₆H₄ |
| 1.1740 | CH(CH₃)₂ | CH₂ | CH₃ | CH(CH₃)CH₂ | 3-CH₃—C₆H₄ |
| 1.1741 | CH(CH₃)₂ | CH₂ | CH₃ | CH(CH₃)CH₂ | 3-CH₃O—C₆H₄ |
| 1.1742 | CH(CH₃)₂ | CH₂ | CH₃ | CH(CH₃)CH₂ | 3-CN—C₆H₄ |
| 1.1743 | CH(CH₃)₂ | CH₂ | CH₃ | CH(CH₃)CH₂ | 2-Cl—C₆H₄ |
| 1.1744 | CH(CH₃)₂ | CH₂ | CH₃ | CH(CH₃)CH₂ | 2-CH₃—C₆H₄ |
| 1.1745 | CH(CH₃)₂ | CH₂ | CH₃ | CH(CH₃)CH₂ | 2-CH₃O—C₆H₄ |
| 1.1746 | CH(CH₃)₂ | CH₂ | CH₃ | CH(CH₃)CH₂ | 2-CN—C₆H₄ |
| 1.1747 | CH(CH₃)₂ | CH₂ | CH₃ | CH(CH₃)CH₂ | 3,4-(CH₃O)₂C₆H₃ |
| 1.1748 | CH(CH₃)₂ | CH₂ | CH₃ | CH(CH₃)CH₂ | 2,4-Cl₂—C₆H₃ |
| 1.1749 | CH(CH₃)₂ | CH₂ | CH₃ | CH(CH₃)CH₂ | 2,4-(CH₃)₂—C₆H₃ |
| 1.1750 | CH(CH₃)₂ | CH₂ | CH₃ | CH(CH₃)CH₂ | 3,4-(CH₃)₂C₆H₃ |
| 1.1751 | CH(CH₃)₂ | CH₂ | CH₃ | CH(CH₃)CH₂ | 4-NO₂—C₆H₄ |
| 1.1752 | CH(CH₃)C₂H₅ | CH₂ | CH₃ | CH(CH₃)CH₂ | 4-Cl—C₆H₄ |
| 1.1753 | CH(CH₃)C₂H₅ | CH₂ | CH₃ | CH(CH₃)CH₂ | 4-CH₃—C₆H₄ |
| 1.1754 | CH(CH₃)C₂H₅ | CH₂ | CH₃ | CH(CH₃)CH₂ | 4-CH₃O—C₆H₄ |
| 1.1755 | CH(CH₃)C₂H₅ | CH₂ | CH₃ | CH(CH₃)CH₂ | 4-CN—C₆H₄ |
| 1.1756 | CH(CH₃)C₂H₅ | CH₂ | CH₃ | CH(CH₃)CH₂ | 3-Cl—C₆H₄ |
| 1.1757 | CH(CH₃)C₂H₅ | CH₂ | CH₃ | CH(CH₃)CH₂ | 3-CH₃—C₆H₄ |
| 1.1758 | CH(CH₃)C₂H₅ | CH₂ | CH₃ | CH(CH₃)CH₂ | 3-CH₃O—C₆H₄ |
| 1.1759 | CH(CH₃)C₂H₅ | CH₂ | CH₃ | CH(CH₃)CH₂ | 3-CN—C₆H₄ |
| 1.1760 | CH(CH₃)C₂H₅ | CH₂ | CH₃ | CH(CH₃)CH₂ | 2-Cl—C₆H₄ |
| 1.1761 | CH(CH₃)C₂H₅ | CH₂ | CH₃ | CH(CH₃)CH₂ | 2-CH₃—C₆H₄ |
| 1.1762 | CH(CH₃)C₂H₅ | CH₂ | CH₃ | CH(CH₃)CH₂ | 2-CH₃C—C₆H₄ |
| 1.1763 | CH(CH₃)C₂H₅ | CH₂ | CH₃ | CH(CH₃)CH₂ | 2-CN—C₆H₄ |
| 1.1764 | CH(CH₃)C₂H₅ | CH₂ | CH₃ | CH(CH₃)CH₂ | 3,4-(CH₃O)₂C₆H₃ |
| 1.1765 | CH(CH₃)C₂H₅ | CH₂ | CH₃ | CH(CH₃)CH₂ | 2,4-Cl₂—C₆H₃ |
| 1.1766 | CH(CH₃)C₂H₅ | CH₂ | CH₃ | CH(CH₃)CH₂ | 2,4-(CH₃)₂—C₆H₃ |
| 1.1767 | CH(CH₃)C₂H₅ | CH₂ | CH₃ | CH(CH₃)CH₂ | 3,4-(CH₃)₂C₆H₃ |
| 1.1768 | CH(CH₃)C₂H₅ | CH₂ | CH₃ | CH(CH₃)CH₂ | 4-NO₂—C₆H₄ |
| 1.1769 | C(CH₃)₃ | CH₂ | CH₃ | CH(CH₃)CH₂ | 4-Cl—C₆H₄ |
| 1.1770 | C(CH₃)₃ | CH₂ | CH₃ | CH(CH₃)CH₂ | 4-CH₃—C₆H₄ |
| 1.1771 | C(CH₃)₃ | CH₂ | CH₃ | CH(CH₃)CH₂ | 4-CH₃O—C₆H₄ |
| 1.1772 | C(CH₃)₃ | CH₂ | CH₃ | CH(CH₃)CH₂ | 4-CN—C₆H₄ |
| 1.1773 | C(CH₃)₃ | CH₂ | CH₃ | CH(CH₃)CH₂ | 3-Cl—C₆H₄ |
| 1.1774 | C(CH₃)₃ | CH₂ | CH₃ | CH(CH₃)CH₂ | 3-CH₃—C₆H₄ |
| 1.1775 | C(CH₃)₃ | CH₂ | CH₃ | CH(CH₃)CH₂ | 3-CH₃O—C₆H₄ |
| 1.1776 | C(CH₃)₃ | CH₂ | CH₃ | CH(CH₃)CH₂ | 3-CN—C₆H₄ |
| 1.1777 | C(CH₃)₃ | CH₂ | CH₃ | CH(CH₃)CH₂ | 2-Cl—C₆H₄ |
| 1.1778 | C(CH₃)₃ | CH₂ | CH₃ | CH(CH₃)CH₂ | 2-CH₃—C₆H₄ |
| 1.1779 | C(CH₃)₃ | CH₂ | CH₃ | CH(CH₃)CH₂ | 2-CH₃O—C₆H₄ |
| 1.1780 | C(CH₃)₃ | CH₂ | CH₃ | CH(CH₃)CH₂ | 2-CN—C₆H₄ |
| 1.1781 | C(CH₃)₃ | CH₂ | CH₃ | CH(CH₃)CH₂ | 3,4-(CH₃O)₂C₆H₃ |
| 1.1782 | C(CH₃)₃ | CH₂ | CH₃ | CH(CH₃)CH₂ | 2,4-Cl₂—C₆H₃ |
| 1.1783 | C(CH₃)₃ | CH₂ | CH₃ | CH(CH₃)CH₂ | 2,4-(CH₃)₂—C₆H₃ |
| 1.1784 | C(CH₃)₃ | CH₂ | CH₃ | CH(CH₃)CH₂ | 3,4-(CH₃)₂C₆H₃ |
| 1.1785 | C(CH₃)₃ | CH₂ | CH₃ | CH(CH₃)CH₂ | 4-NO₂C₆H₄ |
| 1.1786 | CH(CH₃)₂ | CH₂ | H | CH(CH₃)CH₂ | 4-Cl—C₆H₄ |
| 1.1787 | CH(CH₃)₂ | CH₂ | H | CH(CH₃)CH₂ | 4-CH₃—C₆H₄ |
| 1.1788 | CH(CH₃)₂ | CH₂ | H | CH(CH₃)CH₂ | 4-CH₃O—C₆H₄ |
| 1.1789 | CH(CH₃)₂ | CH₂ | H | CH(CH₃)CH₂ | 4-CN—C₆H₄ |
| 1.1790 | CH(CH₃)₂ | CH₂ | H | CH(CH₃)CH₂ | 3-Cl—C₆H₄ |
| 1.1791 | CH(CH₃)₂ | CH₂ | H | CH(CH₃)CH₂ | 3-CH₃—C₆H₄ |
| 1.1792 | CH(CH₃)₂ | CH₂ | H | CH(CH₃)CH₂ | 3-CH₃O—C₆H₄ |
| 1.1793 | CH(CH₃)₂ | CH₂ | H | CH(CH₃)CH₂ | 3-CN—C₆H₄ |
| 1.1794 | CH(CH₃)₂ | CH₂ | H | CH(CH₃)CH₂ | 2-Cl—C₆H₄ |
| 1.1795 | CH(CH₃)₂ | CH₂ | H | CH(CH₃)CH₂ | 2-CH₃—C₆H₄ |
| 1.1796 | CH(CH₃)₂ | CH₂ | H | CH(CH₃)CH₂ | 2-CH₃O—C₆H₄ |
| 1.1797 | CH(CH₃)₂ | CH₂ | H | CH(CH₃)CH₂ | 2-CN—C₆H₄ |
| 1.1798 | CH(CH₃)₂ | CH₂ | H | CH(CH₃)CH₂ | 3,4-(CH₃O)₂C₆H₃ |
| 1.1799 | CH(CH₃)₂ | CH₂ | H | CH(CH₃)CH₂ | 2,4-Cl₂—C₆H₃ |
| 1.1800 | CH(CH₃)₂ | CH₂ | H | CH(CH₃)CH₂ | 2,4-(CH₃)₂—C₆H₃ |

TABLE A-continued $$R^1-O-\overset{O}{\underset{\|}{C}}-NH-\underset{\underline{S}}{\overset{CH(CH_3)_2}{\underset{|}{CH}}}-\overset{O}{\underset{\|}{C}}-NH-A-\overset{Y}{\underset{|}{C}}=N-O-Z-Ar \quad (I')$$

| No. | R¹ | A | Y | Z | Ar |
|---|---|---|---|---|---|
| 1.1801 | $CH(CH_3)_2$ | $CH_2$ | H | $CH(CH_3)CH_2$ | $3,4\text{-}(CH_3)_2C_6H_3$ |
| 1.1802 | $CH(CH_3)_2$ | $CH_2$ | H | $CH(CH_3)CH_2$ | $4\text{-}NO_2\text{—}C_6H_4$ |
| 1.1803 | $CH(CH_3)C_2H_5$ | $CH_2$ | H | $CH(CH_3)CH_2$ | $4\text{-}Cl\text{—}C_6H_4$ |
| 1.1804 | $CH(CH_3)C_2H_5$ | $CH_2$ | H | $CH(CH_3)CH_2$ | $4\text{-}CH_3\text{—}C_6H_4$ |
| 1.1805 | $CH(CH_3)C_2H_5$ | $CH_2$ | H | $CH(CH_3)CH_2$ | $4\text{-}CH_3O\text{—}C_6H_4$ |
| 1.1806 | $CH(CH_3)C_2H_5$ | $CH_2$ | H | $CH(CH_3)CH_2$ | $4\text{-}CN\text{—}C_6H_4$ |
| 1.1807 | $CH(CH_3)C_2H_5$ | $CH_2$ | H | $CH(CH_3)CH_2$ | $3\text{-}Cl\text{—}C_6H_4$ |
| 1.1808 | $CH(CH_3)C_2H_5$ | $CH_2$ | H | $CH(CH_3)CH_2$ | $3\text{-}CH_3\text{—}C_6H_4$ |
| 1.1809 | $CH(CH_3)C_2H_5$ | $CH_2$ | H | $CH(CH_3)CH_2$ | $3\text{-}CH_3O\text{—}C_6H_4$ |
| 1.1810 | $CH(CH_3)C_2H_5$ | $CH_2$ | H | $CH(CH_3)CH_2$ | $3\text{-}CN\text{—}C_6H_4$ |
| 1.1811 | $CH(CH_3)C_2H_5$ | $CH_2$ | H | $CH(CH_3)CH_2$ | $2\text{-}Cl\text{—}C_6H_4$ |
| 1.1812 | $CH(CH_3)C_2H_5$ | $CH_2$ | H | $CH(CH_3)CH_2$ | $2\text{-}CH_3\text{—}C_6H_4$ |
| 1.1813 | $CH(CH_3)C_2H_5$ | $CH_2$ | H | $CH(CH_3)CH_2$ | $2\text{-}CH_3O\text{—}C_6H_4$ |
| 1.1814 | $CH(CH_3)C_2H_5$ | $CH_2$ | H | $CH(CH_3)CH_2$ | $2\text{-}CN\text{—}C_6H_4$ |
| 1.1815 | $CH(CH_3)C_2H_5$ | $CH_2$ | H | $CH(CH_3)CH_2$ | $3,4\text{-}(CH_3O)_2C_6H_3$ |
| 1.1816 | $CH(CH_3)C_2H_5$ | $CH_2$ | H | $CH(CH_3)CH_2$ | $2,4\text{-}Cl_2\text{—}C_6H_3$ |
| 1.1817 | $CH(CH_3)C_2H_5$ | $CH_2$ | H | $CH(CH_3)CH_2$ | $2,4\text{-}(CH_3)_2\text{—}C_6H_3$ |
| 1.1818 | $CH(CH_3)C_2H_5$ | $CH_2$ | H | $CH(CH_3)CH_2$ | $3,4\text{-}(CH_3)_2C_6H_3$ |
| 1.1819 | $CH(CH_3)C_2H_5$ | $CH_2$ | H | $CH(CH_3)CH_2$ | $4\text{-}NO_2\text{—}C_6H_4$ |
| 1.1820 | $C(CH_3)_3$ | $CH_2$ | H | $CH(CH_3)CH_2$ | $4\text{-}Cl\text{—}C_6H_4$ |
| 1.1821 | $C(CH_3)_3$ | $CH_2$ | H | $CH(CH_3)CH_2$ | $4\text{-}CH_3\text{—}C_6H_4$ |
| 1.1822 | $C(CH_3)_3$ | $CH_2$ | H | $CH(CH_3)CH_2$ | $4\text{-}CH_3O\text{—}C_6H_4$ |
| 1.1823 | $C(CH_3)_3$ | $CH_2$ | H | $CH(CH_3)CH_2$ | $4\text{-}CN\text{—}C_6H_4$ |
| 1.1824 | $C(CH_3)_3$ | $CH_2$ | H | $CH(CH_3)CH_2$ | $3\text{-}Cl\text{—}C_6H_4$ |
| 1.1825 | $C(CH_3)_3$ | $CH_2$ | H | $CH(CH_3)CH_2$ | $3\text{-}CH_3\text{—}C_6H_4$ |
| 1.1826 | $C(CH_3)_3$ | $CH_2$ | H | $CH(CH_3)CH_2$ | $3\text{-}CH_3O\text{—}C_6H_4$ |
| 1.1827 | $C(CH_3)_3$ | $CH_2$ | H | $CH(CH_3)CH_2$ | $3\text{-}CN\text{—}C_6H_4$ |
| 1.1828 | $C(CH_3)_3$ | $CH_2$ | H | $CH(CH_3)CH_2$ | $2\text{-}Cl\text{—}C_6H_4$ |
| 1.1829 | $C(CH_3)_3$ | $CH_2$ | H | $CH(CH_3)CH_2$ | $2\text{-}CH_3\text{—}C_6H_4$ |
| 1.1830 | $C(CH_3)_3$ | $CH_2$ | H | $CH(CH_3)CH_2$ | $2\text{-}CH_3O\text{—}C_6H_4$ |
| 1.1831 | $C(CH_3)_3$ | $CH_2$ | H | $CH(CH_3)CH_2$ | $2\text{-}CN\text{—}C_6H_4$ |
| 1.1832 | $C(CH_3)_3$ | $CH_2$ | H | $CH(CH_3)CH_2$ | $3,4\text{-}(CH_3O)_2C_6H_3$ |
| 1.1833 | $C(CH_3)_3$ | $CH_2$ | H | $CH(CH_3)CH_2$ | $2,4\text{-}Cl_2\text{—}C_6H_3$ |
| 1.1834 | $C(CH_3)_3$ | $CH_2$ | H | $CH(CH_3)CH_2$ | $2,4\text{-}(CH_3)_2\text{—}C_6H_3$ |
| 1.1835 | $C(CH_3)_3$ | $CH_2$ | H | $CH(CH_3)CH_2$ | $3,4\text{-}(CH_3)_2C_6H_3$ |
| 1.1836 | $C(CH_3)_3$ | $CH_2$ | H | $CH(CH_3)CH_2$ | $4\text{-}NO_2\text{—}C_6H_4$ |

The compounds I are suitable for controlling harmful fungi.

Depending on their chemical and physical properties, they may be formulated with conventional formulation auxiliaries, i.e. formulation auxiliaries known to the person skilled in the art. The products prepared in this manner are called "compositions".

Suitable formulation auxiliaires are, for example, solid or liquid carriers, surfactants and tackifiers.

Liquid carriers are liquid solvents such as water and organic solvents, the latter, especially when using water as solvent, acting as auxiliary solvent. Suitable organic solvents are: aromatics, such as xylene, toluene and alkylnaphthalenes, chlorinated aromatics or chlorinated aliphatic hydrocarbons, such as chlorobenzenes, chloroethylenes and methylene chloride, aliphatic hydrocarbons, such as cyclohexane and paraffins, for example petroleum fractions, alcohols, such as butanol, isobutanol, cyclohexanol and glycol and also the corresponding ethers and esters, ketones, such as acetone, methyl ethyl ketone, methyl isobutyl ketone and cyclohexanone, and aprotic dipolar solvents, such as dimethylformamide, N-methyl-2-pyrrolidone and dimethyl sulfoxide.

Suitable solid carriers are, for example: ground natural minerals and mineral earths such as silicas, silicates, kaolins, clays, bole, loess, talc, chalk, limestone, lime, dolomite, magnesium oxide, quartz, attapulgite, montmorillonite and diatomaceous earth; ground synthetic minerals such as finely divided silica, ground synthetic aluminum oxide or ground synthetic silicates. Solid carriers particularly suitable for granules are, for example: crushed and fractionated natural rocks, such as calcite, marble, pumice and sepiolite; synthetic granules of inorganic and organic meals; granules of organic material such as sawdust, coconut shells, maize cobs or tobacco stalks.

Suitable surfactants are nonionic and anionic emulsifiers/foam-formers and dispersants:

polyoxyethylene fatty acid esters, such as lauryl alcohol polyoxyethylene ether acetate, polyoxyethylene alkyl ethers or polyoxypropylene alkyl ethers, For example of iso-tridecylalcohol, and polyoxyethylene fatty alcohol ethers, alkylaryl alcohol polyoxyethylene ethers, such as octylphenyl polyoxyethylene ether tributylphenyl polyoxyethylene ether ethoxylated iso-octyl-, octyl- or nonylphenol or castor oil, sorbitol esters, arylsulfonic acids, alkylsulfonic acids, alkylsulfuric acids, alkali metal salts, alkaline earth metal salts and ammonium salts of arylsulfonic acids, e.g. ligno-, phenol-, naphthalene- and dibutylnaphthalenesulfonic acid, of alkylsulfonic acids, alkylarylsulfonic acids, alkyl, lauryl ether and fatty alcohol sulfates, fatty acids, sulfated hexa-, hepta- and octadecanols and fatty alcohol glycol ethers, condensates of sulfonated naphthalene and its derivatives with formaldehyde, condensates of naphthalenesulfonic acids with phenol or formaldehyde protein hydrolysates and in particular as dispersants: lignin-sulfite waste liquors and methylcellulose.

Suitable tackifiers are, for example: carboxymethylcellulose; natural and synthetic polymers in the form of powders, granules or latices such as gum arabic, polyvinyl alcohol and polyvinyl acetate, natural phospholipids such as cephalins and lecithins, synthetic phospholipids.

Furthermore, the compositions may comprise one or more examples of the following groups of compounds: colorants, other known active compounds, trace nutrients and other additives.

Suitable colorants are, for example, inorganic pigments, such as iron oxide, titanium oxide, Prussian Blue, furthermore organic dyestuffs, such as alizarin dyestuffs, azo dyestuffs and metal phthalocyanine dyestuffs. Other known active compounds are, for example, other fungicides, and also insecticides, acaricides, herbicides and growth-regulators. Trace nutrients are, for example, salts of iron, manganese, boron, copper, cobalt, molybdenum and zinc. Further suitable additives are, for example, mineral and vegetable oils.

In addition, the compositions may be mixed with other mixing partners of practical importance, such as fertilizers and other ready-to-use active compound compositions.

The compositions are prepared in a manner known per se, i.e. depending on the chemical and physical properties of the substances used, for example by mixing, joint grinding, spraying on, extrusion, granulation, or dissolution in water, the latter, if necessary, with the aid of an organic solvent. Powders, granules and dusts can be obtained for example by mixing or grinding the compounds I together with a solid carrier.

Depending on the substances used, the compositions are, for example, solutions, emulsions, suspensions, powders, foams, pastes, granules, aerosols or microencapsulations in polymeric substances or in coatings for seeds.

For application, the compositions, which are usually commercially available as concentrates, are, if necessary, dissolved, diluted, etc. as is common practice, in the case of spray powders, water-dispersible granules, emulsifiable concentrates, dispersions and also in the case of some microgranules normally by using water. Dusts, granules and spray-solutions are usually not diluted any further with other inert substances prior to application.

The compositions are applied in a manner known per se, for example by spraying, atomizing, dusting, scattering or wetting. Generally, the plants are sprayed or dusted with the compositions. Alternatively or additionally, the seeds of the plants are treated in a manner known per se.

Examples of such preparations are

I. a solution of 90 parts by weight of a compound I according to the invention and 10 parts by weight of N-methyl-2-pyrrolidone, which is suitable for use in the form of microdrops;

II. a mixture of 20 parts by weight of a compound I according to the invention, 80 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil: a dispersion is obtained by finely distributing the solution in water;

III. an aqueous disperson of 20 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 20 parts by weight of a compound I according to the invention, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of a compound I according to the invention, 3 parts by weight of sodium diisobutylnaphthalene-1-sulfonate, 10 parts by weight of the sodium salt of a lignosulfonic acid from a sulfite waste liquor and 7 parts by weight of pulverulent silica gel: a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil which has been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, it being possible for this dispersion to be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffinic mineral oil.

If the compounds I are applied as such, a fine distribution is essential.

The compounds I and the compositions according to the invention have an outstanding activity against a broad spectrum of harmful fungi (phytopathogenic fungi), in particular from the classes of the Ascomycetes, Basidiomycetes, Deuteromyces and Phycomycetes.

Some of them act systemically and can be employed as foliar- and soil-acting fungicides.

They are especially important for controlling a large number of fungi in a variety of crop plants, such as wheat, rye, barley, oats, rice, maize, lawns, cotton, soy, coffee, sugar cane, grapevines, fruit species, ornamentals and vegetable species such as cucumbers, beans and cucurbits as well as the seeds of these plants.

The compounds I, their salts and N-oxides and the compositions according to the invention are applied by treating the harmful fungi, their habitat, or the seeds, plants, areas, materials or the spaces to be protected against fungal infection, with a fungicidally active amount of the compositions or of the compounds I. Application may be effected before or after infection by the fungi.

Specifically, the compositions according to the invention and the compounds I are suitable for controlling the following plant diseases:

Erysiphe graminis (powdery mildew) in cereals, Erysiphe cichoracearum and Sphaerotheca fuliginea in cucurbits, Podosphaera leucotricha in apples, Uncinula necator in grape vines, Puccinia species in cereals, Rhizoctonia species in cotton, rice and lawns, Ustilago species in cereals and sugar cane, Venturia inaequalis (scab) in apples, Helminthosporium species in cereals, Septoria nodorum in wheat, Botrytis cinerea (gray mold) in strawberries, grapevines, ornamentals and vegetables, Cercospora arachidicola in groundnuts, Pseudocercosporella herpotrichoides in wheat, barley, Pyricularia oryzae in rice, Phytophthora infestans in potatoes and tomatoes, Fusarium and Verticillium species in a variety of plants, Plasmopara viticola in grape vines, Pseudoperonospora species in hops and cucumbers and Alternaria species in vegetables and fruit.

In general, the fungicidal compositions comprise from 0.1 to 95, preferably from 0.5 to 90, % by weight of active compound.

Depending on the nature of the desired effect, the rates of application are from 0.01 to 2.0 kg of active compound per ha.

In the treatment of seed, amounts of from 0.001 to 0.1 g, preferably 0.01 to 0.05 g of active compound are generally required per kilogram of seed.

The compositions according to the invention in the use form as fungicides may also be present together with other active compounds, e.g. with herbicides, insecticides, growth regulators, fungicides or else with fertilizers.

In many cases, a mixture with other fungicides results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfide, ammonia complex of zinc (N,N-ethylene-bis-dithiocarbamate), ammonia complex of zinc (N,N'-propylene-bis-dithiocarbamate), zinc (N,N'-propylene-bis-dithiocarbamate), N,N'-polypropylene-bis-(thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2, 4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-(1-(2,2,2-trichloroethyl)formamide, 1-(3,4-dichloroanilino)-1-formylamino-2,2,2-trichloroethane, 2,6-dimethyl-N-tridecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1, 3-dioxolan-2-ylethyl]-1H-1, 2,4-triazole, N-(n-propyl)-N-(2,4,6-trichlorophenoxyethyl)-N'-imidazolylurea, 1-(4-chlorophenoxy)-3,3-dimethyl-1-(1H-1,2, 4-triazol-1-yl)-2-buta none, (2-chlorophenyl)-(4-chlorophenyl)-5-pyrimidinemethanol, 5-butyl-2-dimethylamino-4-hydroxy-6-methylpyrimidine, bis (p-chlorophenyl)-3-pyrimidinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl) alanine methyl ester, 5-methyl-5-vinyl-3-(3, 5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro- 2-aminopyridine, 1-((bis-(4-fluorophenyl) methylsilyl)methyl)-1H-1,2,4-triazole, strobilurins, such as methyl E-methoximino-[α-(o-tolyloxy)-o-tolyl]acetate, methyl E-2-{2-[6-(2-cyanophenoxy)pyridimin-4-yl-oxy]phenyl}-3-methoxyacrylate, N-methyl-E-methoximino-[α-(2-phenoxyphenyl)]acetamide, N-methyl-E-methoximino-[α-(2,5-dimethyloxy)-o-tolyl]acetamide.

Anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl)aniline.

Phenylpyrroles, such as 4-(2,2-difluoro-1,3-benzodioxol-4-yl)pyrrole-3-carbonitrile.

Cinnamamides, such as 3-(4-chlorophenyl)-3-(3,4-dimethoxyphenyl)acryloylmorpholide.

(2RS,3SR)-1-[3-(2-chlorophenyl)-2-[4-fluorophenyl] oxiran-2-ylmethyl]-1H-1,2,4-triazole.

PREPARATION EXAMPLES

The procedures of the preparation examples below may be employed to prepare further representatives of the compounds I by modifying the starting materials. The physical data of the products prepared in this way are listed in the following tables.

The chemical shifts (in ppm) of the $^1$H NMR spectra were referenced to tetramethylsilane.

N-(iso-Propyloxycarbonyl)-L-valine-2-(3-p-chlorobenzyloxyimino)butylamide (Compound 2.4 in Table S1)

1. N-(iso-Propyloxycarbonyl)-L-valine-2-(3-hydroxy) butylamide

To a solution of 20.9 g (96 mmol) of N-(isopropyloxycarbonyl)-L-valine and 8.6 g (96 mmol) of 2-amino-3-hydroxybutane in 200 ml of toluene were added 10.1 g (0.1 mol) of triethylamine. At 10° C., 16.8 g (96 mmol) of 93% strength diethyl cyanophosphonate were then added dropwise and the mixture was stirred at room temperature overnight. After the addition of 150 ml of ethyl acetate, the mixture was washed with 2N sodium hydroxide solution and 10% strength hydrochloric acid (300 ml each). The organic phase was dried, concentrated and combined with the solids that had separated off during the extraction. This gave 12.9 g of N-(isopropyloxycarbonyl)-L-valine-2-(3-hydroxy)butylamide.

Mp. 152° C.

2. N-(iso-Propyloxycarbonyl)-L-valine-2-(3-oxo) butylamide 5.2 g (20 mmol) of N-(isopropyloxycarbonyl)-L-valine-2-(3-hydroxy)butylamide, 0.2 g of 2,2,6,6-tetramethyl-1-piperidinyloxy, 0.12 g of potassium bromide, 0.31 g of sodium dihydrogen phosphate and 0.36 g of disodium hydrogen phosphate were added to a two-phase-mixture of dichloromethane and water (100 ml each). At room temperature, 11.2 g of an about 13% strength sodium hypochlorite solution were then added dropwise over 90 minutes during which a pH of 6 to 7 was maintained, checking with a pH electrode. Stirring was then continued for a further hour before more dichloromethane was added and the organic phase was separated off. The organic phase was washed twice with water, dried and concentrated. The resulting residue was finally purified chromatographically over silica gel. After concentration of the desired fractions, this gave 3.7 g of N-(isopropyloxycarbonyl)-L-valine-2-(3-oxo)butylamide.

Mp. 125–134° C.

$^1$H NMR (CDCl$_3$): 6.6; 5.1 (N—H); 4.9; 4.6; 4.0 (1H each) ; 2.1 (3 H); 2.0 (1H); 1.4 (3H); 1.2 and 0.9 (6H each).

3. N-(isopropyloxycarbonyl)-L-valine-2-(3-p-chlorobenzyloxyimino)butylamide (Compound 2.4 in Table S1)

At 60° C., a solution of 1.1 g (4 mmol) of N-(isopropyloxycarbonyl)-L-valine-2-(3-oxo)butylamide in 20 ml of ethanol was added dropwise to the solution of 0.4 g of sodium acetate and 0.9 g (6 mmol) of p-chlorobenzyloxyamine in 30 ml of ethanol and 10 ml of water. After the mixture had been heated under reflux for 6 hours, it was stirred at room temperature for 15 hours. Water was added and the precipitate was filtered off, washed with hexane and water and dried. This gave 1.0 g (2.4 mmol) of the title compound.

Mp. 144–147° C.

TABLE S1

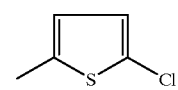

(I′)

| | R$^1$ | A | Y | Z | Ar | Mp. [° C.] |
|---|---|---|---|---|---|---|
| 2.1 | CH(CH$_3$)$_2$ | CH(CH$_3$) | CH$_3$ | CH$_3$ | — | 161 |
| 2.2 | CH(CH$_3$)$_2$ | CH(CH$_3$) | CH$_3$ | CH$_2$CH$_2$CH(CH$_3$)$_2$ | — | 120–8 |
| 2.3 | CH(CH$_3$)$_2$ | CH(CH$_3$) | CH$_3$ | CH$_2$CH$_2$ | 4-Cl—C$_6$H$_4$ | 116 |
| 2.4 | CH(CH$_3$)$_2$ | CH(CH$_3$) | CH$_3$ | CH$_2$ | 4-Cl—C$_6$H$_4$ | 144–7 |
| 2.5 | CH(CH$_3$)$_2$ | CH(CH$_3$) | CH$_3$ | CH$_2$CH$_2$CHCH | 3,4-Cl$_2$—C$_6$H$_3$ | 148 |
| 2.6 | CH(CH$_3$)$_2$ | CH(CH$_3$) | CH$_3$ | CH$_2$CCH | — | 143 |
| 2.7 | CH(CH$_3$)$_2$ | CH(CH$_3$) | CH$_3$ | CH$_2$CH$_2$O | 2-Cl—C$_6$H$_4$ | 119 |
| 2.8 | CH(CH$_3$)$_2$ | CH(CH$_3$) | CH$_3$ | CH$_2$ | β-naphthyl | 195 |
| 2.9 | CH(CH$_3$)$_2$ | CH(CH$_3$) | CH$_3$ | CH$_2$ | ![thiophene-Cl] | 164 |
| 2.10 | CH(CH$_3$)$_2$ | CH(CH$_3$) | CH$_3$ | CH$_2$CH$_2$ | 3,4-(MeO)$_2$—C$_6$H$_3$ | 147 |
| 2.11 | C(CH$_3$)$_3$ | CH(CH$_3$) | CH$_3$ | CH$_2$ | 4-Cl—C$_6$H$_4$— | 116 |
| 2.12 | CH(CH$_3$)$_2$ | CH(CH$_3$) | C$_6$H$_5$ | H | — | 50 |
| 2.13 | CH(CH$_3$)$_2$ | CH(CH$_3$) | C$_6$H$_5$ | CH$_3$ | — | 172 |
| 2.14 | CH(CH$_3$)$_2$ | CH$_2$ | C$_6$H$_5$ | CH$_2$ | 4-Cl—C$_6$H$_4$ | 120 |
| 2.15 | CH(CH$_3$)$_2$ | CH(CH$_3$) | H | CH$_2$ | 4-Cl—C$_6$H$_4$ | 116 |
| 2.16 | CH(CH$_3$)$_2$ | CH(C$_6$H$_5$) | H | CH$_3$ | — | 155–8 |
| 2.17 | CH(CH$_3$)$_2$ | CH(C$_6$H$_5$) | H | CH$_2$ | 4-Cl—C$_6$H$_4$ | 138–42 |
| 2.18 | CH(CH$_3$)$_2$ | CH(CH$_3$) | CH$_3$ | CH$_2$ | 2-CH$_3$—C$_6$H$_4$ | 172–80 |
| 2.19 | CH(CH$_3$)$_2$ | CH(CH$_3$) | CH$_3$ | CH$_2$ | C$_6$H$_5$ | 150–2 |
| 2.20 | CH(CH$_3$)$_2$ | CH(CH$_3$) | CH$_3$ | CH$_2$ | 3-MeO-C$_6$H$_4$ | 126–8 |
| 2.21 | CH(CH$_3$)$_2$ | CH(CH$_3$) | CH$_3$ | CH$_2$ | 3,4-Cl$_2$C$_6$H$_3$ | 178–80 |
| 2.22 | CH(CH$_3$)$_2$ | CH(CH$_3$) | CH$_3$ | CH$_2$-cycloC$_6$H$_{12}$ | — | 134–6 |
| 2.23 | CH(CH$_3$)$_2$ | CH(CH$_3$) | CH$_3$ | CH$_2$ | 4-tBu-C$_6$H$_4$ | 120–3 |
| 2.24 | CH(CH$_3$)$_2$ | CH(CH$_3$) | CH$_3$ | (CH$_2$)$_4$ | 4-F—C$_6$H$_4$ | 104–10 |
| 2.25 | CH(CH$_3$)$_2$ | CH(CH$_3$) | CH$_3$ | CH$_2$CH$_2$CHCH | 4-Cl—C$_6$H$_4$ | 173–5 |
| 2.26 | CH(CH$_3$)$_2$ | CH(CH$_3$) | CH$_3$ | CH$_2$CH$_2$O | 2-F—C$_6$H$_4$ | 144–6 |

TABLE S1-continued (I')

$$R^1-O-C(=O)-NH-CH(CH(CH_3)_2)-C(=O)-NH-A-C(Y)=N-O-Z-Ar$$

| | $R^1$ | A | Y | Z | Ar | Mp. [° C.] |
|---|---|---|---|---|---|---|
| 2.27 | $CH(CH_3)_2$ | $CH(CH_3)$ | $CH_3$ | $CH(CH_3)$ | $4\text{-Cl}-C_6H_4$ | 158–60 |
| 2.28 | $CH(CH_3)_2$ | $CH(CH_3)$ | $CH_3$ | $CH(\text{cyclo-}C_3H_5)$ | $4\text{-Cl}-C_6H_4$ | oil |
| 2.29 | $CH(CH_3)_2$ | $CH(CH_3)$ | $CH_3$ | $CH_2C(CH_2)CH_3$ | — | 155–8 |
| 2.30 | $CH(CH_3)_2$ | $CH(CH_3)$ | H | $CH_2CH_2CHCH$ | $4\text{-Cl}-C_6H_4$ | 104–8 |
| 2.31 | $CH(CH_3)_2$ | $CH(CH_3)$ | H | $CH_2$ | $2\text{-CH}_3-C_6H_4$ | 148–50 |
| 2.32 | $CH(CH_3)_2$ | $CH(CH_3)$ | H | $CH_2CH_2O$ | $2\text{-Cl}-C_6H_4$ | 108–12 |
| 2.33 | $CH(CH_3)_2$ | $CH(CH_3)$ | H | $CH_2CH_2O$ | $3,4\text{-(MeO)}_2-C_6H_3$ | oil |
| 2.34 | $CH(CH_3)_2$ | $CH(CH_3)$ | H | $CH_2$ | $3,4\text{-Cl}_2-C_6H_3$ | 138–40 |
| 2.35 | $CH(CH_3)_2$ | $CH(CH_3)$ | H | $CH_2CH_2O$ | $2\text{-Cl}-C_6H_4$ | oil |
| 2.36 | $CH(CH_3)_2$ | $CH(CH_3)$ | $CH_3$ | $CH_2$ | $4\text{-MeO}-C_6H_4$ | 130–2 |
| 2.37 | $CH(CH_3)_2$ | $CH(CH_3)$ | $CH_3$ | $CH_2$ | $4\text{-CH}_3-C_6H_4$ | 157–9 |
| 2.38 | $CH(CH_3)_2$ | $CH(CH_3)$ | $CH_3$ | $CH_2$ | $4\text{-CN}-C_6H_4$ | 163–5 |
| 2.39 | $CH(CH_3)_2$ | $CH(CH_3)$ | $CH_3$ | $CH_2$ | $3\text{-CN}-C_6H_4$ | 134 |
| 2.40 | $CH(CH_3)_2$ | $CH(CH_3)$ | $CH_3$ | $CH_2$ | $3\text{-Cl}-C_6H_4$ | 140 |
| 2.41 | $CH(CH_3)_2$ | $CH(CH_3)$ | $CH_3$ | $CH_2$ | $2\text{-Cl}-C_6-C_6H_4$ | 171–6 |
| 2.42 | $CH(CH_3)_2$ | $C(CH_3)_2CH_2$ | $CH_3$ | $CH_2$ | $2\text{-Cl}-C_6H_4$ | oil |
| 2.43 | $CH(CH_3)_2$ | $C(CH_3)_2CH_2$ | $CH_3$ | $CH_2$ | $3\text{-Cl}-C_6H_4$ | oil |
| 2.44 | $CH(CH_3)_2$ | $C(CH_3)_2CH_2$ | $CH_3$ | $CH_2$ | $4\text{-MeO}-C_6H_4$ | oil |
| 2.45 | $CH(CH_3)_2$ | $C(CH_3)_2CH_2$ | $CH_3$ | $CH_2$ | $3\text{-CN}-C_6H_4$ | oil |
| 2.46 | $CH(CH_3)_2$ | $CH(CH_3)$ | H | $CH_2$ | $4\text{-MeO}-C_6H_4$ | 126 |
| 2.47 | $CH(CH_3)_2$ | $CH(CH_3)$ | H | $CH_2$ | $3\text{-CN}-C_6H_4$ | 83–7 |
| 2.48 | $CH(CH_3)_2$ | $C(CH_3)_2CH_2$ | $CH_3$ | $CH_2$ | $4\text{-CH}_3-C_6H_4$ | oil |
| 2.49 | $CH(CH_3)_2$ | $CH(CH_3)$ | H | $CH_2$ | $4\text{-CH}_3-C_6H_4$ | 128 |
| 2.50 | $CH(CH_3)_2$ | $CH(CH_3)$ | H | $CH_2$ | $4\text{-CN}-C_6H_4$ | 112–4 |
| 2.51 | $CH(CH_3)_2$ | $CH(CH_3)$ | H | $CH_2$ | $3\text{-Cl}-C_6H_4$ | 124–7 |
| 2.52 | $CH(CH_3)_2$ | $C(CH_3)_2CH_2$ | $CH_3$ | $CH_2$ | $3\text{-Cl}-C_6H_4$ | oil |
| 2.53 | $CH(CH_3)_2$ | $C(CH_3)_2CH_2$ | $CH_3$ | $CH_2$ | $4\text{-CN}-C_6H_4$ | oil |

USE EXAMPLES

For the tests below on the fungicidal activity of the compounds I, an emulsion was used comprising 10% by weight of the active compound and 90% by weight of a mixture of 70% by weight of Cyclohexanol, 20% by weight of Nekanil® LN (Lutensol® AP6, wetting agent with emulsifying and dispersant action based on ethoxylated alkylphenols) and 10% by weight of Uniperol® EL (nonionic emulsifier based on ethoxylated castor oil)

The desired active compound concentrations were achieved by diluting this emulsion with water. The extent of the infestation was determined visually.

We claim:

1. Carbamoylcarboxamide oximes of the formula I (I)

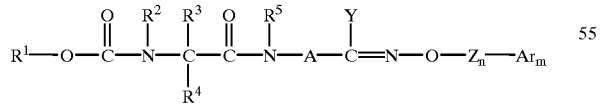

or salts thereof, where the variables have the following meanings:

$R^1$ is $C_1$–$C_8$-alkyl, $C_2$–$C_8$-alkenyl or $C_2$–$C_8$-allynyl, it being possible for these radicals to be partially or fully halogenated and/or to carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, $C_3$–$C_7$-cycloalyl, $C_3$–$C_7$-cycloalkenyl, aryl, aryloxy and hetaryl, it being in turn possible for the cyclic radicals to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, $C_3$–$C_7$-cycloalkyl or $C_3$–$C_7$-cycloalkenyl, it being possible for these radicals to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, a non-aromatic 4- to 8-membered ring which, as ring members, in addition to carbon may contain one or two of the hetero atoms oxygen, sulfur and nitrogen, it being possible for the carbons in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, the second and any further nitrogen as ring heteroatom carrying hydrogen or a $C_1$–$C_4$-alkyl group, aryl or hetaryl, it being possible for the these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, it being in turn possible for the cyclic substituents to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, $W^1W^2C{=}N{-}$, where $W^1$ is $C_1$–$C_8$-alkyl which may be partially or fully halogenated and/or carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, aryl, aryloxy and hetaryl, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy, $C_2$–$C_8$-alkenyl or $C_2$–$C_8$-alkynyl, it being possible for these radicals to be partially or fully halogenated and/or to carry one or independently two or three of the following groups: cyano, $C_1$–$C_4$-allyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, $C_3$–$C_7$-cycloalkyl or $C_3$–$C_7$ cycloalkenyl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryl-($C_1$–$C_4$)-alkyl, it being possible for the aryl-containing groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, aryl or hetaryl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy and $W^2$ is hydrogen or independently one of the groups $W^1$;

$R^2$ is hydrogen or is $C_1$–$C_8$-alkyl or $C_3$–$C_7$-cycloalkyl, both of which may be partially or fully halogenated;

$R^3$ is $C_1$–$C_8$-alkyl or $C_3$–$C_7$-cycloalkyl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl or phenyl-($C_1$–$C_4$)-alkyl, it being possible for the phenyl radical to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

$R^4$ is hydrogen or one of the groups listed under $R^3$ or $R^3$ and $R^4$, together with the carbon that they are attached to, form a 4- to 8-membered ring which, as ring members, in addition to carbon may contain one or two of the hetero atoms oxygen, sulfur and nitrogen, it being possible for the carbons in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, nitrogen as hetero atom carrying hydrogen or a $C_1$–$C_4$-alkyl group;

$R^5$ is a radical $R^2$;

A is $C_1$–$C_8$-alkyl, it being possible for these radicals to be partially or fully halogenated and/or to carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, aryl and aryloxy, or $C_3$–$C_7$-cycloalkyl, it being possible for these radicals to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

Y is hydrogen, $C_1$–$C_8$-alkyl, it being possible for this radical to be partially or fully halogenated and/or to carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, aryl and aryloxy, $C_3$–$C_7$-cycloalkyl, it being possible for this radical to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy or aryl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

Z is $C_1$–$C_8$-alkyl, it being possible for this radical to be partially or fully halogenated or fully halogenated and/or to carry one or independently two or three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, aryl and aryloxy, $C_1$–$C_8$-alkoxy, it being possible for this radical to be partially or fully halogenated and/or to carry one or independently two or three of the following groups: cyano, $C_1$–$C_4$-alkylthio and $C_1$–$C_4$-alkoxycarbonyl, aryl and aryloxy, $C_3$–$C_7$-cycloalkyl, it being possible for this radical to be partially or fully halogenated and/or to carry one or independently two or three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being in turn possible for the cyclic groups to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

n is 0, 1 or 2;

Ar is aryl or hetaryl, it being possible for these radicals to carry one or independently two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, it being in turn possible for the cyclic substituents to carry one or independently two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxy-carbonyl;

m is 0, 1 or 2; with the proviso that n and m are not simultaneously 0.

2. A process for preparing carbamoylcarboxamide oximes of the formula I as claimed in claim 1, which comprises reacting a carbamoyl carboxylic acid of the general formula II

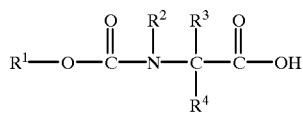
(II)

with an amine of the general formula III

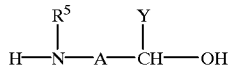
(III)

to give an amide IV

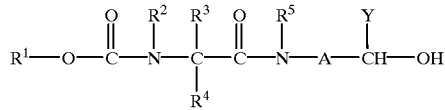
(IV)

and then oxidizing IV to give the carbonyl compound V

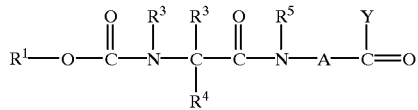
(V)

and reacting V with an oxyamine VI

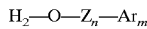
(VI).

3. A process for preparing carbamoylcarboxamide oximes of the formula I as claimed in claim 1, which comprises:

a) converting a carbamoylcarboxamide of the general formula I

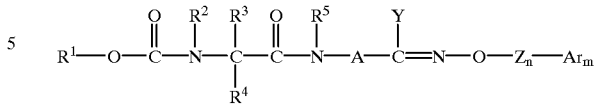
(I)

where the group $R^1$—O—(CO) is a protecting group which can be removed in a conventional manner into an amino acid amide VII

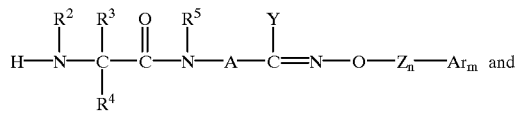
(VII)

and b) reacting the amino acid amide VII obtained in this manner with a chloroformyl oxime of the general formula VIII

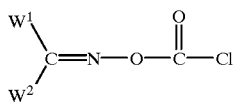
(VIII)

in the presence of a base.

4. Compositions suitable for controlling harmful fungi, comprising a fungicidally active amount of a compound of the formula I or a salt thereof as claimed in claim 1 and at least one customary formulation auxiliary.

5. A process for controlling harmful fungi, comprising treating the harmful fungi, their habitat, the plants, areas materials or spaces to be kept free from them with an effective amount of the compound of claim 1 or a salt thereof.

6. The composition of claim 4, wherein said fungicidally active amount is 0.1 to 95% by weight.

7. The composition of claim 4, wherein said fungicidally active amount is 0.5 to 90% by weight.

8. The composition of claim 4, wherein said composition further comprises a second active agent selected from the group consisting of herbicides, insecticides, growth regulators, fungicides and fertilizers.

9. The process of claim 5, wherein said treating is 0.01 to 2.0 kg of the compound per hectare.

10. A process for controlling harmful fungi, comprising treating the harmful fungi, their habitat, the plants, areas materials or spaces to be kept free from them with an effective amount of the composition of claim 4.

11. A process for controlling harmful fungi, comprising treating the harmful fungi, their habitat, the plants, areas materials or spaces to be kept free from them with an effective amount of the composition of claim 6.

12. A process for controlling harmful fungi, comprising treating the harmful fungi, their habitat, the plants, areas materials or spaces to be kept free from them with an effective amount of the composition of claim 7.

13. A process for controlling harmful fungi, comprising treating the harmful fungi, their habitat, the plants, areas materials or spaces to be kept free from them with an effective amount of the composition of claim 8.

14. The process of claim 10, wherein said treating is 0.01 to 2.0 kg of the compound per hectare.

15. The process of claim 11, wherein said treating is 0.01 to 2.0 kg of the compound per hectare.

16. The process of claim 12, wherein said treating is 0.01 to 2.0 kg of the compound per hectare.

17. The process of claim 13, wherein said treating is 0.01 to 2.0 kg of the compound per hectare.

18. The carbamoylcarboximide oxime of claim 1, wherein n=m=1.

19. The carbamoylcarboximide oxime of claim 1, wherein $R^1$ is isopropyl, sec-butyl, tert-butyl or phenyl;

$R^2$ is hydrogen;

$R^3$ and $R^4$ are different and are hydrogen or isopropyl;

$R^5$ is hydrogen;

A is $CH_2CH_2$, $CH_2$; $C(CH_3)_2$, $CH(CH_3)CH_2$, or $CH(CH_3)$;

Y is phenyl, methyl, or hydrogen;

Z is $CH_2O$, $CH_2CH_2$, $CH(CH_3)$, or $CH_2$;

n is 1 or 2;

Ar is unsubstituted or substituted phenyl;

m is 1.

20. The carbamoylcarboximide oxime of claim 19, wherein the carbon attached to $R^3$ and $R^4$ is in the S configuration.

21. The carbamoylcarboximide oxime of claim 19, wherein A is racemic $CH(CH_3)$ or $CH(CH_3)$ in the R configuration.

22. The carbamoylcarboximide oxime of claim 19, wherein Ar is phenyl substituted with chlorine, methyl, methoxy or cyano.

* * * * *